US009398761B2

(12) United States Patent
Arteta et al.

(10) Patent No.: US 9,398,761 B2
(45) Date of Patent: Jul. 26, 2016

(54) TRANSGENIC ANIMAL MODEL OF MOOD DISORDERS

(71) Applicant: BRAINCO BIOPHARMA, S.L., Derio (ES)

(72) Inventors: David Arteta, Derio (ES); Marcelo Ferrer, Derio (ES); Laureano Simon, Derio (ES); Antonio Martinez, Derio (ES); Maria Uribarri, Derio (ES)

(73) Assignee: Brainco Biopharma, S.L., Derio (ES)

( * ) Notice: Subject to any disclaimer, the term of this patent is extended or adjusted under 35 U.S.C. 154(b) by 0 days.

(21) Appl. No.: 14/386,319

(22) PCT Filed: Mar. 14, 2013

(86) PCT No.: PCT/EP2013/055253
§ 371 (c)(1),
(2) Date: Sep. 18, 2014

(87) PCT Pub. No.: WO2013/139676
PCT Pub. Date: Sep. 26, 2013

(65) Prior Publication Data
US 2015/0047060 A1 Feb. 12, 2015

(30) Foreign Application Priority Data
Mar. 19, 2012 (GB) .................................. 1204816.1

(51) Int. Cl.
| | |
|---|---|
| *A01K 67/00* | (2006.01) |
| *A01K 67/027* | (2006.01) |
| *C07K 14/475* | (2006.01) |
| *C12N 15/85* | (2006.01) |
| *G01N 33/68* | (2006.01) |
| *G01N 33/50* | (2006.01) |
| *C07K 16/22* | (2006.01) |
| *C12N 15/113* | (2010.01) |
| *C12Q 1/68* | (2006.01) |

(52) U.S. Cl.
CPC ........... *A01K 67/0275* (2013.01); *C07K 14/475* (2013.01); *C07K 16/22* (2013.01); *C12N 15/1136* (2013.01); *C12N 15/8509* (2013.01); *C12Q 1/6883* (2013.01); *G01N 33/5058* (2013.01); *G01N 33/5088* (2013.01); *G01N 33/6896* (2013.01); *A01K 2217/052* (2013.01); *A01K 2217/206* (2013.01); *A01K 2227/105* (2013.01); *A01K 2267/0306* (2013.01); *A01K 2267/0356* (2013.01); *C12N 2830/008* (2013.01); *C12Q 2600/118* (2013.01); *C12Q 2600/136* (2013.01); *C12Q 2600/158* (2013.01); *G01N 2333/475* (2013.01); *G01N 2500/10* (2013.01)

(58) Field of Classification Search
USPC ................. 800/3, 4, 8, 9, 13, 18, 21
See application file for complete search history.

(56) References Cited

U.S. PATENT DOCUMENTS

| | | | |
|---|---|---|---|
| 6,211,428 B1 | 4/2001 | Singh et al. | |
| 6,504,080 B1 * | 1/2003 | Van Der Putten .. | A01K 67/0275 435/320.1 |
| 6,572,851 B2 * | 6/2003 | Muramatsu ............ | A61K 38/18 424/198.1 |
| 7,888,485 B2 * | 2/2011 | Tso .................. | A61K 47/48546 424/141.1 |

FOREIGN PATENT DOCUMENTS

| | | |
|---|---|---|
| WO | WO 98/03644 | 1/1998 |
| WO | WO 01/64944 | 9/2001 |
| WO | WO 01/84921 | 11/2001 |
| WO | WO 2004/047727 | 6/2004 |
| WO | WO 2005/017203 | 2/2005 |
| WO | WO 2005/047530 | 5/2005 |
| WO | WO 2006/002262 | 1/2006 |
| WO | WO 2006/020684 | 2/2006 |
| WO | WO 2006/108201 | 10/2006 |
| WO | WO 2010/039526 | 4/2010 |
| WO | WO 2011/154037 | 12/2011 |

OTHER PUBLICATIONS

Dierssen et al. PlosOne 2011, Feb. 25, 2011.*
Houdebine, 1994 J. Biotech. 34, p. 269-87.*
Mullins J Clin Invest, 1996;97:1557-60.*
Wall, J Dairy Sci 1997;80:2213-24.*
Gama Sosa et al., "Modeling human neurodegenerative diseases in transgenic systems," *Human Genetics*, vol. 131, pp. 535-563, 2012.
Hashimoto-Gotoh et al., "Bone mass increase specific to the female in a line of transgenic mice overexpressing human osteoblast stimulating factor-1," *Journal of Bone and Mineral Metabolism*, vol. 22, pp. 278-282, 2004.
Pavlov et al., "Enhanced Hippocampal GABAergic Inhibition in Mice Overexpressing Heparin-Binding Growth-Associated Molecule," *Neuroscience*, vol. 139, pp. 505-511, 2006.
Pavlov et al., "Role of Heparin-Binding Growth-Associated Molecule (HB-GAM) in Hippocampal LTP and Spatial Learning Revealed by Studies on Overexpressing and Knockout Mice," *Molecular and Cellular Neuroscience*, vol. 20, pp. 330-342, 2002.
Takahashi et al., "Increased expression of receptor phosphotyrosine phosphatae-β/ζ is associated with molecular, cellular, behavioral and cognitive schizophrenia phenotypes," *Translational Psychiatry*, vol. 1, e08, 2011, (10 pages).

(Continued)

*Primary Examiner* — Janice Li
(74) *Attorney, Agent, or Firm* — Klarquist Sparkman, LLP

(57) ABSTRACT

A non-human transgenic animal having a polynucleotide encoding a PTN polypeptide, which polynucleotide is operably linked to a promoter, wherein said transgenic animal has greater than wild-type expression of the PTN polypeptide in at least one brain region, as well as related vectors, methods of producing transgenic animals, in vitro and in vivo screening methods for potential therapeutic agents, and methods for treating and diagnosing neuropsychiatric illnesses, particularly anxiety and depression, are disclosed.

9 Claims, 20 Drawing Sheets

(56) References Cited

OTHER PUBLICATIONS

Tare et al., "Effect of targeted overexpression of pleiotrophin on postnatal bone development," *Biochemical and Biophysical Research Communication*, vol. 298, pp. 324-332, 2002.

Belmaker et al., "Major Depressive Disorder," *The New England Journal of Medicine*, vol. 358, pp. 55-68, 2008.

Calvet et al., Pleiotrophin, a candidate gene for poor tumor vasculature and in vivo neuroblastoma sensitivity to irinotecan, *Oncogene*, vol. 25, pp. 3150-3159, 2006.

Chen et al., "Pleiotrophin is highly expressed by myeloma cells and promotes myeloma tumor growth," *Blood*, vol. 110. pp. 287-295, 2007.

Christensen et al., "Cytoreductive antitumor activity of PF-2341066, a novel inhibitor of anaplastic lymphoma kinase and c-Met, in experimental models of anaplastic large-cell lymphoma" *Mol. Cancer. Ther.*, vol. 6, pp. 3314-3322, 2007.

DellaGioia et al., "A critical review of human endotoxin administration as an experimental paradigm of depression," *Neuroscience and Behavioral Reviews*, vol. 34, pp. 130-143, 2010.

Deuel et al., "Pleiotrophin: A Cytokine with Diverse Functions and a Novel Signaling Pathway," *Archives of Biochemistry and Biophysics*, vol. 397, No. 2, pp. 162-171, 2002.

Diamantopoulou et al., "A Pleiotrophin C-terminus peptide induces anti-cancer effects through RPTPβ/ζ," *Molecular Cancer*, 9:224, 2010 (13 pages).

Dunn et al., "Cytokines as mediators of depression: What can we learn from animal studies?" *Neuroscience and Biobehavioral Reviews*, vol. 29, pp. 891-909, 2005.

Furuta et al., "Identification of pleiotrophin in conditioned medium secreted from neural stem cells by SELDI-TOF and SELDI-tandem mass spectrometry," *Developmental Brain Research*, vol. 152, pp. 189-197, 2004.

Hamma-Kourbali et al., "Inhibition of the Mitogenic, Angiogenic and Tumorigenic Activities of Pleiotrophin by a Synthetic Peptide Corresponding to its C-Thrombospondin Repeat-I Domain," *Journal of Cellular Physiology*, vol. 214, pp. 250-259, 2008.

Heinrich et al., "Kinase Mutations and Imatinib Response in Patients With Metastatic Gastrointestinal Stromal Tumor," *Journal of Clinical Oncology*, vol. 21, pp. 4342-4349, 2003.

Herry et al., "Prefrontal Cortex Long-Term Potentiation, But Not Long-Term Depression, is Associated with the Maintenance of Extinction of Learned Fear in Mice," *The Journal of Neuroscience*, vol. 22, No. 2, pp. 577-583, 2002.

Holderbach et al., "Enhanced Long-Term Synaptic Depression in an Animal Model of Depression," *Biological Psychiatry*, vol. 62, pp. 92-100, 2007.

Huang et al., "Structure-Based Design and Discovery of Novel Inhibitors of Protein Tyrosine Phosphatases," *Bioorganic & Medicinal Chemistry*, vol. 11, pp. 1835-1849, 2003.

Kadomatsu et al., "Midkine and pleiotrophin in neural development and cancer," *Cancer Letters*, vol. 204, pp. 127-143, 2004.

Krishnan et al., "The molecular neurobiology of depression," *Nature*, vol. 455, pp. 894-902, 2008.

Krishnan et al., "Linking Molecules to Mood: New Insight Into the Biology of Depression," *American Journal of Psychiatry*, vol. 167, pp. 1305-1320, 2010.

Lee et al., "Depression research: where are we now?," *Molecular Brain*, 3:8, 2010 (10 pages).

Lorente et al., "Functional comparison of long and short splice forms of RPTPβ: Implications for glioblastoma treatment," *Neuro-Oncology*, vol. 7, pp. 154-163, 2005.

Mikelis et al., "A Peptide Corresponding to the C-terminal Region of Pleiotrophin Inhibits Angiogensis In Vivo and In Vitro," *Journal of Cellular Biochemistry*, vol. 112, pp. 1532-1543, 2011.

Milner et al., "Cloning, Nucleotide Sequence, and Chromosome Localization of the Human Pleiotrophin Gene," *Biochemistry*, vol. 31, No. 48, 12023-12028, 1992.

Sabbatini et al., "GSK1838705A inhibits the insulin-like growth factor-1 receptor and anaplastic lymphoma kinase and shows antitumor activity in experimental models of human cancers," *Molecular Cancer Therapeutics*, vol. 8, pp. 2811-2820, 2009.

Stewart et al., "Antidepressant mechanism: functional and molecular correlates of excitatory amino acid neurotransmission," *Molecular Psychiatry*, vol. 7, pp. S15-S22, 2002.

Sullivan et al., "Genetic Epidemiology of Major Depression: Review and Meta-Analysis," *American Journal of Psychiatry*, vol. 157, pp. 1552-1562, 2000.

Tesseur et al., "Expression of Human Apolipoprotein E4 in Neurons Causes Hyperphosphorylation of Protein Tau in the Brains of Transgenic Mice," *American Journal of Pathology*, vol. 156, pp. 951-964, 2000.

Vandesompele et al., "Accurate normalization of real-time quantitative RT-PCR data by geometric averaging of multiple internal control genes," *Genome Biology*, 3(7):research0034.1-0034.11, 2002 (12 pages).

Wong et al., "From Monoamines to Genomic Targets: A Paradigm Shift for Drug Discovery in Depression," *Nature Reviews Drug Discovery*, vol. 3, pp. 136-151, Feb. 2004.

Yao et al., "PAd-shRNA-PTN reduces pleiotrophin of pancrestic cancer cells and inhibits neurite outgrowth of DRG," *World Journal of Gastroenterology*, vol. 17, No. 21, pp. 2667-2673, 2011.

The Human Protein Atlas, "Tissue expression of PTN—Summary," www.proteinatlas.org/ENSG00000105894-PTN/tissue, 2 pages, retrieved on Jan. 27, 2016.

* cited by examiner

FIG. 1A

Characteristics and toxicological data of individual depressed suicide victims and patients with major depression

| Code | Sex | Age (years) | PMD (h) | Toxicology | Affymetrix | RT-PCR | Western blot |
|---|---|---|---|---|---|---|---|
| 1 | F | 73 | 18 | Lithium (600 mg), Benzodiazepines | | X | X |
| 2 | M | 73 | 60 | Citalopram (0.1 µg/ml) | | X | X |
| 3 | M | 65 | 30 | Clomipramine (0.17 µg/ml), ethanol 2 g/l; Otros | | X | |
| 4 | F | 64 | 27 | Miansenn (30 mg), Benzodiazepines, Citalopram | | X | X |
| 5 | F | 56 | 23 | Drug Free | X | X | X |
| 6 | F | 85 | 9 | Sertraline (50 mg), Zolpidem, Benzodiazepines | | X | X |
| 7 | F | 56 | 24 | Zuclopenthixol | X | X | X |
| 8 | M | 76 | 27 | Venlafaxine (150 mg), Norvenlafaxine | | X | |
| 9 | F | 71 | 19 | Theophylline, Salicylic Acid | | X | X |
| 10 | F | 68 | 25 | Sertraline | | X | |
| 11 | F | 35 | 39 | Antibiotics | | X | |
| 12 | F | 73 | 49 | Drug Free | X | X | |
| 13 | F | 64 | 25 | Citalopram (0.05 µg/ml) | | X | X |
| 14 | M | 52 | 6 | Drug Free | | X | X |
| 15 | F | 58 | 24 | Citalopram (0.25 µg/ml) | | X | X |
| 16 | F | 78 | 48 | Citalopram | X | X | X |
| 17 | F | 37 | 3 | Drug Free | | X | X |
| 18 | F | 16 | 11 | Drug Free | | X | X |
| 19 | F | 44 | 3 | Benzodiazepines, fluoxetine | | X | X |
| 20 | F | 68 | 19 | Benzodiazepines | X | X | |
| 21 | F | 73 | 17 | Drug Free | | | X |
| 22 | F | 79 | 13 | Drug Free | | | X |
| 23 | M | 66 | 23 | Clomipramine, Tetrahydrocannabinol | | | X |
| 24 | F | 35 | 23 | Drug Free | | | X |
| 25 | M | 78 | 22 | Drug Free | | | X |
| 26 | F | 64 | 12 | Citalopram (0.06 µg/ml) | | | X |
| 27 | M | 43 | 34 | Citalopram, nordiazepam | | | X |
| 28 | F | 83 | 23 | Venlafaxine, mirtazapine, quetiapine, lorazepam, midazolam, paracetamol | | | X |
| 29 | F | 75 | 21 | Citalopram, diazepam | | | X |

FIG. 1B

Characteristics and toxicological data of individual Control Subjects

| Code | Sex | Age (years) | PMD (h) | Toxicology | Affymetrix | RT-PCR | Western blot |
|---|---|---|---|---|---|---|---|
| 1 | F | 73 | 38 | No available | | X | X |
| 2 | M | 73 | 50 | Drug Free | | X | X |
| 3 | M | 89 | 23 | Drug Free | | X | X |
| 4 | F | 65 | 27 | CoHb/Hb 45% | | X | |
| 5 | F | 59 | 25 | Nortriptyline, amitripyline | | X | |
| 6 | F | 89 | 39 | No available | | X | |
| 7 | F | 52 | 26 | Drug Free | X | X | X |
| 8 | F | 75 | 39 | Atropine, Lidocaine | X | | |
| 9 | M | 76 | 26 | Drug Free | | X | X |
| 10 | F | 69 | 19 | Verapamil (0.1 μg/ml) | | X | X |
| 11 | F | 68 | 38 | Salicylic Acid | | X | |
| 12 | F | 36 | 25 | Drug Free | | X | X |
| 13 | F | 72 | 40 | Digoxina, Furosemida, Glibenclamida | | X | |
| 14 | F | 87 | 34 | Drug Free | | X | X |
| 15 | M | 52 | 14 | Ethanol (0.83g/l) | | X | X |
| 16 | F | 59 | 38 | Ethanol (0.2g/l) | | X | X |
| 17 | F | 76 | 30 | No available | X | X | |
| 18 | F | 35 | 22 | Drug Free | | X | X |
| 19 | F | 16 | 15 | Drug Free | | X | X |
| 20 | F | 43 | 16 | Drug Free | | X | X |
| 21 | F | 68 | 16 | Drug Free | X | X | X |
| 22 | F | 59 | 22 | Drug Free | X | | |
| 23 | F | 71 | 23 | No available | | | X |
| 24 | F | 82 | 16 | Paracetamol, furosemide, amiodarone | | | X |
| 25 | M | 89 | 33 | No available | | | X |
| 26 | F | 35 | 17 | Drug Free | | | X |
| 27 | M | 76 | 39 | Drug Free | | | X |
| 28 | F | 57 | 4 | Drug Free | | | X |
| 29 | M | 44 | 21 | Drug Free | | | X |
| 30 | F | 64 | 21 | Lidocaine, atropine | | | X |
| 31 | F | 74 | 19 | Paracetamol | | | X |

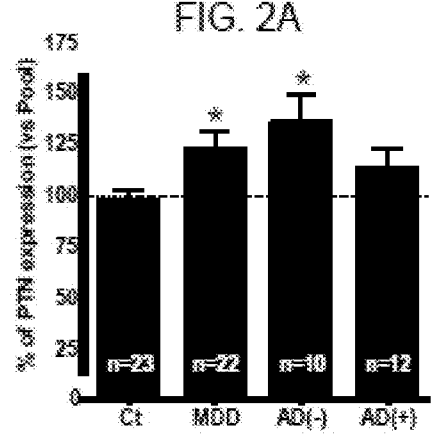
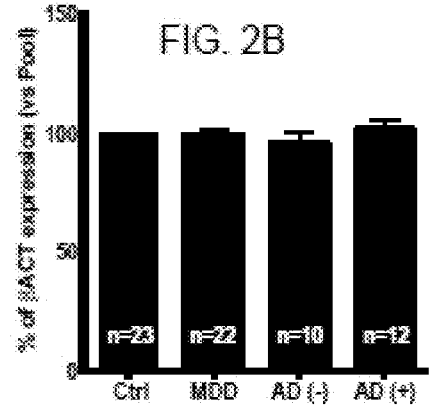
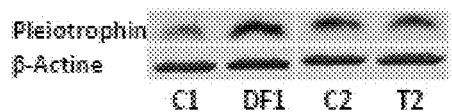
FIG. 2C

Figure 4

| | WT176 | WT177 | WT196 | TG178 | TG180 | TG195 | WT average | TG average | ratio TG/WT |
|---|---|---|---|---|---|---|---|---|---|
| aCA1 | 0,253 | 0,355 | 0,312 | 0,682 | 1,004 | 0,661 | 0,307 | 0,782 | 2,551 |
| aCA3 | 0,121 | 0,111 | 0,093 | 0,535 | 0,328 | 0,512 | 0,109 | 0,458 | 4,220 |
| aDG | 0,137 | 0,113 | 0,105 | 0,239 | 0,341 | 0,312 | 0,119 | 0,297 | 2,508 |
| aCx | 0,310 | 0,228 | 0,271 | 0,580 | 0,840 | 0,606 | 0,270 | 0,675 | 2,506 |
| aCPu | nd | nd | nd | nd | nd | nd | nd | nd | --- |
| aAmy | nd | nd | nd | nd | nd | nd | nd | nd | --- |
| aRt | nd | nd | nd | nd | nd | nd | nd | nd | --- |
| mCA1 | 0,236 | 0,484 | 0,320 | 0,963 | 0,939 | 0,859 | 0,347 | 0,920 | 2,653 |
| mCA3 | 0,105 | 0,107 | 0,134 | 0,850 | 0,778 | 0,569 | 0,115 | 0,733 | 6,355 |
| mDG | 0,125 | 0,100 | 0,106 | 0,265 | 0,306 | 0,229 | 0,110 | 0,267 | 2,418 |
| mCx | 0,239 | 0,231 | 0,260 | 0,594 | 0,812 | 0,600 | 0,244 | 0,669 | 2,746 |
| mCPu | nd | nd | nd | nd | nd | nd | nd | nd | --- |
| mRt | nd | nd | nd | nd | nd | nd | nd | nd | --- |
| pCA1 | 0,327 | 0,236 | 0,383 | 0,888 | 0,919 | 0,660 | 0,315 | 0,822 | 2,606 |
| pCA3 | 0,128 | 0,094 | 0,504 | 0,704 | 1,140 | 0,579 | 0,242 | 0,808 | 3,337 |
| pDG | 0,129 | 0,090 | 0,100 | 0,198 | 0,303 | 0,188 | 0,106 | 0,229 | 2,164 |
| pCx | 0,281 | 0,210 | 0,202 | 0,514 | 0,694 | 0,416 | 0,231 | 0,541 | 2,345 |
| PK | 0,162 | 0,156 | 0,199 | 0,191 | 0,181 | 0,147 | 0,172 | 0,173 | 1,004 |
| GR | 0,210 | 0,189 | 0,290 | 0,399 | 0,205 | 0,200 | 0,230 | 0,268 | 1,168 |

Figure 6

|  | WT | TG |
|---|---|---|
| Excitation | - | 62% |
| Fear response to touch | 15-20% | 68% |
| Jumping response to touch | 15-30% | 38% |
| Vocalization to touch | - | 39% |
| Aggressiveness | - | 15% |
| Tremor | - | 15% |
| Motor tics | - | 15% |
| Increased respiratory rate | - | 23% |
| Ptosis | - | 7,7% |

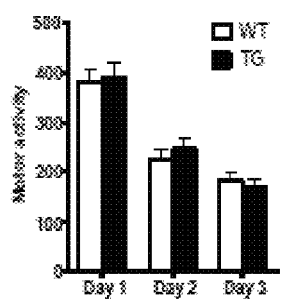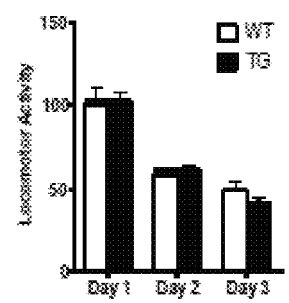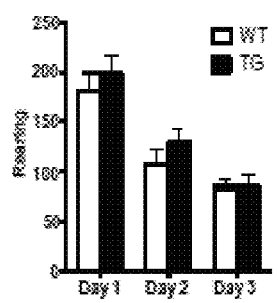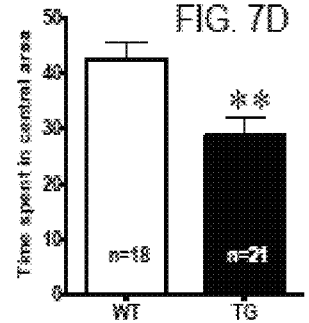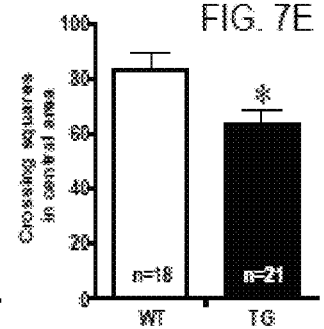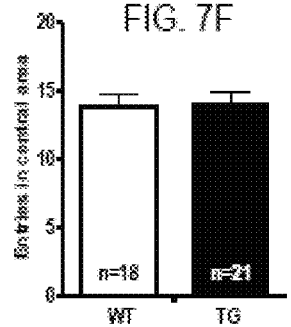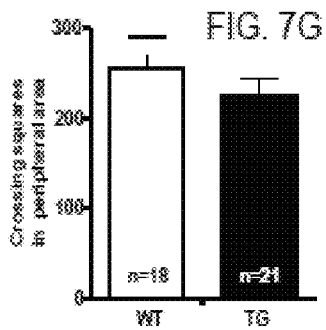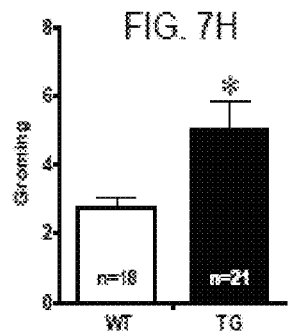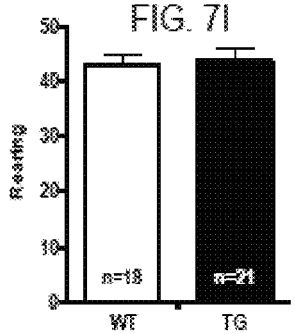

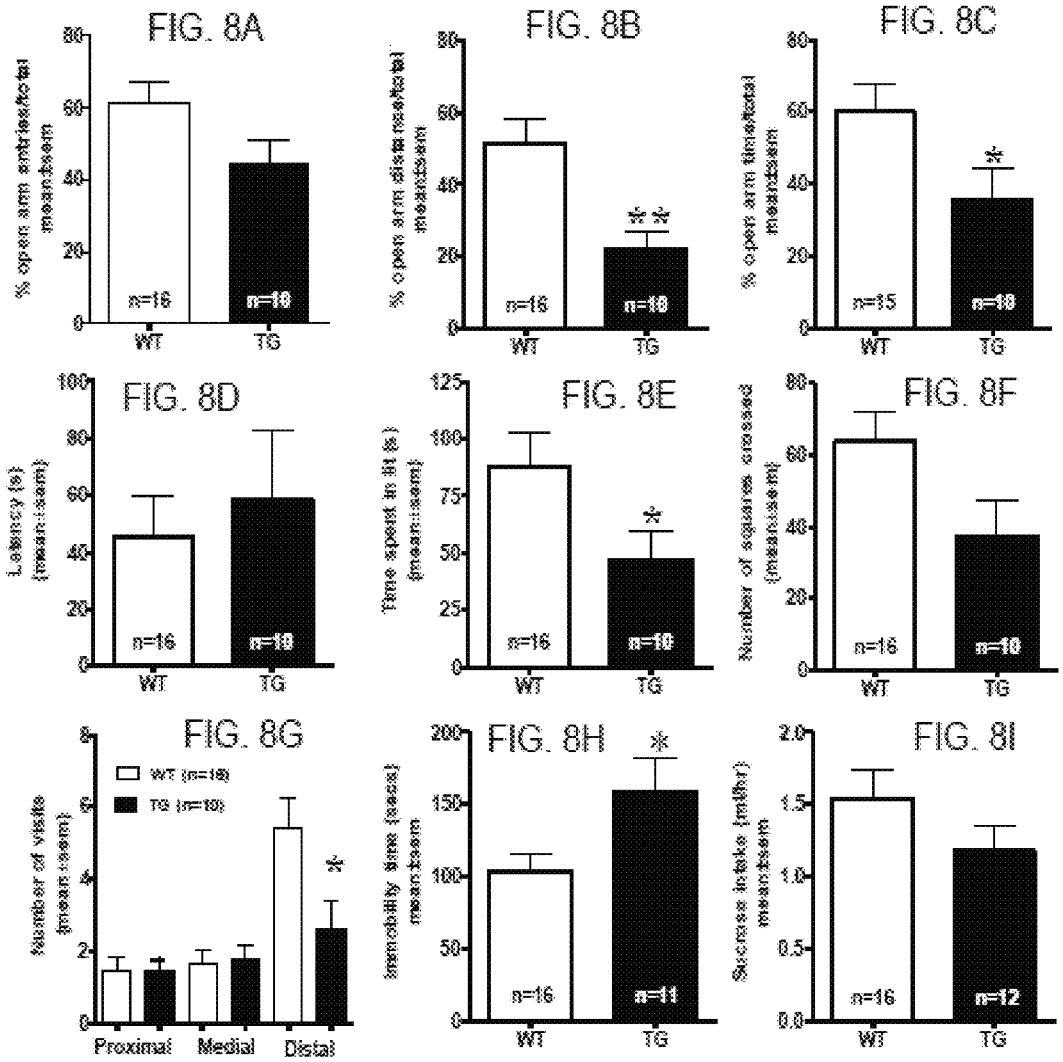

Figure 10 shows the mouse (mouse musculus) PTN cDNA sequence avalaible under NCBI Accession N° BC061695.1 [GI:38197284] (SEQ ID NO: 1).

```
   1  cggcagggtg tagttgagtg aaggcaggat caggttcccc gcctacccgt ccaaatatcc
  61  cgccaaggaa gccccagagc acaagaaaac ccaaagtgga gagagggaa gaaagaaagc
 121  actgagtcat ccatccagaa gggggagag cagagcgcag ccgcccaggc aggagcatca
 181  gccagcgata cctggagtct gcagaaacct cgcccgcact ttgcaacaaa ggcagccagc
 241  tagtcagcga ggacctctgc aagccaaaaa atgtcgtccc agcaatatca gcagcaacgt
 301  agaaaatttg cagctgcctt cctggcattg attttcatct tggcagctgt ggacactgct
 361  gaggccggga agaaagagaa acctgaaaaa aaggtgaaaa agtctgactg tggagaatgg
 421  cagtggagtg tgtgcgtgcc taccagcggg gactgtgat tgggcacccg ggagggcact
 481  cgcactggcg ccgagtgcaa acagaccatg aagactcaga gatgtaagat cccttgcaac
 541  tggaagaagc agtttggagc tgagtgcaag taccagttcc aggcttgggg agaatgtgac
 601  ctcaataccg ccttgaagac cagaactggc agcctgaagc gagctctgca caatgctgac
 661  tgtcagaaaa ctgtcaccat ctccaagccc tgtggcaagc tcaccaagcc caagcctcaa
 721  gcggagtcaa agaagaagaa aaaggaaggc aagaaacagg agaagatgct ggattaaaag
 781  acgccaccgt ctgtggacca ggaaaaggc atcagcaaac aggatcagtt aattattcca
 841  tttataccta ctgtaggctt tttattcaac agttatctgt agcttaagta catgataggc
 901  aaaaacaaag agaaaagaaa tgttttgta gtagtggttt ttttgttttt gttttgttt
 961  ttgttttttt taatgtatac catagtacca gtagggctt ataataaagg attgtaatac
1021  tatttaggaa gttgaactct gtagtacata ataggaggta ggattgaggt aagttttttg
1081  gtgttgttat tttgttttgt ttcattttgg tttggtttgg tttttgaagt tatgtgatat
1141  ttcacattta aatcttttt cttttttaca tgttttctct tgtgcatcaa tttaaatgtt
1201  acaaccatgt aaactactc tcttgttaga tagattttca cctagacttt ttttcccaaa
1261  tcagaaaaaa aatacacact aaataaagca gcaataaat ataatcatt ctattggaga
1321  gaaatgcatt gttttctgcc agtggatatt ttctttgaaa gtttgcagac tgagaggaga
1381  gaggcagagc aacgatgtag tgaaatgttg atctttgttt ttttttttt tttaagataa
1441  gattgaaaca tgaaatcctt tcacttggc agaaaaacat ttgttttctt gatgaaatta
1501  tttttacatc tgaggaaaaa aatctaggaa aataaaacaa gtgatgctga attaaaaaaa
1561  aaaaaaaaa aaaaaaaaa aaaaaaaaa aaaaaaaaa aaa
```

Figure 11 shows the mouse (*Mus musculus*) PTN predicted translated sequence. The mature form of the protein is residues 33-168 available under NCBI Accession No. NM_008973 [GI:118130571] (SEQ ID NO 2).

MSSQQYQQQRRKFAAAFLALIFILAAVDTAEAGKKEKPEKKVKKSDCGEWQWSVCVPTS

GDCGLGTREGTRTGAECKQTMKTQRCKIPCNWKKQFGAECKYQFQAWGECDLNTALKTR

TGSLKRALHNADCQKTVTISKPCGKLTKPKPQAESKKKKEGKKQEKMLD

Figure 12 shows the human Pleiotrophin (PTN) cDNA sequence available under NCBI Accession No. BC005916.1 [GI:13543514] (SEQ ID NO: 3).

```
1    ctctccctcc ctcgcccagc cttcgtcctc ctggcccgct cctctcatcc ctcccattct
61   ccatttccct tccgttccct ccctgtcagg gcgtaattga gtcaaaggca ggatcaggtt
121  cccgccttc  cagtccaaaa atcccgccaa gagagcccca gagcagagga aaatccaaag
181  tggagagagg ggaagaaaga gaccagtgag tcatccgtcc agaaggcggg gagagcagca
241  gcggcccaag caggagctgc agcgagccgg gtacctggac tcagcggtag caacctcgcc
301  ccttgcaaca aaggcagact gagcgccaga gaggacgttt ccaactcaaa aatgcaggct
361  caacagtacc agcagcagcg tcgaaaattt gcagctgcct tcttggcatt cattttcata
421  ctggcagctg tggatactgc tgaagcaggg aagaagaga  accagaaaa  aaaagtgaag
481  aagtctgact gtggagaatg gcagtggagt gtgtgtgtgc ccaccagtgg agactgtggg
541  ctgggcacac gggagggcac tcggactgga gctgagtgca agcaaaccat gaagacccag
601  agatgtaaga tccctgcaa  ctggaagaag caatttggcg cggagtgcaa ataccagttc
661  caggcctggg gagaatgtga cctgaacaca gccctgaaga ccagaactgg aagtctgaag
721  cgagccctgc acaatgccga atgccagaag actgtcacca tctccaagcc ctgtggcaaa
781  ctgaccaagc ccaaacctca agcagaatct aagaagaaga aaaaggaagg caagaaacag
841  gagaagatgc tggattaaaa gatgtcacct gtggaacata aaaaggacat cagcaaacag
901  gatcagttaa ctattgcatt tatatgtacc gtaggcttg  tattcaaaaa ttatctatag
961  ctaagtacac aataagcaaa aacaaaaga  aagaaaatt  tttgtagtag cgttttttaa
1021 atgtatacta tagtaccagt aggggcttat aataaggac  tgtaatctta tttaggaagt
1081 tgacttatag tacatgataa atgatagaca attgaggtaa gttttttgaa attatgtgac
1141 attttacatt aaatttttt  tacattttt  gggcagcaat ttaaatgtta tgactatgta
1201 aactacttct cttgttaggt aatttttttc acctagattt tttccaat   tgagaaaat
1261 atatactaaa caaaaaaaaa aaaaaaaaa  aaaaaaaaa
```

Figure 13 shows the human PTN amino acid sequence available under Uniprot Accession No. P21246, version 1, 1 May 1991. The mature form of the protein is residues 33-168 available (SEQ ID NO: 4).

MQAQQYQQQRRKFAAAFLAFIFILAAVDTAE<u>AGKKEKPEKKVKKSDCGEWQWSVCVPTS</u>
<u>GDCGLGTREGTRTGAECKQTMKTQRCKIPCNWKKQFGAECKYQFQAWGECDLNTALKTR</u>
<u>TGSLKRALHNAECQKTVTISKPCGKLTKPKPQAESKKKKKEGKKQEKMLD</u>

Figure 14A shows the acceptor vector pTSC-a2 which contained the regulatory regions responsible for tissue specific expression of the mouse (*Mus musculus*) THYmocyte differentiation antigen 1 gene (Thy-1) sequence (SEQ ID NO: 5).

```
1    tcgaggtcct tcctctgcag aggtcttgct tctcccggtc agctgactcc ctcccaagt
61   ccttcaaata tctcagaaca tggggagaaa cggggacctt gtccctccta aggaacccca
121  gtgctgcatg ccatcatccc cccaccctc gcccccaccc ccgccacttc tccctccatg
181  cataccacta gctgtcattt tgtactctgt atttattcca gggctgcttc tgattattta
241  gtttgttctt tccctggaga cctgttagaa cataagggcg tatggtgggt agggaggca
301  ggatatcagt ccctggggcg agttcctccc tgccaaccaa gccagatgcc tgaaagagat
361  atggatgagg gaagttggac tgtgcctgta cctggtacag tcatactctg ttgaaagaat
421  catcggggag ggggggggc tcaagagggt ggagctctgc tgagccttg tggaccatcc
481  aatgaggatg agggcttaga ttctaccagg tcattctcag ccaccacaca caagcgctct
541  gccatcactg aagaagcccc ctaggctct tgggccaggg cacactcagt aaagatgcag
601  gttcagtcag ggaatgatgg ggaaggggt aggaggtggg ggaggatca cccctcctc
661  taaaacacga gcctgctgtc tccaaaggcc tctgcctgta gtgagggtgg cagaagaaga
721  caaggagcca gaactctgac tccaggatct aagtccgtgc aggaaggga tcctagaacc
781  atctggttgg acccagctta ccaagggaga gccttattc cttctttccc ttgcccctct
841  gtgccagccc ctcttgctgt ccctgatccc ccagacagcg agagtcttgc aacctgcctc
901  ttccaagacc tcctaatctc aggggcaggc ggtggagtga gatccggcgt gcacactttt
961  tggaagatag ctttcccaag gatcctctcc cccactggca gtctgcctg tcccatcacc
1021 atgtataata ccaccactgc tacagcatct caccgaggaa gaaaatgcac aataaaacca
1081 agcctctgga gtgtgtcctg gtgtctgtct cttctgtgtc ctggcgtctg tctcttctgt
1141 gttcttcaag gtcagaaaca aaaaccacac acttcaacct gatggctcgg ctgagacttc
1201 tgtgtgagaa ggtccaacca gactctgggt acccggccc tcctattcc cttgcctcct
1261 gtctcccgct tttatagctc cctatgctgg gcttctctgg agagtgaaat ctttgcccaa
1321 atcaatgcgc attctctctg ctgagtcatc tggcgacagc agttgagttc acccgccaac
1381 acatggcccc agctatgtag ccgaaccctg gtctggaag tgccagggac tttgtgcata
1441 agtatgtacc atgcccttt ttcacagtcc tagctctgca gaagtgcagc ctgaaggcct
1501 gtctgctgag aggacatgcc ctggagccct gaaacaggca cagtggagg aggaacggag
1561 gatgacaggc atcaggccct cagtccaaaa gcaaccactt gagaatgggc tggagtacga
1621 aacatgggggt cccgtccctg gatcctcct caaagagtaa taagtaaaat ataaacaggt
1681 acccaggcc gttctgggtt tgggttgtaa tgggatccat ttgcagagaa ctattgagac
1741 agcccagccg tactgtgaca ggcaatgtgg gggaggaggt tgaatcactt ggtatttagc
1801 atgaatagaa taattccctg aacatttttc ttaaacatcc atatctaaat taccaccact
1861 cgctcccagt cttcctgcct ttgcgccagc ctcctgtctg gccatgcctg aagaaggctg
1921 gagaagccac ccacctcagg ccatgacact gccagccact tggcaggtgc agccaaacct
1981 gagctgtccc agaaagggac attctcaaga cccaggcacc ctgatcagca ctgacttgga
2041 gctacaagtg tcatgccaga aaagtctcta agaaaaccctt tcagggaaa aggggtgac
2101 tcaacaccgg gcaagtttgg gaagcccac ccttcgagtg atggaagagc agataggaag
2161 cctcagaaga gagacaccgg cacccaggta acgttcctca tgtggtctct gtcacactag
```

Figure 14B

```
2221 gtgctcttcc ctggacatct ccgtgaccac actctcagtt cttagggaga tgcgggtgct
2281 ctctgaggct atctcagagt tgcagattct gaggcctaga gtgactacag tcagcctagg
2341 aagccacaga ggactgtgga ccaggagggc agaagaggag aagggaagaa aaaccatcag
2401 ataggacttg caatgaaact aacccaagac aatcataatg cagacaggaa tgttaaaggc
2461 gttcagcagc tggccatgac acccatctgt ccctctggcc aagtcagcaa gcctggaaga
2521 cctgggactc ctgcccatat gtcctaagct ccccacccac ccactcgttc actgtcctta
2581 ttctctctct accttcagcc acttagtttc ctaccttaag tcctagaatt gatcctggcg
2641 taatagcgaa gaggcccgca ccgatcgccc ttcccaacag ttgcgcagcc tgaatggcga
2701 atggcgcctg atgcggtatt ttctccttac gcatctgtgc ggtatttcac accgcatatg
2761 gtgcactctc agtacaatct gctctgatgc cgcatagtta agccagcccc gacacccgcc
2821 aacacccgct gacgcgccct gacgggcttg tctgctcccg gcatccgctt acagacaagc
2881 tgtgaccgtc tccgggagct gcatgtgtca gaggttttca ccgtcatcac cgaaacgcgc
2941 gagacgaaag gcctcgtga tacgcctatt tttataggtt aatgtcatga taataatggt
3001 ttcttagacg tcaggtggca cttttcgggg aaatgtgcgc ggaaccccta tttgtttatt
3061 tttctaaata cattcaaata tgtatccgct catgagacaa taaccctgat aaatgcttca
3121 ataatattga aaaaggaaga gtatgagtat tcaacatttc cgtgtcgccc ttattccctt
3181 ttttgcggca ttttgccttc ctgtttttgc tcacccagaa acgctggtga agtaaaaga
3241 tgctgaagat cagttgggtg cacgagtggg ttacatcgaa ctggatctca acagcggtaa
3301 gatccttgag agttttcgcc ccgaagaacg ttttccaatg atgagcactt taaagttct
3361 gctatgtggc gcggtattat cccgtattga cgccgggcaa gagcaactcg gtcgccgcat
3421 acactattct cagaatgact tggttgagta ctcaccagtc acagaaaagc atcttacgga
3481 tggcatgaca gtaagagaat tatgcagtgc tgccataacc atgagtgata acactgcggc
3541 caacttactt ctgacaacga tcggaggacc gaaggagcta accgcttttt tgcacaacat
3601 gggggatcat gtaactcgcc ttgatcgttg gaaccggag ctgaatgaag ccataccaaa
3661 cgacgagcgt gacaccacga tgcctgtagc aatggcaaca acgttgcgca aactattaac
3721 tggcgaacta cttactctag cttcccggca acaattaata gactggatgg aggcggataa
3781 agttgcagga ccacttctgc gctcggccct tccggctggc tggtttattg ctgataaatc
3841 tggagccggt gagcgtgggt ctcgcggtat cattgcagca ctggggccag atggtaagcc
3901 ctcccgtatc gtagttatct acacgacggg gagtcaggca actatggatg aacgaaatag
3961 acagatcgct gagataggtg cctcactgat taagcattgg taactgtcag accaagttta
4021 ctcatatata ctttagattg atttaaaact tcattttaa tttaaaagga tctaggtgaa
4081 gatccttttt gataatctca tgaccaaaat cccttaacgt gagttttcgt tccactgagc
4141 gtcagacccc gtagaaaaga tcaaaggatc ttcttgagat cctttttttc tgcgcgtaat
4201 ctgctgcttg caaacaaaaa aaccaccgct accagcggtg gtttgtttgc cggatcaaga
4261 gctaccaact ctttttccga aggtaactgg cttcagcaga gcgcagatac caaatactgt
4321 ccttctagtg tagccgtagt taggccacca cttcaagaac tctgtagcac cgcctacata
4381 cctcgctctg ctaatcctgt taccagtggc tgctgccagt ggcgataagt cgtgtcttac
4441 cgggttggac tcaagacgat agttaccgga taaggcgcag cggtcgggct gaacggggg
4501 ttcgtgcaca cagcccagct tggagcgaac gacctacacc gaactgagat acctacagcg
4561 tgagcattga gaaagcgcca cgcttcccga agggagaaag gcggacaggt atccggtaag
4621 cggcagggtc ggaacaggag agcgcacgag ggagcttcca gggggaaacg cctggtatct
```

Figure 14C

```
4681 ttatagtcct gtcgggtttc gccacctctg acttgagcgt cgattttgt gatgctcgtc
4741 aggggggcgg agcctatgga aaaacgccag caacgcggcc ttttacggt tcctggcctt
4801 ttgctggcct tttgctcaca tgttctttcc tgcgttatcc cctgattctg tggataaccg
4861 tattaccgcc tttgagtgag ctgataccgc tcgccgcagc cgaacgaccg agcgcagcga
4921 gtcagtgagc gaggaagcgg aagagcgccc aatacgcaaa ccgcctctcc ccgcgcgttg
4981 gccgattcat taatgcagga tcgcggccgg ccgcgatccc cgggcgagct cgaattcgct
5041 agccgatcgg aattccgatc ggctagcgaa ttcagagacc gggaaccaaa ctagccttta
5101 aaaacataa gtacaggagc cagcaagatg gctcagtggg taaaggtgcc taccagcaag
5161 cctgacagcc tgagttcagt cccacgaac tacgtggtag gagaggacca accaactctg
5221 gaaatctgtt ctgcaaacac atgctcacac acacacacac aaatagtata acaatttta
5281 aatttcattt aaaaataatt tgtaaacaaa atcattagca caggttttag aaagagcctc
5341 ttggtgacat caagttgatg ctgtagatgg ggtatcattc ctgaggaccc aaaaccgggt
5401 ctcagccttt cccccattctg agagttctct cttttctcag ccactagctg aagagtagag
5461 tggctcagca ctgggctctt gagttcccaa gtcctacaac tggtcagcct gactactaac
5521 cagccatgaa gaaacaagga gtggatgggc tgagtctgct gggatgggag tggagttagt
5581 aagtggccat ggatgtaatg accccagcaa tgctggctag aaggcatgcc tcctttcctt
5641 gtctggagac ggaacgggag ggatcatctt gtactcacag aagggagaac attctagctg
5701 gttgggccaa aatgtgcaag ttcacctgga ggtggtggtg catgcttta actccagtac
5761 tcaggaggca gggccaggtg gatctctgtg agttcaagac cagcctgcac tatggagaga
5821 gttttgggac agccagagtt acacagaaaa atcctggtgg aaaatctgaa agaaagagag
5881 aaagaaagaa agaaagaaag gaagaaagaa agaaagagtg gcaggcaggc aggcaggagg
5941 aaggaaggaa ggaaggaagg aaggaaggaa ggaaggaagg aaaataggtg cgacttcaag
6001 atccggagtt acaagcagaa tgcactgttt ccctaacagg gccaagtgtt ttgagtaact
6061 gaaggtgggc atgatgcctg ggaagcagaa acaagccagg cagatgcacc ccttgccttg
6121 cttccgaagg gctgcagtag catggaaaac atggaaaaca accaatccat tcccttttgct
6181 gatataacag gctccaaagc caaaacctgt cactggaggc tcaagagcag atctccagcc
6241 aagaggcaaa ggaatggggg aagctggagg gcctccctct ggttatccag gcttctgaag
6301 gttcaagcaa agaaagggtt acaaccttaa aaggagagcg tcccggggta tgggtagaag
6361 actgctccac cccgaccccc agggtcccta acgtcttttt cctgggcga gtcagcccaa
6421 tcacaggact gagagtgcct ctttagtagc agcaagccac ttcggacacc caaatggaac
6481 acctccagtc agccctcgcc gaccacccca ccccctccat ccttttcct cagcctccga
6541 ttggctgaat ctagagtccc tccctgctcc ccctctctc ccacccctg gtgaaaactg
6601 cgggcttcag cgctgggtgc agcaactgga ggcgttggcg caccaggagg aggctgcagc
6661 tagggagtc caggtgagag caggccgacg ggagggaccc gcacatgcaa ggaccgcgc
6721 aggcgagga tgcaagcctt cccagctac agttttggga aaggatacya rgcgctcct
6781 atatggggc gcgggaacyt ggggaaagaa ggtgctccca rgtcgaggtg ggagaggaag
6841 gcagtgcggg gtcacgggct ttctccctgc taacggacgc tttcgaagag tgggtgccgg
6901 aggagaacca tgaggaagga catcaaggac atcaaggaca gcctttggtc cccaagctca
6961 gatcgcttta gtggtgcgaa tagagggagg aggtgggtgg caaactggag gggagtcccg
7021 ccgggtgacc tcgtggctgg ctgggtgcgg ggcacgcagg taagaaaacc gcaatgttgc
7081 gggagggac tgggtggcag gcgcggggga ggggaaagct agaaaggatg cgagggagcg
```

Figure 14D

```
7141 gaggggggag ggagcggggg aatctcaact ggtagaggaa agttaaaatg aggaaatagc
7201 atcaggqtgg ggttagccaa gccgggcctc agggaaaggg cgcaaagttt gtctgggtgt
7261 gggcttaggt gggctgggta tgagattcgg ggcgccgaaa acactgctgc gcctctgcca
7321 aatcacgcta ccctgtatc tagttctgct aggcttctcc agcccagcc ccaattcttt
7381 tctcagtgtc cccttccctc ccctgaatct caagcccaca ctccctcctc cataacccac
7441 tgttatcaaa tctaagtcat ttgccaccca acaaccatca ggaggcggaa gcagacggga
7501 ggagtttgag atcaacttgg gctacatcac gagttccaag ctcaccaagg cttcttaagg
7561 agaccttgtc tctaaaatta attaattaat taattaatag tcccctttct ctgccacaga
7621 accttgggat ctggctcctg gtcgcagctc cccccacccc aggctgacat tcactgccat
7681 agccatccg gaaatcctag tctatttccc catggatctt gaactgcaga gagaatggca
7741 gagtggcccg ccctgtgcaa aggatgttcc tagcctaggt ggagctcgcg aactcgaga
7801 ctgtgcctct cttggcaag gacaggctag acagcctgcc ggtgtgttga gctagggcac
7861 tgtgggaag gcagagaacc tgtgcagggc acgcaatgaa cacaggacca gaaaactgca
7921 gccctaggaa cactcaagag ctggccattt gcaagcatct ctggcctccg tgcttctcac
7981 tcatgtccca tgtcttatac aggcctctgt ggcacctcgc ttgcctgatc tcatccctag
8041 ccgttaagct ttctgcatga cttatcactt ggggcataat gctggatacc taccattttc
8101 ttagccccca tcaaaatcct atttgagtgt acggttcgga gaactcctta tttatccggt
8161 aaatgtcttt tactctgctc tcagggagct gaggcaggac attcctgaga tacattggga
8221 gaggaataca gtttcaataa aataataggt tgggtggagg tacatgccta taatgccacc
8281 actcaggaaa tggtggcagc ttcgtgagtt tgaggccaac ccaagaaaca tagtgaaacc
8341 ctgtcagtaa ataagtaagc aagtatttga gtatctacta tatgctaggg ctgacctgga
8401 cattaggggt catcttctga acaaactagt gcttgaggga ggtatttggg gttttttgttt
8461 gtttaatgga tctgaatgag ttccagagac tggctacaca gcgatatgac tgagcttaac
8521 accctaaag catacagtca gaccaattag acaataaaag gtatgtatag cttaccaaat
8581 aaaaaaattg tattttcaag agagtgtctg tctgtgtagc cctggctgtt cttgaactca
8641 ctctgtagac caggctggcc tggaaatcca tctgcctgcc tctgcctctc tgcctctctg
8701 cctctctgcc tctctctctg cctctctctg cctctctctg ccctctctg ccctctctg
8761 ccctctctg ccgccctctg ccttttgccc tctgccctct gttctctggc ctctgccctc
8821 tgccctctgg cctctggcct ctgcctctgc ctcttgagtg ctggaatcaa aggtgtgagc
8881 tctgtaggtc ttaagttcca gaagaaagta atgaagtcac ccagcaggga ggtgctcagg
8941 gacagcacag acacacaccc aggacatagg ctcccacttc cttggctttc tctgagtggc
9001 aaaggacctt aggcagtgtc actccctaag agaaggggat aaagagaggg gctgaggtat
9061 tcatcatgtg ctccgtggat ctcaagccct caaggtaaat ggggacccac ctgtcctacc
9121 agctggctga cctgtagctt tccccaccac agaatccaag tcggaactct tggcacctag
9181 aggatctcga
``` the aetiology of MDD. The monoamine hypotheses of depression, which posits that depression is caused by decreased monoamine function in the brain, originated from early clinical observations. The serendipitous discovery of antidepressants in the 1950s has profoundly inspired this hypothesis of the pathogenesis of depression. The well-known pharmacological effects of antidepressants on presynaptic uptake transporters and degradating enzymes (i.e., MAO) of serotonin and norepinephrine has focused research on causality and treatment of depression on the metabolism of functional biogenic amines and the capacity of their respective receptors to alter intracellular signaling pathways that ultimately induce changes in gene activity. Although these mono amine-based agents are potent antidepressants, and alterations in central monoamine function might contribute marginally to genetic vulnerability, the cause of depression is far from being a simple deficiency of central monoamines. Monoamine oxidase inhibitors and SSRIs produce immediate increases in monoamine transmission, whereas their mood-enhancing properties require weeks of treatment. Conversely, experimental depletion of monoamines can produce a mild reduction in mood in unmedicated depressed patients, but such manipulations do not alter mood in healthy controls. It is now thought that acute increases in the amount of synaptic monoamines induced by antidepressants produce secondary neuroplastic changes that are on a longer timescale and involve transcriptional and translational changes that mediate molecular and cellular plasticity (Krishnan and Nestler, 2008)

SEQUENCE LISTING

<160> NUMBER OF SEQ ID NOS: 11

<210> SEQ ID NO 1
<211> LENGTH: 1603
<212> TYPE: DNA
<213> ORGANISM: Mus musculus

<400> SEQUENCE: 1

```
cggcagggtg tagttgagtg aaggcaggat caggttcccc gcctacccgt ccaaatatcc      60
cgccaaggaa gccccagagc acaagaaaac ccaaagtgga gagagggaa gaaagaaagc     120
actgagtcat ccatccagaa gggggagag cagagcgcag ccgcccaggc aggagcatca     180
gccagcgata cctggagtct gcagaaacct cgcccgcact ttgcaacaaa ggcagccagc     240
tagtcagcga ggacctctgc aagccaaaaa atgtcgtccc agcaatatca gcagcaacgt     300
agaaaatttg cagctgcctt cctggcattg attttcatct tggcagctgt ggacactgct     360
gaggccggga agaaagagaa acctgaaaaa aaggtgaaaa agtctgactg tggagaatgg     420
cagtggagtg tgtgcgtgcc taccagcggg gactgtggat tgggcacccg ggagggcact     480
cgcactggcg ccgagtgcaa acagaccatg aagactcaga gatgtaagat cccttgcaac     540
tggaagaagc agtttggagc tgagtgcaag taccagttcc aggcttgggg agaatgtgac     600
ctcaataccg ccttgaagac cagaactggc agcctgaagc gagctctgca caatgctgac     660
tgtcagaaaa ctgtcaccat ctccaagccc tgtggcaagc tcaccaagcc caagcctcaa     720
gcggagtcaa agaagaagaa aaaggaaggc aagaacagg agaagatgct ggattaaaag     780
acgccaccgt ctgtggacca ggaaaagggc atcagcaaac aggatcagtt aattattcca     840
tttataccta ctgtaggctt tttattcaac agttatctgt agcttaagta catgataggc     900
aaaaacaaag agaaagaaa tgtttttgta gtagtggttt ttttgttttt gttttgttt     960
ttgttttttt taatgtatac catagtacca gtaggggctt ataataaagg attgtaatac    1020
tatttaggaa gttgaactct gtagtacata ataggaggta ggattgaggt aagttttttg    1080
gtgttgttat tttgttttgt ttcattttgg tttggtttgg ttttgaagt tatgtgatat    1140
ttcacattta aatctttttt ctttttaca tgttttctct tgtgcatcaa tttaaatgtt    1200
acaaccatgt aaactacttc tcttgttaga tagattttca cctagacttt ttttcccaaa    1260
tcagaaaaaa aatacacact aaataaagca gcaataaaat ataaatcatt ctattggaga    1320
gaaatgcatt gttttctgcc agtggatatt ttctttgaaa gtttgcagac tgagaggaga    1380
gaggcagagc aacgatgtag tgaaatgttg atctttgttt ttttttttt tttaagtaaa    1440
gattgaaaca tgaaatcctt tcactttggc agaaaaacat ttgttttctt gatgaaatta    1500
tttttacatc tgaggaaaaa aatctaggaa aataaaacaa gtgatgctga attaaaaaaa    1560
aaaaaaaaaa aaaaaaaaaa aaaaaaaaaa aaaaaaaaaa aaa                      1603
```

<210> SEQ ID NO 2
<211> LENGTH: 168
<212> TYPE: PRT
<213> ORGANISM: Mus musculus

<400> SEQUENCE: 2

```
Met Ser Ser Gln Gln Tyr Gln Gln Gln Arg Arg Lys Phe Ala Ala Ala
 1               5                  10                  15

Phe Leu Ala Leu Ile Phe Ile Leu Ala Ala Val Asp Thr Ala Glu Ala
```

```
            20                  25                  30
Gly Lys Lys Glu Lys Pro Glu Lys Val Lys Lys Ser Asp Cys Gly
        35                  40                  45

Glu Trp Gln Trp Ser Val Cys Val Pro Thr Ser Gly Asp Cys Gly Leu
    50                  55                  60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95

Ala Glu Cys Lys Tyr Gln Phe Gln Ala Trp Gly Glu Cys Asp Leu Asn
            100                 105                 110

Thr Ala Leu Lys Thr Arg Thr Gly Ser Leu Lys Arg Ala Leu His Asn
        115                 120                 125

Ala Asp Cys Gln Lys Thr Val Thr Ile Ser Lys Pro Cys Gly Lys Leu
    130                 135                 140

Thr Lys Pro Lys Pro Gln Ala Glu Ser Lys Lys Lys Lys Glu Gly
145                 150                 155                 160

Lys Lys Gln Glu Lys Met Leu Asp
                165

<210> SEQ ID NO 3
<211> LENGTH: 1300
<212> TYPE: DNA
<213> ORGANISM: Homo sapiens

<400> SEQUENCE: 3
ctctccctcc ctcgcccagc cttcgtcctc ctggcccgct cctctcatcc ctcccattct      60
ccatttccct tccgttccct ccctgtcagg gcgtaattga gtcaaaggca ggatcaggtt     120
ccccgccttc cagtccaaaa atcccgccaa gagagcccca gagcagagga aaatccaaag     180
tggagagagg ggaagaaaga gaccagtgag tcatccgtcc agaaggcggg gagagcagca     240
gcggcccaag caggagctgc agcgagccgg gtacctggac tcagcggtag caacctcgcc     300
ccttgcaaca aaggcagact gagcgccaga gaggacgttt ccaactcaaa atgcaggct      360 caacagtacc agcagcagcg tcgaaaattt gcagctgcct tcttggcatt cattttcata     420
ctggcagctg tggatactgc tgaagcaggg aagaaagaga accagaaaaa aaagtgaag      480 aagtctgact gtggagaatg gcagtggagt gtgtgtgtgc ccaccagtgg agactgtggg     540
ctgggcacac gggagggcac tcggactgga gctgagtgca agcaaaccat gaagacccag     600
agatgtaaga tcccctgcaa ctggaagaag caatttggcg cggagtgcaa ataccagttc     660
caggcctggg gagaatgtga cctgaacaca gccctgaaga ccagaactgg aagtctgaag     720
cgagccctgc acaatgccga tgccagaag actgtcacca tctccaagcc tgtggcaaa     780 ctgaccaagc ccaaacctca agcagaatct aagaagaaga aaaggaagg caagaaacag     840 gagaagatgc tggattaaaa gatgtcacct gtggaacata aaaggacat cagcaaacag     900 gatcagttaa ctattgcatt tatatgtacc gtaggctttg tattcaaaaa ttatctatag     960
ctaagtacac aataagcaaa aacaaaaaga aagaaaatt tttgtagtag cgttttttaa    1020
atgtatacta tagtaccagt aggggcttat aataaaggac tgtaatctta tttaggaagt    1080
tgacttatag tacatgataa atgatagaca attgaggtaa gttttttgaa attatgtgac    1140 attttcatt aaattttttt tacatttttt gggcagcaat ttaaatgtta tgactatgta    1200
aactacttct cttgttaggt aatttttttc acctagattt ttttcccaat tgagaaaaat    1260
```

```
atatactaaa caaaaaaaaa aaaaaaaaaa aaaaaaaaa                    1300
```

```
<210> SEQ ID NO 4
<211> LENGTH: 168
<212> TYPE: PRT
<213> ORGANISM: Homo sapiens

<400> SEQUENCE: 4

Met Gln Ala Gln Gln Tyr Gln Gln Arg Arg Lys Phe Ala Ala Ala
1               5                   10                  15

Phe Leu Ala Phe Ile Phe Ile Leu Ala Ala Val Asp Thr Ala Glu Ala
            20                  25                  30

Gly Lys Lys Glu Lys Pro Glu Lys Val Lys Lys Ser Asp Cys Gly
            35                  40                  45

Glu Trp Gln Trp Ser Val Cys Val Pro Thr Ser Gly Asp Cys Gly Leu
 50                  55                  60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95

Ala Glu Cys Lys Tyr Gln Phe Gln Ala Trp Gly Glu Cys Asp Leu Asn
            100                 105                 110

Thr Ala Leu Lys Thr Arg Thr Gly Ser Leu Lys Arg Ala Leu His Asn
        115                 120                 125

Ala Glu Cys Gln Lys Thr Val Thr Ile Ser Lys Pro Cys Gly Lys Leu
    130                 135                 140

Thr Lys Pro Lys Pro Gln Ala Glu Ser Lys Lys Lys Lys Glu Gly
145                 150                 155                 160

Lys Lys Gln Glu Lys Met Leu Asp
                165
```

```
<210> SEQ ID NO 5
<211> LENGTH: 9190
<212> TYPE: DNA
<213> ORGANISM: Artificial sequence
<220> FEATURE:
<223> OTHER INFORMATION: Acceptor vector pTSC-a2

<400> SEQUENCE: 5
tcgaggtcct tcctctgcag aggtcttgct tctcccggtc agctgactcc ctccccaagt    60
ccttcaaata tctcagaaca tggggagaaa cggggacctt gtccctccta aggaacccca   120
gtgctgcatg ccatcatccc ccccaccctc gcccccaccc ccgccacttc tccctccatg   180
cataccacta gctgtcattt tgtactctgt atttattcca gggctgcttc tgattattta   240
gtttgttctt tccctggaga cctgttagaa cataagggcg tatggtgggt aggggaggca   300
ggatatcagt ccctggggcg agttcctccc tgccaaccaa gccagatgcc tgaaagagat   360
atggatgagg gaagttggac tgtgcctgta cctggtacag tcatactctg ttgaaagaat   420
catcggggag gggggggggc tcaagagggt ggagctctgc tgagcctttg tggaccatcc   480
aatgaggatg agggcttaga ttctaccagg tcattctcag ccaccacaca caagcgctct   540
gccatcactg aagaagcccc ctagggctct tgggccaggg cacactcagt aaagatgcag   600
gttcagtcag ggaatgatgg ggaaggggt aggaggtggg ggagggatca cccctcctc   660 taaaacacga gcctgctgtc tccaaaggcc tctgcctgta gtgagggtgg cagaagaaga   720
caaggagcca gaactctgac tccaggatct aagtccgtgc aggaagggga tcctagaacc   780
```

```
atctggttgg acccagctta ccaagggaga gcctttattc cttctttccc ttgcccctct    840
gtgccagccc ctcttgctgt ccctgatccc ccagacagcg agagtcttgc aacctgcctc    900
ttccaagacc tcctaatctc aggggcaggc ggtggagtga gatccggcgt gcacactttt    960
tggaagatag ctttcccaag gatcctctcc cccactggca gctctgcctg tcccatcacc   1020
atgtataata ccaccactgc tacagcatct caccgaggaa gaaaatgcac aataaaacca   1080
agcctctgga gtgtgtcctg gtgtctgtct cttctgtgtc ctggcgtctg tctcttctgt   1140
gttcttcaag gtcagaaaca aaaccacac acttcaacct gatggctcgg ctgagacttc    1200
tgtgtgagaa ggtccaacca gactctgggt accccggccc tccctattcc cttgcctcct   1260
gtctcccgct tttatagctc cctatgctgg gcttctctgg agagtgaaat ctttgcccaa   1320
atcaatgcgc attctctctg ctgagtcatc tggcgacagc agttgagttc acccgccaac   1380
acatgggccc agctatgtag ccgaaccctg gctctggaag tgccagggac tttgtgcata   1440
agtatgtacc atgcccttt tcacagtcc tagctctgca gaagtgcagc ctgaaggcct    1500
gtctgctgag aggacatgcc ctggagccct gaaacaggca cagtgggagg aggaacggag   1560
gatgacaggc atcaggccct cagtccaaaa gcaaccactt gagaatgggc tggagtacga   1620
aacatggggt cccgtccctg gatccctcct caaagagtaa taagtaaaat ataaacaggt   1680
accccaggcc gttctgggtt tgggttgtaa tgggatccat ttgcagagaa ctattgagac   1740
agcccagccg tactgtgaca ggcaatgtgg gggaggaggt tgaatcactt ggtatttagc   1800
atgaatagaa taattccctg aacatttttc ttaaacatcc atatctaaat taccaccact   1860
cgctcccagt cttcctgcct ttgcgccagc ctcctgtctg gccatgcctg aagaaggctg   1920
gagaagccac ccacctcagg ccatgacact gccagccact tggcaggtgc agccaaacct   1980
gagctgtccc agaaagggac attctcaaga cccaggcacc ctgatcagca ctgacttgga   2040
gctacaagtg tcatgccaga aaagtctcta agaaaacctt ttcagggaaa aggggtgac   2100
tcaacaccgg gcaagtttgg gaagcccac ccttcgagtg atggaagagc agatagaag    2160
cctcagaaga gagacaccgg cacccaggta acgttcctca tgtggtctct gtcacactag   2220
gtgctcttcc ctggacatct ccgtgaccac actctcagtt cttagggaga tgcgggtgct   2280
ctctgaggct atctcagagt tgcagattct gaggcctaga gtgactacag tcagcctagg   2340
aagccacaga ggactgtgga ccaggagggc agaagaggag aagggaagaa aaaccatcag   2400
ataggacttg caatgaaact aacccaagac aatcataatg cagacaggaa tgttaaaggc   2460
gttcagcagc tggccatgac acccatctgt ccctctggcc aagtcagcaa gcctggaaga   2520
cctgggactc ctgcccatat gtcctaagct ccccaccac ccactcgttc actgtcctta    2580
ttctctctct accttcagcc acttagtttc ctaccttaag tcctagaatt gatcctggcg   2640
taatagcgaa gaggcccgca ccgatcgccc ttcccaacag ttgcgcagcc tgaatggcga   2700
atggcgcctg atgcggtatt ttctccttac gcatctgtgc ggtatttcac accgcatatg   2760
gtgcactctc agtacaatct gctctgatgc cgcatagtta agccagcccc gacacccgcc   2820
aacacccgct gacgcgccct gacgggcttg tctgctcccg gcatccgctt acagacaagc   2880
tgtgaccgtc tccgggagct gcatgtgtca gaggttttca ccgtcatcac cgaaacgcgc   2940
gagacgaaag gcctcgtga tacgcctatt tttataggtt aatgtcatga taataatggt    3000
ttcttagacg tcaggtggca cttttcgggg aaatgtgcgc ggaacccta tttgtttatt     3060
tttctaaata cattcaaata tgtatccgct catgagacaa taaccctgat aaatgcttca   3120
ataatattga aaaggaaga gtatgagtat tcaacatttc cgtgtcgccc ttattccctt    3180
```

```
ttttgcggca ttttgccttc ctgttttgc  tcacccagaa acgctggtga aagtaaaaga    3240
tgctgaagat cagttgggtg cacgagtggg ttacatcgaa ctggatctca acagcggtaa    3300
gatccttgag agttttcgcc ccgaagaacg ttttccaatg atgagcactt ttaaagttct    3360
gctatgtggc gcggtattat cccgtattga cgccgggcaa gagcaactcg gtcgccgcat    3420
acactattct cagaatgact tggttgagta ctcaccagtc acagaaaagc atcttacgga    3480
tggcatgaca gtaagagaat tatgcagtgc tgccataacc atgagtgata acactgcggc    3540
caacttactt ctgacaacga tcggaggacc gaaggagcta accgcttttt tgcacaacat    3600
gggggatcat gtaactcgcc ttgatcgttg ggaaccggag ctgaatgaag ccataccaaa    3660
cgacgagcgt gacaccacga tgcctgtagc aatggcaaca acgttgcgca aactattaac    3720
tggcgaacta cttactctag cttcccggca acaattaata gactggatgg aggcggataa    3780
agttgcagga ccacttctgc gctcggccct tccggctggc tggtttattg ctgataaatc    3840
tggagccggt gagcgtgggt ctcgcggtat cattgcagca ctggggccag atggtaagcc    3900
ctcccgtatc gtagttatct acacgacggg gagtcaggca actatggatg aacgaaatag    3960
acagatcgct gagataggtg cctcactgat taagcattgg taactgtcag accaagttta    4020
ctcatatata ctttagattg atttaaaact tcatttttaa tttaaaagga tctaggtgaa    4080
gatccttttt gataatctca tgaccaaaat cccttaacgt gagttttcgt tccactgagc    4140
gtcagacccc gtagaaaaga tcaaaggatc ttcttgagat cctttttttc tgcgcgtaat    4200
ctgctgcttg caaacaaaaa aaccaccgct accagcggtg gtttgtttgc cggatcaaga    4260
gctaccaact cttttttccga aggtaactgg cttcagcaga gcgcagatac caaatactgt    4320
ccttctagtg tagccgtagt taggccacca cttcaagaac tctgtagcac cgcctacata    4380
cctcgctctg ctaatcctgt taccagtggc tgctgccagt ggcgataagt cgtgtcttac    4440
cgggttggac tcaagacgat agttaccgga taaggcgcag cggtcgggct gaacgggggg    4500
ttcgtgcaca cagcccagct tggagcgaac gacctacacc gaactgagat acctacagcg    4560
tgagcattga gaaagcgcca cgcttcccga agggagaaag gcggacaggt atccggtaag    4620
cggcagggtc ggaacaggag agcgcacgag ggagcttcca gggggaaacg cctggtatct    4680
ttatagtcct gtcgggtttc gccacctctg acttgagcgt cgatttttgt gatgctcgtc    4740
agggggggcg agcctatgga aaaacgccag caacgcggcc ttttttacggt tcctggcctt    4800 ttgctggcct tttgctcaca tgttcttttcc tgcgttatcc cctgattctg tggataaccg    4860
tattaccgcc tttgagtgag ctgataccgc tcgccgcagc cgaacgaccg agcgcagcga    4920
gtcagtgagc gaggaagcgg aagagcgccc aatacgcaaa ccgcctctcc ccgcgcgttg    4980
gccgattcat taatgcagga tcgcggccgg ccgcgatccc cgggcgagct cgaattcgct    5040
agccgatcgg aattccgatc ggctagcgaa ttcagagacc gggaaccaaa ctagccttta    5100
aaaaacataa gtacaggagc cagcaagatg gctcagtggg taaaggtgcc taccagcaag    5160
cctgacagcc tgagttcagt ccccacgaac tacgtggtag agaggaccca accaactctg    5220
gaaatctgtt ctgcaaacac atgctcacac acacacacac aaatagtata acaattttta    5280
aatttcattt aaaaataatt tgtaaacaaa atcattagca caggttttag aaagagcctc    5340
ttggtgacat caagttgatg ctgtagatgg ggtatcattc ctgaggaccc aaaaccgggt    5400
ctcagccttt ccccattctg agagttctct cttttctcag ccactagctg aagagtagag    5460
tggctcagca ctgggctctt gagttcccaa gtcctacaac tggtcagcct gactactaac    5520
```

```
cagccatgaa gaaacaagga gtggatgggc tgagtctgct gggatgggag tggagttagt    5580
aagtggccat ggatgtaatg accccagcaa tgctggctag aaggcatgcc tcctttcctt    5640
gtctggagac ggaacgggag ggatcatctt gtactcacag aagggagaac attctagctg    5700
gttgggccaa aatgtgcaag ttcacctgga ggtggtggtg catgctttta actccagtac    5760
tcaggaggca gggccaggtg gatctctgtg agttcaagac cagcctgcac tatgagaga     5820
gttttgggac agccagagtt acacagaaaa atcctggtgg aaaatctgaa agaaagagag    5880
aaagaaagaa agaaagaaag gaagaaagaa agaaagagtg gcaggcaggc aggcaggagg    5940
aaggaaggaa ggaaggaagg aaggaaggaa ggaaggaagg aaaataggtg cgacttcaag    6000
atccggagtt acaagcagaa tgcactgttt ccctaacagg gccaagtgtt ttgagtaact    6060
gaaggtgggc atgatgcctg ggaagcagaa acaagccagg cagatgcacc ccttgccttg    6120
cttccgaagg gctgcagtag catggaaaac atggaaaaca accaatccat tccctttgct    6180
gatataacag gctccaaagc caaaacctgt cactggaggc tcaagagcag atctccagcc    6240
aagaggcaaa ggaatggggg aagctggagg gcctccctct ggttatccag gcttctgaag    6300
gttcaagcaa agaaagggtt acaaccttaa aaggagagcg tcccggggta tgggtagaag    6360
actgctccac cccgaccccc agggtcccta accgtctttt cctgggcga gtcagcccaa    6420
tcacaggact gagagtgcct ctttagtagc agcaagccac ttcggacacc caaatggaac    6480
acctccagtc agccctcgcc gaccacccca ccccctccat ccttttccct cagcctccga    6540
ttggctgaat ctagagtccc tccctgctcc ccctctctc cccaccctg gtgaaaactg      6600
cgggcttcag cgctgggtgc agcaactgga ggcgttggcg caccaggagg aggctgcagc    6660
tagggagtc caggtgagag caggccgacg ggagggaccc gcacatgcaa ggaccgccgc     6720
agggcgagga tgcaagcctt ccccagctac agttttggga aaggatacya rggcgctcct    6780
atatgggggc gcgggaacyt ggggaaagaa ggtgctccca rgtcgaggtg ggagaggaag    6840
gcagtgcggg gtcacgggct ttctcccctgc taacggacgc tttcgaagag tgggtgccgg    6900
aggagaacca tgaggaagga catcaaggac atcaaggaca gcctttggtc cccaagctca    6960
gatcgcttta gtggtgcgaa tagagggagg aggtgggtgg caaactggag ggagtccccg    7020
ccgggtgacc tcgtggctgg ctgggtgcgg ggcacgcagg taagaaaacc gcaatgttgc    7080
gggaggggac tgggtggcag cgcgcggggga ggggaaagct agaaaggatg cgagggagcg    7140
gagggggggag ggagcggggg aatctcaact ggtagaggaa agttaaaatg aggaaatagc    7200
atcagggtgg ggttagccaa gccgggcctc agggaaaggg cgcaaagttt gtctgggtgt    7260
gggcttaggt gggctgggta tgagattcgg ggcgccgaaa acactgctgc gcctctgcca    7320
aatcacgcta cccctgtatc tagttctgct aggcttctcc agccccagcc ccaattcttt    7380
tctcagtgtc cccttccctc ccctgaatct caagcccaca ctccctcctc cataacccac    7440
tgttatcaaa tctaagtcat ttgccaccca acaaccatca ggaggcgaa gcagacggga    7500
ggagtttgag atcaacttgg gctacatcac gagttccaag ctcaccaagg cttcttaagg    7560
agaccttgtc tctaaaatta attaattaat taattaatag tccccttttct ctgccacaga   7620
accttgggat ctggctcctg gtcgcagctc ccccacccc aggctgacat tcactgccat     7680
agcccatccg gaaatcctag tctatttccc catggatctt gaactgcaga gagaatggca   7740
gagtggcccg ccctgtgcaa aggatgttcc tagcctaggt ggagctcgcg aactcgsaga   7800
ctgtgcctct cttgggcaag gacaggctag acagcctgcc ggtgtgttga gctagggcac   7860
tgtggggaag gcagagaacc tgtgcagggc acgcaatgaa cacaggacca gaaaactgca   7920
```

```
gccctaggaa cactcaagag ctggccattt gcaagcatct ctggcctccg tgcttctcac    7980
tcatgtccca tgtcttatac aggcctctgt ggcacctcgc ttgcctgatc tcatccctag    8040
ccgttaagct ttctgcatga cttatcactt ggggcataat gctggatacc taccattttc    8100
ttagacccca tcaaaatcct atttgagtgt acggttcgga gaactcctta tttatccggt    8160
aaatgtcttt tactctgctc tcagggagct gaggcaggac attcctgaga tacattggga    8220
gaggaataca gtttcaataa aataataggt tgggtggagg tacatgccta taatgccacc    8280
actcaggaaa tggtggcagc ttcgtgagtt tgaggccaac ccagaaaaca tagtgaaacc    8340
ctgtcagtaa ataagtaagc aagtatttga gtatctacta tatgctaggg ctgacctgga    8400 cattagggt catcttctga acaaactagt gcttgaggga ggtatttggg gttttgttt     8460 gtttaatgga tctgaatgag ttccagagac tggctacaca gcgatatgac tgagcttaac    8520 accctaaag catacagtca gaccaattag acaataaaag gtatgtatag cttaccaaat    8580
aaaaaaattg tattttcaag agagtgtctg tctgtgtagc cctggctgtt cttgaactca    8640
ctctgtagac caggctggcc tggaaatcca tctgcctgcc tctgcctctc tgcctctctg    8700
cctctctgcc tctctctctg cctctctctg cctctctctg cccctctctg cccctctctg    8760
cccctctctg ccgccctctg ccttttgccc tctgccctct gttctctggc ctctgccctc    8820
tgccctctgg cctctggcct ctgcctctgc ctcttgagtg ctggaatcaa aggtgtgagc    8880
tctgtaggtc ttaagttcca gaagaaagta atgaagtcac ccagcaggga ggtgctcagg    8940
gacagcacag acacacaccc aggacatagg ctcccacttc cttggctttc tctgagtggc    9000 aaaggaccttt aggcagtgtc actccctaag agaagggat aaagagaggg gctgaggtat    9060
tcatcatgtg ctccgtggat ctcaagcct caaggtaaat ggggaccac ctgtcctacc      9120 agctggctga cctgtagctt tccccaccac agaatccaag tcggaactct tggcacctag    9180
aggatctcga                                                           9190
```

```
<210> SEQ ID NO 6
<211> LENGTH: 47
<212> TYPE: DNA
<213> ORGANISM: Artificial sequence
<220> FEATURE:
<223> OTHER INFORMATION: Oligonucleotide

<400> SEQUENCE: 6
agtgtccaca gctgccaaga tgaaaatcaa tgcaggaagg cagctgc                 47

<210> SEQ ID NO 7
<211> LENGTH: 47
<212> TYPE: DNA
<213> ORGANISM: Artificial sequence
<220> FEATURE:
<223> OTHER INFORMATION: Oligonucleotide

<400> SEQUENCE: 7
actcggcgcc agtgcgagtg ccctcccggg tgcccaatcc acagtcc                 47

<210> SEQ ID NO 8
<211> LENGTH: 47
<212> TYPE: DNA
<213> ORGANISM: Artificial sequence
<220> FEATURE:
<223> OTHER INFORMATION: Oligonucleotide

<400> SEQUENCE: 8
```

```
aggcttgggc ttggtgagct tgccacaggg cttggagatg gtgacag                    47
```

```
<210> SEQ ID NO 9
<211> LENGTH: 4
<212> TYPE: PRT
<213> ORGANISM: Homo sapiens

<400> SEQUENCE: 9

Asp Glu Ala Asp
1

<210> SEQ ID NO 10
<211> LENGTH: 168
<212> TYPE: PRT
<213> ORGANISM: Homo sapiens

<400> SEQUENCE: 10

Met Gln Ala Gln Gln Tyr Gln Gln Gln Arg Arg Lys Phe Ala Ala Ala
1               5                   10                  15

Phe Leu Ala Phe Ile Phe Ile Leu Ala Ala Val Asp Thr Ala Glu Ala
            20                  25                  30

Gly Lys Lys Glu Lys Pro Glu Lys Val Lys Lys Ser Asp Cys Gly
        35                  40                  45

Glu Trp Gln Trp Ser Val Cys Val Pro Thr Ser Gly Asp Cys Gly Leu
 50                  55                  60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95

Ala Glu Cys Lys Tyr Gln Phe Gln Ala Trp Gly Glu Cys Asp Leu Asn
            100                 105                 110

Thr Ala Leu Lys Thr Arg Thr Gly Ser Leu Lys Arg Ala Leu His Asn
        115                 120                 125

Ala Glu Cys Gln Lys Thr Val Thr Ile Ser Lys Pro Cys Gly Lys Leu
    130                 135                 140

Thr Lys Pro Lys Pro Gln Ala Glu Ser Lys Lys Lys Lys Glu Gly
145                 150                 155                 160

Lys Lys Gln Glu Lys Met Leu Asp
                165

<210> SEQ ID NO 11
<211> LENGTH: 168
<212> TYPE: PRT
<213> ORGANISM: Mus musculus

<400> SEQUENCE: 11

Met Ser Ser Gln Gln Tyr Gln Gln Gln Arg Arg Lys Phe Ala Ala Ala
1               5                   10                  15

Phe Leu Ala Leu Ile Phe Ile Leu Ala Ala Val Asp Thr Ala Glu Ala
            20                  25                  30

Gly Lys Lys Glu Lys Pro Glu Lys Val Lys Lys Ser Asp Cys Gly
        35                  40                  45

Glu Trp Gln Trp Ser Val Cys Val Pro Thr Ser Gly Asp Cys Gly Leu
 50                  55                  60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95
```

-continued

```
Ala Glu Cys Lys Tyr Gln Phe Gln Ala Trp Gly Glu Cys Asp Leu Asn
            100                 105                 110

Thr Ala Leu Lys Thr Arg Thr Gly Ser Leu Lys Arg Ala Leu His Asn
            115                 120                 125

Ala Asp Cys Gln Lys Thr Val Thr Ile Ser Lys Pro Cys Gly Lys Leu
            130                 135                 140

Thr Lys Pro Lys Pro Gln Ala Glu Ser Lys Lys Lys Lys Lys Glu Gly
145                     150                 155                 160

Lys Lys Gln Glu Lys Met Leu Asp
                165
```

TRANSGENIC ANIMAL MODEL OF MOOD DISORDERS

CROSS REFERENCE TO RELATED APPLICATIONS

This is the U.S. National Stage of International Application No. PCT/EP2013/055253, filed Mar. 14, 2013, which was published in English under PCT Article 21(2), which in turn claims the benefit of GB Application No. 1204816.1, filed Mar. 19, 2012, which is incorporated herein in its entirety.

FIELD OF THE INVENTION

The present invention relates to a marker for psychiatric illness, particularly mood disorders such as Major Depressive Disorder (MDD), Anxiety and Bipolar Disorder (BD), to animal models utilising the marker, to methods of screening for agents that affect the marker and which may have therapeutic potential, and to uses for treatment based on down-regulation of the marker expression and/or antagonism of its activity.

BACKGROUND TO THE INVENTION

Psychiatric disorders such as major depression, anxiety or bipolar disorder are becoming one of the major public-health problems on a global scale. The causes of these disorders are as yet poorly understood, although genetic factors undoubtedly play an important role in their aetiology. Furthermore, these illnesses do not develop because of the alteration of one single gene but more likely due to changes in a group of genes, which makes them multi-factor illnesses.

Mood disorders such as major depression, anxiety and bipolar disorders are the most common psychiatric disorders in modern society. About 16% and 1% of the population are estimated to be affected by major depression and bipolar disorder one or more times during their lifetime, respectively. Such disorders affect approximately 121 million people worldwide, with 20% of women and 12% of men estimated to experience a depressive episode in any 1-year period and with evidence of suicidality in 15% of those affected. In this context, major depression has been projected to become the second leading cause of disability worldwide by 2020 (second to ischemic heart disease) (Lee et al., 2010) (www.who.int).

Depression is related to the normal emotions of sadness and bereavement, but it does not remit when the external cause of these emotions dissipates, and it is disproportionate to their cause. It is defined by episodes of depressed mood lasting for greater than 2 weeks accompanied by additional symptoms including disturbed sleep and appetite, reduced concentration and energy, excessive guilt, slowed movements and suicidal thoughts. Also, depression is associated with considerable morbidity and excess mortality (Sullivan et al., 2000; Belmaker and Agam, 2008). Interestingly, approximately one-third of patients suffering from MDD are refractory to any kind of antidepressant treatment.

The resulting cost to the US economy is estimated to be in the range of US $100 billion per year. But in spite of these considerable financial incentives and the public health importance of treating depression, there is an absence of conceptually novel antidepressants on the market, reflecting the difficulties encountered in the development of new treatment strategies for this common and complex disorder.

Despite extensive investigations, the exact mechanisms responsible for MDD have not been identified. In this context, several hypotheses have been proposed to explain the aetiol- Alternative hypotheses for MDD have recently provided the rationale for the emergence of new strategies for antidepressant drug development. These new strategies could indicate that researchers and pharmaceutical companies are now considering the various alternative hypotheses for MDD as complementary rather than competing. Such a position could bring a broader recognition of the heterogeneity of MDD, thereby fostering an expansion of treatment approaches (Wong and Licinio, 2004).

In recent years, it has been postulated that depression and anxiety may be caused by cytokine secretion associated with activation of the immune system. This hypothesis was proposed initially because the incidence of immune abnormalities is higher in depressed and anxious patients than in the general population, and because depression is a common side effect of cytokine therapy. Cytokines, which are humoral mediators of innate and adaptive immunity, are also important modulators of mood. Cytokine receptors within the central nervous system are activated by both peripherally and centrally synthesized cytokines. Low doses of lipopolysaccharide or interleukin 1 (IL-1) produce 'sickness behaviour' in rodents (consisting of social withdrawal and decreased exploratory and sexual behaviour), brought about by the release of pro-inflammatory cytokines such as interferon-α, tumour necrosis factor-α (TNF-α), IL-6 and IL-1β, which activate the hypothalamic-pituitary-adrenal axis and central monoamine systems. There are many similarities between sickness behavior and the symptoms of depression. Thus it was suggested that cytokines could induce depression, or indeed were the cause of depression. This hypothesis has come to be called the cytokine hypothesis of depression. Studies found that inflammatory cytokines levels decreased with various antidepressants treatments, suggesting than antidepressants may reduce inflammation. Conversely, anti-inflammatory drugs can have an antidepressant effect. Such data support the notion that inflammation may in some way contribute to the genesis of depressive symptoms (Dunn et al., 2005; DellaGioia and Hannestad, 2010).

Animal models are widely used to study the neurobiological mechanisms of depression and anxiety but mouse models that mimic the full phenotypic spectrum of a psychiatric disorder, such as major depression, are virtually impossible. However, a recreation of some phenotypic components is feasible and animal models of this disease often try to mimic some symptoms of the disorder. Ideal animal depression models must be reasonably analogous to the human symptoms, be able to be monitored objectively, be reversed by the same treatment modalities as humans, and be reproducible between laboratories. Interestingly, antidepressant treatment has been shown to affect the behavioural responses in these models indicating that certain depression paradigms are pharmacologically sensitive, and therefore, can be used in the testing of antidepressant drugs in mice. In this context, animal models have a central role in discovering the causes of psychiatric disorders and generating novel mechanism-based treatments. One of the most important advances in understanding psychiatric disorders has been the development of mice with genetically altered expression of a specific protein. These new tools have the potential to examine novel targets for antidepressant activity. Additionally, these mice will enable better testing of the validity of current molecular theories of depression. However, it is difficult to prepare a model reflecting a human disease having a mechanism of development which is unknown, such as depression (Krishnan and Nestler, 2010).

There is at present an unmet need for animal models of psychiatric diseases such as major depression and/or anxiety. A significant difficulty remains the translation of genetic association studies into models that are effective for evaluating the efficacy of candidate therapeutic compounds. In particular, the complexity of the disorder means that it is not normally possible to predict whether a genetic alteration associated with the disorder has a causal role and will produce behavioural changes of relevance to depression and/or anxiety.

DISCLOSURE OF THE INVENTION

The present inventors have now found that Pleiotrophin (PTN or Heparin Binding Growth Associated Molecule: HB-GAM) expression is altered in the prefrontal cortex of depressed patients who died by suicide, when compared with samples taken from the same brain region of control individuals with no history of mental illness and who died accidentally. Pleiotrophin is a 136 amino acid secreted heparin-binding cytokine (Milner et al., 1992). Ptn gene is expressed in cells in early differentiation stages during several developmental periods. Also, Ptn is over-expressed in different types of cancer (Kadomatsu and Muramatsu, 2004). PTN responses are mediated by different receptors: PTN inactivates the receptor protein tyrosine phosphatase (RPTP) $\beta/\zeta$ inducing its dimerization. PTN stimulates phosphorylation (activation) of Anaplastic Lymphoma Kinase (ALK) (a tyrosine receptor kinase) through the PTN/RPTPβ/ζ signaling pathway. PTN can also interact with the Syndecan-3 receptor. The interaction of PTN with RPTPβ/ζ, disrupts normal association of β-catenin with E-cadherin (Deuel et al., 2002; Furuta et al., 2004).

Furthermore, the findings disclosed herein indicate that enhanced expression of PTN protein is not merely a consequential change associated with depression and/or anxiety, but appears to have a causal role, as shown by depressive-related behavioural changes in transgenic mice that overexpress PTN in brain. The difference observed in PTN levels in drug-treated and drug-free depressive patients makes PTN an attractive drug target and screening tool for candidate therapeutics for psychiatric conditions, including depression and/or anxiety. Interestingly, some of the principal players involved in PTN mediated signalling have been found altered in Major Depression.

Accordingly, in a first aspect the present invention provides a non-human transgenic animal having a polynucleotide encoding a PTN polypeptide, which polynucleotide is operably linked to a promoter, wherein said transgenic animal has greater than wild-type expression of the PTN polypeptide in at least one brain region. The transgenic animal exhibits one or more anxious and/or depressive-related behaviours, for example: reduced time spent in open arms of an elevated plus maze; reduced time in central area in an open-field test; reduced time in light in a light-dark box test; increased latency to feed in a Novelty Suppressed Feeding Test, increased immobility time in tail suspension test; and reduced sucrose intake in sucrose intake task.

The transgenic mice described in detail herein were created with inclusion of a neuronal specific promoter, the Thy promoter, which is more neuronal specific than PDGF promoter which is expressed also in other tissues (Tesseur et al., 2000). The PDGF promoter was used to create transgenic mice that also over express PTN not only in neurons (Pavlov et al., 2002). Moreover, the PTN mice of Pavlov et al., 2002, were found to exhibit decreased anxiety in the elevated plus maze test (i.e. more entries on the open arms). This is in marked contrast to the present findings, wherein the PTN mice of the present invention, as described in detail herein, were found to exhibit greater anxiety-like behaviour than wild-type controls (e.g. spending less time, and walking less distance, in the open arm). The choice of promoter and the corresponding tissue expression of the PTN transgene has an important effect on the behaviour of the PTN transgenic animal, such that the PTN mice of Pavlov et al., 2002, are unsuited to use as a model for psychiatric illness, particularly disorders of mood, whereas the PTN transgenic animal of the present invention, having more neuronal-specific expression of the PTN transgene as compared with the PTN mice of Pavlov et al. 2002, preferably exhibit at least one anxiety and/or depressive-like behaviours, e.g. one or more anxiety and/or depression-related behaviours selected from: reduced motor activity in an open-field test; reduced time spent in open arms of an elevated plus maze; reduced time spend in the lit portion of a light-dark box; increased latency to feed in a Novelty Suppressed Feeding Test; increased immobility time in tail suspension test; and decreased sucrose intake. Without wishing to bound by any particular theory, the present inventors believe that the greater neuronal-specificity of the Thy1 promoter employed herein as compared with the PDGF beta promoter employed by Pavlov et al., 2002, contributes to the anxiety and/or depression-related behaviour of the transgenic animal of the present invention.

The PTN transgenic mice described in the Examples herein, having the PTN gene under the control of a Thy1 promoter, exhibit up-regulation of PTN expression in multiple brain regions that is in the range approximately 2.1 to as high as 6.4-fold higher than wild-type littermates (PTN ratio of TG (transgenic) to WT (wild-type). This is a greater level of over-expression than that reported for Pavlov et al., 2002 (approximately 2-fold overexpression in the hippocampus as determined by Western Blot). Greater neuronal expression of another gene, human Apolipoprotein E4, has been reported when the Thy1 promoter is compared with the PDGF beta promoter (Tesseur, et al., 2000).

Further examples of Neuron-Specific Promoters that can be used to create transgenic mice, in accordance with the present invention, that overexpress PTN specifically in brain include (see Table 4): Neuron specific enolase (NSE); Rhombotin I; PGK; Neurofilament Low (NF-L); dopamine beta-hydroxylase (DBH); Synapsin-1.

The expression of PTN in mouse brain under mouse Thy1 promoter induces a depressive-anxious-like phenotype. In contrast previously described by Pavlov et al., when human PDGF promoter is used to drive PTN overexpression in mice, this phenotype is not replicated. Interestingly, animals with overexpression of a target gene under Thy1 promoter, showed higher expression levels than those with human PDGF promoter (Tesseur et al., 2000). Furthermore, the Thy1 promoter shows a brain tissue-specific expression pattern, focusing mainly in cortex and the hippocampus, two key regions in the development of Mood Disorders, whereas the PDGF promoter shows a generalized expression in the brain and even in other organs (Tesseur et al., 2000). Without wishing to be bound by any particular theory, it is presently believed that these two differences may be key because the more specific and higher expression of the target gene, the greater the possibility to obtain a model that mimics more severe symptoms of the disease as well as more specificity in obtained phenotypes. Finally, the use of mouse promoter may also be key to obtain a better animal model of Mood Disorders comparing with the PDGF promoter of human origin, due to the advantage of using a DNA sequence with the same origin as the expression machinery to be used.

The transgenic animal of the invention may contain a foreign gene or promoter (i.e. genetic material from another species) or it may not contain any foreign gene or promoter. The latter case is considered transgenic herein by virtue of an alteration in the location, copy number or sequence of a PTN-encoding polynucleotide and/or an alternation in the promoter controlling expression of the PTN-encoding polynucleotide. In certain cases, the transgenic animal of the invention may have said polynucleotide encoding a PTN polypeptide present in a higher than wild-type copy number. For example, the transgenic animal may carry a native or non-native ptn gene in higher than diploid copy number. The transgenic animal of the invention may have the polynucleotide encoding a PTN polypeptide operably linked to a promoter which is other than a ptn gene promoter and which is other than the human PDGF beta-chain promoter. Thus, for example, the promoter may be an endogenous or exogenous promoter from another gene, preferably a promoter from a gene which exhibits brain-specific or largely brain-specific expression. In accordance with this and other aspects of the present invention, the promoter may be selected from the group consisting of: the human or mouse Thy1 gene promoter; human or mouse Neuron specific enolase (NSE); human or mouse Rhombotin I; PGK; human or mouse Neurofilament Low (NF-L); human or mouse dopamine beta-hydroxylase (DBH); human or mouse Synapsin-1.

In certain cases of the transgenic animal according to the invention said polynucleotide encodes a PTN polypeptide which is a mouse, rat or human PTN polypeptide, a variant (such as a splice variant), precursor (such as the 168 amino acid human pleiotrophin precursor sequence available at NCBI accession number NP_002816; GI: 4506281 or the 168 amino acid mouse pleiotrophin precursor sequence available at NCBI accession number NP_032999; GI: 6679543), derivative (such as a post-translationally processed polypeptide), homologue or orthologue from another species (preferably a mammalian homologue or orthologue) or fragment. The PTN polypeptide or fragment thereof preferably exhibits biological activity, particularly the ability to bind to its specific receptors such as RPTPβ/ζ, ALK or Syndecan 3. In preferred cases of the transgenic animal according to the invention said polynucleotide encodes:

(i) a PTN polypeptide having an amino acid sequence having at least 80%, 90%, 95% or 99% amino acid sequence identity to the sequence of SEQ ID NO: 2;
(ii) a PTN polypeptide having the amino acid sequence of SEQ ID NO: 2
(iii) a PTN polypeptide having an amino acid sequence having at least 80%, 90%, 95% or 99% amino acid sequence identity to the sequence of SEQ ID NO: 4;
(iv) a PTN polypeptide having the amino acid sequence of SEQ ID NO: 4; or
(v) an active fragment of any one of (i)-(iv) having at least 100, 110, 120 or 130 amino acids, wherein said PTN polypeptide of any one of (i)-(iv) or said active fragment of (v) is capable of binding to its specific receptors, such as RPTPβ/ζ, ALK or Syndecan 3 polypeptide.

In certain cases of the transgenic animal according to the invention said promoter is a brain-specific promoter. Preferably, the promoter is specific for neurons. In certain cases, in accordance with this and other aspects of the present invention, the promoter is selected from the group consisting of: the human or mouse Thy1 gene promoter; human or mouse Neuron specific enolase (NSE); human or mouse Rhombotin I; PGK; human or mouse Neurofilament Low (NF-L); human or mouse dopamine beta-hydroxylase (DBH); human or mouse Synapsin-1. Further details of the promoters are provided in Table 4 below. A particularly preferred promoter is the promoter of the Thy1 gene, especially a Thy1 promoter of the same species as the transgenic animal. The Thy1 promoter may comprise or consist of a polynucleotide having at least 80%, 90%, 95% or 99% nucleotide sequence identity to the sequence of SEQ ID NO: 5. The present inventors have found that the Thy1 promoter permits elevated expression of PTN in a targeted manner; expression is largely confined to cortical and hippocampal neurons, and also in other regions as the amygdala. Thus, use of the Thy1 promoter to drive expression of PTN provides an advantageous way to induce the desired anxious and/or depressive-like phenotype of certain embodiments of the transgenic animal of the invention.

The transgenic animal of the invention has greater than wild-type expression of the PTN polypeptide, as defined herein, in at least one brain region selected from: cortex and hippocampus. Results disclosed herein indicate that elevated expression of PTN in one or more of these brain regions contributes to, or underlies the anxious-depressive-like phenotype observed. The elevated expression may, in some cases, be a relatively modest increase in expression compared with wild-type (e.g. compared with the expression in the same brain region of a species-, gender- and age-matched wild-type animal which does not carry any genetic alteration relating to PTN or its promoter). In some cases, elevated expression may be at least 10%, 20%, 30%, 50%, 100%, 200%, 300% or 400% or greater expression of the PTN polypeptide in said at least one brain region. A variety of techniques are available for measuring expression of PTN, including techniques for direct measurement of protein levels (e.g. Western blot and immunofluorescence) and techniques for indirect measurement based on measurement of mRNA encoding the PTN polypeptide (e.g. qPCR).

The transgenic animal of the invention is preferably a rodent, such as a mouse or rat. In some cases the transgenic animal of the invention may be a non-human primate or other laboratory animal such as a dog or cat. Most preferably, the transgenic animal is a mouse (e.g. *Mus musculus*).

In a second aspect the present invention provides a vector comprising a polynucleotide encoding a PTN polypeptide operably linked to a brain-specific promoter which is other than a ptn gene promoter and other than the human PDGF beta-chain gene promoter and, optionally, further regulatory sequences. Preferably, said polynucleotide encodes a PTN polypeptide which is a mouse, rat or human PTN polypeptide, a variant (such as a splice variant), precursor (such as the 168 amino acid human pleiotrophin precursor sequence available at NCBI accession number NP_002816; GI: 4506281 or the 168 amino acid mouse pleiotrophin precursor sequence available at NCBI accession number NP_032999; GI: 6679543), derivative (such as a post-translationally processed polypeptide), homologue or orthologue from another species (preferably a mammalian homologue or orthologue) or fragment. The PTN polypeptide or fragment thereof preferably exhibits biological activity, particularly the ability to bind to its specific receptors RPTPβ/ζ, ALK or Syndecan 3. In preferred cases of the vector of this aspect of the invention said polynucleotide encodes:

(i) a PTN polypeptide having an amino acid sequence having at least 80%, 90%, 95% or 99% amino acid sequence identity to the sequence of SEQ ID NO: 2;
(ii) a PTN polypeptide having the amino acid sequence of SEQ ID NO: 2
(iii) a PTN polypeptide having an amino acid sequence having at least 80%, 90%, 95% or 99% amino acid sequence identity to the sequence of SEQ ID NO: 4;
(iv) a PTN polypeptide having the amino acid sequence of SEQ ID NO: 4; or
(v) an active fragment of any one of (i)-(iv) having at least 100, 110, 120 or 130 amino acids, and wherein said PTN polypeptide of any one of (i)-(iv) or said active fragment of (v) is capable of binding to specific receptors RPTPβ/ζ, ALK or Syndecan 3 polypeptide.

Said promoter of the vector of this aspect of the invention may be specific or largely specific to neurons. A preferred promoter of the vector of this aspect of the invention is a Thy1 promoter. The Thy1 promoter may comprise or consist of a polynucleotide having at least 80%, 90%, 95% or 99% nucleotide sequence identity to the sequence of SEQ ID NO: 5. The vector of this aspect of the invention may find use in the preparation of a transgenic animal model of the first aspect of the invention.

In a third aspect the present invention provides an in vitro method for identifying an agent (e.g. a small molecule, a nucleic acid or a protein) for use in the treatment of neuropsychiatric illnesses, particularly mood disorders such as anxiety and/or major depression, comprising:

(i) contacting a cell that expresses a PTN polypeptide with a test agent and measuring, directly or indirectly, expression of the PTN polypeptide relative to expression of the PTN polypeptide in a control cell which has not been exposed to the test agent; and/or
(ii) contacting a PTN polypeptide with a test agent and measuring, directly or indirectly, binding of the PTN polypeptide to specific receptors RPTPβ/ζ, ALK or Syndecan 3 relative to the binding of a control PTN polypeptide which has not been exposed to the test agent to specific receptors RPTPβ/ζ, ALK or Syndecan 3 polypeptide; and/or
(iii) contacting a cell that presents PTN specific receptors with a PTN polypeptide and with a test agent and measuring, directly or indirectly, neurogenesis (proliferation, differentiation or migration) and/or synaptogenesis.

wherein a reduction in said expression in (i) and/or a reduction in said binding in (ii) and/or an alteration in neurogenesis and/or synaptogenesis in (iii) due to the test agent indicates that the test agent is potentially useful in the treatment of neuropsychiatric illnesses, particularly mood disorders such as anxiety and major depression. Preferably, said cell that expresses a PTN polypeptide and/or said cell that presents PTN specific receptors is a neuronal cell or non-neuronal cell obtained from:

a patient having a neuropsychiatric illness, particularly mood disorders such as anxiety and/or major depression or,
a transgenic animal of the invention or,
a cell that has been transfected or transformed with a polynucleotide encoding a PTN polypeptide or with a vector in accordance with the second aspect of the invention or,
A cell that expresses at least one PTN specific receptor, such as RPTPβ/ζ, ALK or Syndecan 3.

Expression of PTN polypeptide may be measured at any stage of expression of the PTN-coding gene (e.g. measuring mRNA level or protein level). In preferred cases of the method of this aspect of the invention the test agent is found to reduce said expression in (i) and/or said binding in (ii) and/or neurogenesis and/or synaptogenesis in (iii). Such test agents may be regarded as functional antagonists of the PTN polypeptide (whether they act pre- or post-translationally). Test agents that are found to reduce said expression in (i) and/or said binding in (ii) and/or neurogenesis and/or synaptogenesis in (iii) may be subjected to further screening (including in vivo screening as described further herein). In some cases the method of this aspect of the invention further comprises isolating the test agent and, optionally, formulating the test agent into a pharmaceutical composition with at least one pharmaceutically acceptable salt, carrier or excipient.

In a related aspect the present invention provides an in vitro screening method comprising:

contacting at least one cell that expresses a PTN polypeptide and/or at least one PTN specific receptor, such as RPTPβ/ζ, ALK or Syndecan 3 with a test agent; and
detecting whether said test agent alters a PTN-related activity as compared with said activity in the absence of the test agent.

The method may comprise detecting a change in PTN-related activity in the presence of the test agent as compared with said PTN-related activity in the absence of the test agent. The method may comprise comparing the PTN-related activity of a cell exposed to the test agent with said PTN-related activity of a (second) "control cell" which has not been exposed to the test agent. Additionally or alternatively, the method may comprise comparing the PTN-related activity of a cell exposed to the test agent with said PTN-related activity of the same cell in the absence of the test agent. For example a "baseline" of said PTN-related activity may be established prior to addition of the test agent and the PTN-related activity assessed (e.g. relative to said baseline) after exposing the cell to the test agent. Preferably, the cell is a cell that expresses at least one PTN specific receptor, or a cell that has been transfected or transformed with a vector comprising a polynucleotide that encodes said PTN polypeptide, e.g. a vector in accordance with the second aspect of the invention. In particular, the cell may be a neuronal cell line (e.g. a human or animal, such as rodent, derived cell line), and/or a primary culture that has been extracted from the brain of the transgenic mice of the present invention or from the brain of any other animal or a stem cell-derived neuronal cell. The cell used in the method according to this aspect of the invention may comprise a vector comprising a polynucleotide that encodes a PTN polypeptide operably linked to a promoter, such as a promoter that permits variable expression of the PTN. The promoter may be a Thy1 promoter as defined in accordance with the tenth aspect of the invention. Alternatively or additionally, a plurality of cells each comprising a vector comprising a polynucleotide that encodes a PTN polypeptide operably linked to a promoter may be used in accordance with the method of this aspect of the invention. In some cases, the plurality of cells may comprise sub-sets of cells, wherein the cell of each sub-set has a vector having a promoter that differs from the promoter of the vectors of cells of other of said sub-sets, such that the expression level of PTN differs between said sub-sets of cells. Preferably, a first sub-set of cells is characterised by relatively low expression of PTN and a second sub-set of cells is characterised by higher expression of PTN relative to said first sub-set of cells.

In a fourth aspect the present invention provides an in vivo method for identifying an agent for use in the treatment of neuropsychiatric illnesses, particularly mood disorders such as anxiety and/or major depression, comprising:

(i) administering a test agent to a transgenic animal of the invention and subsequently measuring, directly or indirectly, the expression of a PTN polypeptide in at least one brain region relative to the expression of the PTN polypeptide in at least one brain region of a control transgenic animal of the invention, which has not been exposed to the test compound; and/or (ii) administering a test agent to a transgenic animal of the invention and subsequently assessing the presence and/or severity of one or more anxiety and/or depressive-related behaviours in the transgenic animal relative to the one or more depressive-related behaviours in a control transgenic animal of the invention, which has not been exposed to the test agent, and/or (iii) administering a test agent to a transgenic animal of the invention and subsequently evaluating the neurogenesis and synaptogenesis processes in the transgenic animal relative to the neurogenesis and synaptogenesis in a control transgenic animal which has not been exposed to the test agent.

Wherein a reduction in said expression in (i) and/or said one or more anxiety and/or depressive-related behaviours in (ii) and/or and increase in neurogenesis and/or synaptogenesis in (iii) due to the test agent indicates that the test agent is potentially useful in the treatment of neuropsychiatric illnesses, particularly mood disorders such as anxiety and/or major depression. Said one or more anxiety and/or depressive-related behaviours may be selected from: reduced motor activity in an open-field test; reduced time spent in open arms of an elevated plus maze; reduced time in the lit portion of a light-dark box; increased latency to feed in a Novelty Suppressed Feeding test, increased time immobile on tail suspension test; and decreased sucrose intake . . . . Preferably, in the method of this aspect of the invention the test agent is found to reduce said expression in (i) and/or said one or more anxiety and/or depressive-related behaviours in (ii) and/or increase neurogenesis and/or synaptogenesis in (iii). Such test agents may be regarded as in vivo functional antagonists of PTN and/or PTN-associated anxiety, depressive-like behaviour, neurogenesis, and/or synaptogenesis. In some cases the test agent is an agent which has previously been tested in a method of the third aspect of the invention. In this way an initial in vitro screen may be used to target subsequent in vivo screening on more promising candidate agents.

The method of this aspect of the invention may further comprise isolating the test agent and, optionally, formulating the test agent into a pharmaceutical composition with at least one pharmaceutically acceptable salt, carrier or excipient.

In a fifth aspect the present invention provides an agent identified or identifiable by a method of the fourth or fifth aspect of the invention. The agent may be for use in medicine. Preferably, the agent is for use in a method of treating a neuropsychiatric illness, particularly mood disorders such as anxiety and/or major depression. Preferably, the agent comprises:

an antibody molecule or binding fragment thereof capable of binding to a PTN polypeptide (e.g. an PTN polypeptide as defined in relation to any aspect of the present invention); or an antisense nucleic acid, ribozyme, triple helix molecule, siRNA, miRNA or other nucleic acid capable of inhibiting PTN gene expression (e.g. which is capable of hybridising to at least a portion of a polynucleotide that encodes an PTN polypeptide as defined in relation to any aspect of the present invention or which is capable of hybridising to at least a portion of a polynucleotide which is complementary to the polypeptide that encodes the PTN polypeptide).

a small molecule, antibody molecule or binding fragment, antisense nucleic acid, ribozyme, triple helix molecule, siRNA, miRNA capable of antagonising the effect of PTN over-expression.

In a sixth aspect the present invention provides use of an agent identified or identifiable by a method of the fourth or fifth aspect of the invention in the preparation of a medicament for treatment of neuropsychiatric illnesses, particularly mood disorders such as anxiety and/or major depression. Said agent may be as defined in relation to the sixth aspect of the invention.

In an seventh aspect the present invention provides a method for treating a neuropsychiatric illness, particularly mood disorders as anxiety and/or major depression, in a subject (e.g. a human patient in need of said treatment), comprising administering a therapeutically effective amount of an agent identified or identifiable by a method of the fourth or fifth aspect of the invention. Said agent may be as defined in relation to the sixth aspect of the invention.

In an eighth aspect the present invention provides a method of assessing the presence of or susceptibility to a neuropsychiatric illness in a subject, particularly mood disorders such as anxiety and/or major depression, comprising:

detecting and/or determining the amount of a PTN polypeptide and/or the amount of an mRNA or cDNA encoding an PTN polypeptide in a sample which has been obtained from said test subject; and comparing said amount of the PTN polypeptide and/or said amount of the mRNA or cDNA encoding the PTN polypeptide with one or more reference values corresponding to the amount of the PTN polypeptide and/or the amount of the mRNA or cDNA encoding the PTN polypeptide in a control sample obtained from a control subject not having a neuropsychiatric illness. The sample may comprise blood, plasma, serum, cerebrospinal fluid (CSF) or tissue. Preferably, the sample comprises central nervous system tissue (e.g. prefrontal cortex tissue).

In certain cases of the method of this aspect of the invention the test subject has not previously been diagnosed as having a neuropsychiatric illness, such as anxiety and/or major depression. In certain other cases of the method of this aspect of the invention the test subject has previously been diagnosed as having a neuropsychiatric illness. The method of this aspect of the invention may be used to assess the stage and/or severity of the neuropsychiatric illness, to select the patients that will benefit from the treatments, or to monitor the effect of a treatment administered to the test subject.

In a ninth aspect the present invention provides a vector comprising a polynucleotide encoding a psychiatry-associated polypeptide operably linked to a Thy1 promoter and optionally further regulatory sequences. Preferably, the Thy1 promoter comprises or consists of a polynucleotide having at least 80%, 90%, 95% or 99% nucleic acid sequence identity to the sequence of SEQ ID NO: 5 or the Thy1 promoter comprises or consists of a polynucleotide having the sequence of SEQ ID NO: 5. The polynucleotide encoding a psychiatry-associated polypeptide is preferably a gene, the elevated expression of which has been found to be associated with a neuropsychiatric illness (e.g. mood disorders such as anxiety and/or major depression). In accordance with this aspect of the invention, the psychiatry-associated polypeptide is preferably a gene product of a gene set forth in Table 1 or Table 3 herein.

In a tenth aspect, the present invention provides use of a vector of the ninth aspect of the invention, in the production of a transgenic animal having greater than wild-type expression of said psychiatry-associated polypeptide in at least one brain region. The transgenic animal so produced and its offspring may be utilised in screening of test agents for potential treatments of the psychiatric disorder, such as anxiety and/or major depression.

The present invention includes the combination of the aspects and preferred features described except where such a combination is clearly impermissible or is stated to be expressly avoided. Section headings used herein are for convenience only and are not to be construed as limiting in any way. These and further aspects and embodiments of the invention are described in further detail below and with reference to the accompanying examples and figures.

DESCRIPTION OF THE FIGURES

FIGS. 1A and 1B provide information regarding samples included in the study. In FIG. 1 the information associated with each sample is distributed in columns: FIG. 1A) provides data for major depressive subjects and FIG. 1B) provides data of the respective matched control subjects. The first of these corresponds to the sample code, and is followed by the sex, age, post mortem delay (PMD) and finally the toxicological data (drug free corresponds to negative toxicology). The table also includes in which kind of experiment the samples were used: chips from Affymetrix, validation of candidate genes by RT-PCR and characterization of proteins levels by western blot.

FIGS. 2A-2C are a series of panels showing quantification of PTN in total homogenate of human brain. FIG. 2A) Immunoreactivity for the PTN protein determined in total homogenate of the prefrontal cortex (Brodmann area 9) of depressive subjects who died by suicide (n=22) and separated into untreated (drug-free; DF, n=10) and treated with antidepressant drugs (treated; T, n=12). The data are expressed as a percentage of the mean value±SEM (standard error). The relative content of each protein was calculated as percent change in relation to in-gel triplicate standards fixed at 100%, (pool of controls samples). The total group (All) of depressive subjects (123±9%, n=22, p<0.009, one-sample t-test) and the group of untreated depressive subjects (135±14%, n=10, p=0.006, one-sample t-test) give significantly higher values than the controls. However, the group of treated subjects (112±10%, n=12, p=0.2, not significant, one-sample t-test) give no significantly higher values than controls. FIG. 2B) Immunoreactivity for the actin protein determined in total homogenate of the prefrontal cortex (Brodmann area 9) of depressive subjects who died by suicide (n=22) and separated into untreated (drug-free; DF, n=10) and treated with antidepressant drugs (treated; T, n=12). The data are expressed as a percentage of the mean value±SEM (standard error). The relative content of each protein was calculated as percent change in relation to in-gel triplicate standards fixed at 100%, (pool of controls samples). The total group (All) of depressive subjects (99±3%, n=22, not significant), the group of untreated depressive subjects (96±4%, n=10, not significant) and the group of treated subjects (101±4%, n=12, not significant,) give similar values than controls. FIG. 2C) Representative autoradiograms ("immunoblots") of the protein PTN in post-mortem human brain (prefrontal cortex, Brodmann area 9) of untreated depressive subjects who died by suicide (drug-free; DF), those treated with antidepressant drugs (treated; T) and their respective controls (C). Brain samples containing 40 mg of total protein each were loaded onto 10% polyacrylamide gels. [C1=♀, 35 years, 17 hours PMD; DF1=♀, 35 years, 23 hours PMD; C2=♀, 57 years, 4 hours PMD; DF2=♀, 54 years, 12 hours PMD; where PMD is the time between death and autopsy].

FIG. 3A) The transgene construct. FIG. 3B) Southern blot showing expression of PTN in transgene-negative (WT: lanes 3,4,6,7 y 8) and transgene-positive (PTN-overexpressing "PTN-OE": lanes 5 and 9) littermates (Ctr: endogenous mRNA; M: marker; WT: Transgene-negative; TG: mRNA transcribed from the transgene) using the complete PTN cDNA as a probe. FIG. 3C) agarose gel microphotography following PCR amplification (WT: wild type mouse; Tg: transgenic mouse). FIG. 3D) PTN mRNA hippocampal and cerebral cortex expression levels in PTN-OE male mice and WT littermates. Values are shown as relative expression level $2^{-\Delta\Delta CT}$. FIG. 3E) Immunoreactivity for the PTN protein determined in total homogenate of hippocampus and cerebral cortex (respectively) of wild type control mice and transgenic mice (PTN-OE). Data are expressed as a percentage of the mean value±SEM (standard error) and expressed as percentage of control group. **$p<0.01$, *$p<0.04$ when compared with the corresponding control group (the two-tailed one-sample t-test). FIG. 3F) Neuroanatomical distribution of PTN mRNA in WT and PTN-OE mice.

FIG. 4.—. Semiquantification of PTN mRNA levels in several areas in wild-type (wt) and transgenic (tg) animals. Relative optical densities are shown. aCA1, anterior CA1 hippocampal field; aCA3, anterior CA3 hippocampal field; aDG, anterior dendate gyrus; aCx, anterior cingulated cortex; aCPu, anterior caudate-putamen; aAmy, anterior amygdale nuclei; aRt, anterior Reticular thalamic nuclei; mCA1, medial CA1 hippocampal field; mCA3, medial CA3 hippocampal field; mDG, medial dendate gyrus; mCx, medial cingulated cortex; mDPu, medial caudate-putamen; mRt, medial Reticular thalamic nuclei; pCA1, posterior CA1 hippocampal field; pCA3; posterior CA3 hippocampal field; pDG, posterior dendate gyrus; pCx, posterior cingulated cortex; PK, Purkinje cells of the cerebellum; GR, granular cells of the cerebellum; nd: no determined.

FIG. 6.—General observation of animal behavior. Results are expressed as % of PTN-OE and Wild-type animals exhibiting a given behavioral parameter of those described in Irwin's test protocol.

FIGS. 7A-7I are a series of panels showing assessment of spontaneous locomotor activity and Anxiety-like behavior measured in the open field in controls and transgenic mice. The following parameters were measured in the activity boxes: (FIG. 7A) total motor activity, (FIG. 7B) locomotor activity and (FIG. 7C) rearing. Data are expressed as mean±S.E.M (n=18, wild-type and n=21, transgenic). The following parameters were measured in the open field under stressful conditions: (FIG. 7D) time spent in central area, (FIG. 7E) crossing squares in central area, (FIG. 7F) entries in central area, (FIG. 7G) crossing squares in peripheral area, (FIG. 7H) grooming and (FIG. 7I) rearing. Data are expressed as mean±S.E.M (n=18, wild-type and n=21, transgenic). *$p<0.05$ and **$p<0.01$ when comparing with wild-type group.

FIGS. 8A-8I are a series of panels showing assessment of anxiety-like and depressive-like behaviours, Tail Suspension Test and in Sucrose Intake in transgenic and wild-type mice. Elevated Plus Maze: FIG. 8A) Number of entries in open arms; FIG. 8B) Percent of distance that mice spent in the open arms; FIG. 8C) Percent of time that mice remain in the open arms (Behaviour was evaluated for a period of 5 min). Light-Dark Box: FIG. 8D) Latency to go for the first time to the lit compartment; FIG. 8E) time spent in the lit compartment; FIG. 8F) Number of squares crossed FIG. 8G) number of visits into each zone of the lit compartment are recorded for 5 min through a videocamera system. Tail suspension test: FIG. 8H) Time of immobility during 6 minutes session; Sucrose intake Test: FIG. 8I) Performance in the sucrose intake test show a reduced intake of sucrose Data are expressed as mean±SEM of percentage. Values from PTN-OE mice (black columns) that are significantly different (*$p<0.05$, **$p<0.002$ the two-tailed one-sample t-test) from control mice (white columns) are indicated.

FIG. 10.—Shows the mouse (*Mus musculus*) PTN cDNA sequence available under NCBI Accession No BC061695.1 [GI:38197284] (SEQ ID NO: 1).

FIG. 11.—shows the mouse (*Mus musculus*) PTN predicted translated sequence. The mature form of the protein is residues 33-168 available under NCBI Accession No. NM_008973 [GI:118130571] (SEQ ID NO 2).

FIG. 12.—Shows the human Pleiotrophin (PTN) cDNA sequence available under NCBI Accession No. BC005916.1 [GI:13543514] (SEQ ID NO: 3).

FIG. 13.—Shows the human PTN amino acid sequence available under Uniprot Accession No. P21246, version 1, 1 May 1991. The mature sequence is residues 33-168 (SEQ ID NO: 4).

FIGS. 14A-14D are a series of panels showing the sequence of the acceptor vector pTSC-a2 which contained the regulatory regions responsible for tissue specific expression of the mouse (*Mus musculus*) THYmocyte differentiation antigen 1 gene (Thy-1) sequence (SEQ ID NO: 5).

Figure 3A:
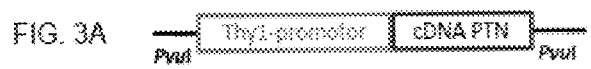
FIGS. 3A-3F are a series of panels regarding generation of mice overexpressing PTN.

The Sequence Listing is submitted as an ASCII text file in the form of the file named Sequence_Listing.txt, which was created on Sep. 16, 2014, and is 23,178 bytes, which is incorporated by reference herein.

DETAILED DESCRIPTION OF THE INVENTION

The terms "subject" or "individual" refer to members of mammalian animal species and include, but are not limited to, domestic animals, primates and humans; the subject is preferably a male or female human being of any age or race.

The term "neuropsychiatric illness" includes a wide range of undesirable psychiatric and neurological conditions, such as schizophrenia, bipolar disorder, anxiety, major depression, schizoaffective disorder, psychiatric conditions (defined in the DMS IV manual) and neurological illnesses caused by alterations of the central nervous system.

The term "gene" refers to a region of a molecular chain of deoxyribonucleotides that encodes a protein and which could represent the complete coding sequence or a portion of it.

The term "DNA" refers to deoxyribonucleic acid. A DNA sequence is a sequence of deoxyribonucleotides.

The term "RNA" refers to ribonucleic acid. An RNA sequence is a sequence of ribonucleotides.

The term "mRNA" refers to messenger ribonucleic acid, which is the fraction of total RNA that is translated into proteins.

The term "cDNA" refers to a sequence of nucleotides that is complementary to an mRNA sequence.

The phrase "mRNA transcribed from" refers to the transcription of the gene (DNA) into mRNA, as the first step for the gene to be expressed and translated into protein.

The term "nucleotide sequence" refers equally to a sequence of ribonucleotides (RNA) or deoxyribonucleotides (DNA).

The term "protein" refers to a molecular chain of amino acids joined by covalent or non-covalent bonds. This term includes all types of post-translational modification, such as glycosylation, phosphorylation or acetylation.

The terms "peptide" and "polypeptide" refer to molecular chains of amino acids that represent a protein fragment. The terms "protein" and "peptide" are used indistinctly.

The term "antibody" refers to a glycoprotein that displays specific binding to a target molecule, which is termed the "antigen". The term "antibody" includes monoclonal antibodies or polyclonal antisera, either intact or fragments thereof; it includes human, humanised and non-human antibodies. "Monoclonal antibodies" are homogeneous populations of highly specific antibodies that target a unique antigenic site or "determinant". "Polyclonal antisera" include heterogeneous populations of antibodies that target different antigenic determinants.

The term "epitope", as used in the present invention, refers to an antigenic determinant of a protein, which is the amino acid sequence of the protein that a specific antibody recognises.

The term "solid phase", as used in the present invention, refers to a non-aqueous matrix to which an antibody can be bound. Examples of solid phase materials include glass, polysaccharides such as agarose, polyacrylamide, polystyrene, polyvinyl alcohol and silicones. Examples of solid phase forms are the well of a test plate or a purification column.

The terms "oligonucleotide" and "oligonucleotide primer" are used indistinctly and as used in the present invention, refer to nucleotide sequences that are complementary to a nucleotide sequence in the ptn gene. Each primer hybridises with its target nucleotide sequence and acts as a starting point for nucleotide polymerisation catalysed by DNA polymerase, RNA polymerase or reverse transcriptase.

The term "probe", as used in the present invention, refers to a nucleotide sequence that is complementary to a nucleotide sequence derived from the ptn gene and which can be used to detect this nucleotide sequence derived from the ptn gene.

The term "therapeutic target" refers to nucleotide or peptide sequences against which a drug or therapeutic compound can be designed and applied clinically.

The term "antagonist" refers to any molecule that inhibits the biological activity of the antagonised molecule. Examples of antagonists include, amongst others, proteins, peptides, sequence variations of natural peptides and small organic molecules (molecular weights of less than 500 Daltons).

The term "exogenous promoter" as used herein means a promoter other than the PTN gene promoter.

The term "to exhibit depressive symptoms" means, but is by no means limited to, particularly to exhibit an increase in immobility time in the tail suspension test as described below.

The term "to exhibit anxious symptoms" means, but is by no means limited to, particularly to exhibit a reduction in time spent in the open arms in the elevated plus maze as described below.

The term "animal model of mood disorders" means an animal which may be used in detecting an effect of a test substance on the treatment for anxiety and/or depression or screening for an agent for treating anxiety and/or depression.

PTN

As used herein PTN polypeptide may be a native PTN polypeptide from a mammalian species, particularly a mouse, human or rat. PTN protein is also known by the names: HBBM (Heparin-binding brain mitogen), HBGF-8 (Heparin-binding growth factor 8), HB-GAM (Heparin-binding growth-associated molecule), HBNF-1 (Heparin-binding neurite outgrowth-promoting factor 1) and OSF-1 (Osteoblast-specific factor 1). Also encompassed by the term PTN polypeptide as used herein are variants (such as a splice variant), precursors (such as the 168 amino acid human pleiotrophin precursor sequence available at NCBI accession number NP_002816; GI: 4506281 or the 168 amino acid mouse pleiotrophin precursor sequence available at NCBI accession number NP_032999; GI: 6679543), derivatives (such as a post-translationally processed polypeptide) and fragments thereof. The PTN polypeptide or fragment thereof preferably exhibits biological activity, particularly the ability to bind to a cell surface receptor such as Protein Tyrosine Phosphatase beta/zeta (RPTP β/ζ), Anaplastic Lymphoma Kinase Receptor (ALK) or N-Syndecan (SDC3) (for example a cell surface receptor of the same species). The PTN polypeptide may comprise:

(i) a PTN polypeptide having an amino acid sequence having at least 80%, 90%, 95% or 99% amino acid sequence identity to the sequence of SEQ ID NO: 2;
(ii) a PTN polypeptide having the amino acid sequence of SEQ ID NO: 2;
(iii) a PTN polypeptide having an amino acid sequence having at least 80%, 90%, 95% or 99% amino acid sequence identity to the sequence of SEQ ID NO: 4;
(iv) a PTN polypeptide having the amino acid sequence of SEQ ID NO: 4; or
(v) an active fragment of any one of (i)-(iv) having at least 100, 110, 120 or 130 amino acids, wherein said PTN polypeptide of any one of (i)-(iv) or said active fragment of (v) is capable of binding to a cell surface receptor such as Protein Tyrosine Phosphatase beta/zeta (RPTP β/ζ), Anaplastic Lymphoma Kinase Receptor (ALK) or, N-Syndecan (SDC3) (for example a cell surface receptor of the same species).

As used herein a PTN-encoding polynucleotide or similar expression refers to any nucleic acid (DNA or RNA) that encodes a PTN polypeptide as defined herein. Preferred PTN-encoding polynucleotides include those having at least 80%, 90%, 95% or 99% nucleotide sequence identity to the polynucleotide sequence of SEQ ID NO: 1 or 3. Particularly preferred PTN-encoding polynucleotides comprise or consist of a polynucleotide having the polynucleotide sequence of SEQ ID NO: 1 or 3.

Thy1 Promoter

The nucleotide sequence of the mouse wild-type Thy1 gene is shown in FIG. 12 (SEQ ID NO: 5). As used herein the Thy promoter may be a variant or homologue from a non-mouse species, wherein said variant or homologue comprises or consists of a polynucleotide sequence having at least 80%, 90%, 95% or 99% sequence identity to the polynucleotide sequence of SEQ ID NO: 5, or a fragment thereof having promoter activity. Preferably, the Thy1 promoter comprises or consists of a polynucleotide sequence having the polynucleotide sequence of SEQ ID NO: 5.

Neuro-Specific Promoters

Other Neuro-specific promoters (i.e. other than the Thy1 promoter) that find use in accordance with the present invention, for example as alternatives to the Thy1 promoter, include: human or mouse Neuron specific enolase (NSE or ENO2); human or mouse Rhombotin I (LMO1); human or mouse Phosphoglycerate kinase 1 (PGK or PGK11); human or mouse Neurofilament, light polypeptide (NF-L); human or mouse dopamine beta-hydroxylase (DBH); human or mouse Synapsin-1 (SYN1). Further details concerning the neuro-specific promoters are provided in Table 4. In particular, the skilled person is able to determine suitable promoter sequence from the genomic reference sequence details provided in Table 4 (e.g. making use of one or more promoter/regulatory sequence elements from the 5' 10 kb or 5' 100 kb genomic sequence as identified in columns 7 and 8, respectively, of Table 4.

Transgenic Animals

The non-human transgenic animal of the invention is preferably a rodent, most preferably a mouse. A variety of suitable techniques may be used to alter the mouse genome to enhance PTN expression in at least one brain region. Preferably, a vector of the invention is introduced into a non-human embryo. The incorporated polynucleotide encoding a PTN polypeptide and under control of a promoter is preferably transmissible between generations. This facilitates establishment of a colony of transgenic animals. Preferably, genomic incorporation of the polynucleotide is verified by extraction and characterisation of DNA from the transgenic animal and/or its offspring.

Screening Methods and Test Agents

When an agent reduces the expression levels of the ptn gene or reverses the effects due to increased expression of said gene, this agent becomes a candidate for the treatment of neuropsychiatric disorders.

Thus, the invention relates to the use of nucleotide or peptide sequences from the ptn gene in methods to search for, identify, develop and assess the efficacy of compounds to treat neuropsychiatric illnesses, especially mood disorders such as anxiety and/or major depression. The importance of screening methods in the search for drugs based on the binding, competitive or otherwise, of a potential drug molecule to the therapeutic target should be stressed.

Another object of the invention consists of providing agents characterised by their inhibition of the expression and/or activity of the PTN protein. Those agents which can be identified and assessed according to the present invention may be chosen from the group formed by:

a) a specific antibody, or combination of antibodies, against one or more epitopes present in the protein PTN, preferably a human or humanised monoclonal antibody, which can also include an antibody fragment, a simple chain antibody or an anti-idiotype antibody;

b) cytotoxic agents, such as toxins, molecules containing radioactive atoms, or chemotherapy agents, including but not limited to, small organic and inorganic molecules, peptides, phosphopeptides, antisense molecules, ribozymes, siRNAs, triple helix molecules, etc., which inhibit the expression and/or activity of the PTN protein; and c) antagonists of the PTN protein that inhibit one or more functions of said protein.

The present invention also provides a pharmaceutical composition that contains a therapeutically effective quantity of one or more agents identified in a screening method of the invention (in vitro or in vivo method) together with one or more excipients and/or transport substances. Furthermore, said composition may comprise a further active ingredient that inhibits the function of the PTN protein.

The excipients, transport substances and auxiliary substances should be pharmaceutically and pharmacologically acceptable such that they can be combined with other components of the formulation or preparation and they do not cause adverse effects on the treated organism. The pharmaceutical compositions or formulations include those that are appropriate for oral or parenteral (including subcutaneous, intradermal, intramuscular and intravenous) administration, although the best administration route depends on the state of the patient. The formulations can be in the form of simple doses and the formulations are prepared according to known methods in the field of pharmacology. The amounts of active substances to be administered can vary depending on the therapeutic needs.

Diagnostic Methods

Methods of the present invention for assessing the presence of or susceptibility to a neuropsychiatric illness are based on the observation that subjects or individuals diagnosed with neuropsychiatric illnesses, especially mood disorders, such as anxiety and/or depression, present much higher levels of the protein coded for the ptn gene (PTN protein) than the corresponding levels in subjects with no clinical history of these illnesses.

The method presented involves a subject sampling step, and can work with different biological fluids such as, for example: blood, plasma, serum or cerebrospinal fluid. Preferably the sample comprises CNS tissue.

The samples can be taken from subjects previously diagnosed with a given neuropsychiatric illness or from undiagnosed individuals, as well as from a subject receiving treatment or who has been treated previously for a neuropsychiatric illness, particularly mood disorders such as anxiety and/or depression.

The present method may also involve an extraction step, either to obtain the protein extract from the sample or to obtain the total RNA extract.

Any conventional in vitro test can be used for measurement of levels of mRNA transcribed from the ptn gene or its complementary cDNA, or the concentration of the PTN protein, in samples collected from the individuals to be analysed and from control individuals.

Thus, in some cases the present invention provides an in vitro method for detecting the presence of neuropsychiatric illnesses in an individual, especially mood disorders such as anxiety and/or depression, to determine the state or severity of this illness in the individual, or to monitor the effect of a treatment administered to an individual who presents this illness, based either on measuring the concentration of the PTN protein or the expression of the ptn gene.

If the concentration of the PTN protein is to be determined, the method may comprise an initial step where the protein extract from the sample is mixed with one or more specific antibodies against one or more epitopes of the PTN protein, and a second step where the complexes formed between these antibodies and the protein PTN are quantified.

A wide variety of immunological tests can be used to detect the formation of specific antigen-antibody complexes and several competitive and non-competitive protein binding assays have been described previously, a large number of which are available commercially.

Thus, the PTN protein can be quantified with antibodies such as specific monoclonal and polyclonal antibodies, either intact or recombinant fragments thereof, combibodies, and Fab or scFv antibody fragments against the PTN protein. These antibodies can be human, humanised or non-human in origin. The antibodies used in these tests can be labelled or not and the unlabelled antibodies can be used in clumping tests while the marked antibodies can be used in a wide range of tests. The labelling molecules that can be used to label the antibodies include radionuclides, enzymes, fluorophores, chemoluminescent reagents, enzymatic substrates or cofactors, enzyme inhibitors, particles, colorants and derivatives.

A wide range of well-known tests that use unlabelled (primary antibody) and labelled antibodies (secondary antibody) can be used with the invention dealt with here. These techniques include the Western blot or Western transfer, ELISA (Enzyme-Linked immunosorbent assay), RIA (Radioimmunoassay), competitive EIA (competitive enzyme immunoassay), DAS-ELISA (double antibody sandwich-ELISA), immunocytochemical and immunohistochemical techniques, techniques based on the use of biochips or protein microarrays that include specific antibodies or tests based on colloidal precipitation in formats such as dipsticks. Other methods of detecting and quantifying the PTN protein include affinity chromatography techniques, ligand binding tests, mass spectrometry or lectin binding tests.

If the mRNA or cDNA corresponding to the ptn gene is to be detected in addition to or as an alternative to detecting the protein, the method of the invention may comprise extraction of RNA (such as total RNA). The mRNA or cDNA corresponding to the ptn gene is detected by amplifying the total RNA extract or the corresponding cDNA synthesised by reverse transcription from the mRNA template in a first step, followed by a second step that involves quantification of the product amplified from the mRNA or cDNA from the ptn gene.

An example of mRNA amplification consists of reverse transcribing the mRNA into cDNA (RT), and then performing a polymerase chain reaction (PCR) with primer oligonucleotides. PCR is a technique that is used to amplify a certain nucleotide sequence (target) contained in a mixture of nucleotide sequences. PCR uses an excess of a pair of primer oligonucleotides that hybridise with the complementary strands of the target nucleotide sequence. Next, an enzyme with polymerase activity (Taq DNA polymerase) extends each primer by using the target nucleotide sequence as a template. The extension products are then converted into target sequences upon dissociation of the original target strand. New primer molecules then hybridise to them and the polymerase extends them. This cycle is repeated to increase the number of target sequences exponentially and it is a technique described in the U.S. Pat. No. 4,683,195 and U.S. Pat. No. 4,683,202. Many methods for detecting and quantifying the products of PCR amplification, any of which can be used in this invention, have been described previously. In a preferred method of the invention, the amplified product is detected by agarose gel electrophoresis as follows: five microliters of the amplification product is separated by electrophoresis on a 2% agarose gel in a TBE 0.5× buffer at 100 vdc for one hour. After electrophoresis, the gel is stained with ethidium bromide and the amplification product visualised by illuminating the gel with ultraviolet (uv) light. As an alternative to staining and also as a preferred technique, the amplification product can be transferred to a nylon membrane by the Southern blotting technique and detected with a specific, appropriately labelled probe for the cDNA of the ptn gene.

In another example the mRNA is detected by transferring the mRNA to a nylon membrane by transfer techniques such as Northern blot and detection with specific probes for the mRNA or the corresponding cDNA for the ptn gene. In another specific assay, the mRNA corresponding to the ptn gene may be amplified and quantified at the same time by real-time quantitative RT-PCR (Q-PCR).

The method may involve comparing the amount of the PTN protein, the amount of mRNA from the ptn gene or the amount of the corresponding cDNA detected in the sample taken from the subject with the amount of PTN protein, the amount of mRNA from the ptn gene or the amount of the corresponding cDNA detected in samples from one or more control subjects or with one or more pre-determined reference values. An increase of around 10%, preferably 20%, 30%, 50% or greater may indicate the presence of or susceptibility to a neuropsychiatric illness in the subject.

The following is presented by way of example and is not to be construed as a limitation to the scope of the claims.

EXAMPLES

Example 1

Analysis of Brain Tissue Using Microarray Data Analysis

Samples of postmortem prefrontal cortex (Broadmann's Area 9) were obtained at autopsies performed in the Forensic Anatomical Institute, Bilbao, Spain, and stored at −80° C. The study was developed in compliance with policies of research and ethical review boards for postmortem brain studies (Basque Institute of Legal Medicine, Bilbao). Deaths recorded as suicide were subjected to retrospective careful searching for previous medical diagnosis and treatment using examiner's information and records of hospitals and mental health centres. Depressed victims were selected according to the following criteria: suicide by violent method, lifetime diagnosis of Major Depression made according to DSM-IV and DSM-IV-R (American Psychiatric Association. *Diagnostic and Statistical Manual of Mental Disorders*, 4$^{rd}$ edition revised. American Psychiatric Association, Washington D.C., 2000), absence of psychotropic or illegal drugs. Matched controls did not have a psychiatric disorder, were selected on the basis of sex, age and postmortem delay (PMD) and suffered a sudden and unexpected death. In control subjects other drug exposures were minimal (benzodiazepine, salicylic acid, antiarrythmic, diuretics). The groups did not differ statistically for mean age or PMD. A summary of the demographic information of subjects used in this study is shown in FIG. 1.

Total RNA was isolated from brain tissue with TRIZOL Reagent (Invitrogen Co.) as directed by the manufacturer. RNA quality and integrity were verified by measuring the $A_{260/280}$ ratio and on agarose gels. Purified RNA was cleaned with RNeasy Minikit (QIAGEN Inc.), and 10 mg of total RNA were used for cDNA synthesis using SuperScript™ II RNase (Invitrogen Co.). Biotinylated cRNA was synthesised using ENZO BioArray™ HighYield™ Transcript Labeling Kit (Enzo Diagnostics). After in vitro transcription, unincorporated nucleotides were eliminated using RNeasy Minikit columns (QIAGEN Inc.). Fifteen μg of biotinylated cRNA were hybridised to the Human Genome (HG_U133A) GeneChip® (Affymetrix Inc.) and automatically washed and stained using the Fluidics Station 400. The chips were scanned using an Agilent GeneArray Scanner 2500 (Agilent Technologies Inc.). All sample labelling, hybridisation, staining and scanning procedures were carried out using Affymetrix standard protocols. A total of ten samples were individually hybridised to the GeneChips, five from each group. Exclusion criteria for microarray hybridisation included male subjects below age 52 or above age 75, and any sample with PMD above 49 hours.

Scanned microarray data was processed using the algorithms in the Microarray Analysis Suit Software MAS5.0 (Affymetrix). Global scaling was performed to an arbitrary value of 100, and summarised data was imported into GeneSpring 6.1 (Agilent Technologies Inc.). Normalisation procedures were carried out following default options (measurements less than 0.01 were set to 0.01; per chip normalisation to 50$^{th}$ percentile; per gene normalisation to median), and data were filtered in order to remove unreliable measurements. A t-test ($p<0.05$) was conducted to obtain genes that showed a statistical difference of gene expression between the two experimental groups. Fold Change (FC) values were calculated after normalisation to the median of the intensity value of the control group. An arbitrary threshold value of 1 was chosen to select upregulation or downregulation.

After filtering for inconsistent and unreliable data, the remaining 10.906 probe sets were subjected to Analysis of Variance (ANOVA) to determine genes that were differentially expressed. We defined a cutoff p-value of 0.05 to call a probe differentially expressed between the two sample groups studied. 226 probes passed this criterion, 82 of which were found to be upregulated in the experimental group compared to the control group, and 144 were downregulated. Due to sample variability and the small number of biological replicates per group, it was not possible to correct for multiple testing. Nevertheless, we accepted being less stringent at this point, in view of a validation of results using RT-PCR on a larger population. In addition to this, the MAS5.0 Change algorithm was used to select a further set of genes that consistently had an Increase or Decrease call across the different case-control pair wise comparisons, including 62 upregulated sequences and 95 downregulated sequences. Our cutoff criterion was rather relaxed for this analysis, due to variability issues. This method shared only one probe set with the previous method, with no relevance to the biological data mining of the results. The final list of 383 selected genes is showed in table Annex 1.

Example 2

Determination of PTN as a Biological Marker for Depression

Microarray results were investigated using quantitative PCR. Eighty three genes were selected for quantitative PCR to validate their mRNA expression on a larger sample set, by using Low Density Arrays (Annex 2). Seven genes (RPL10, B2M, ENO2, ZFP207, ACTB, GAPDH and NEFH) were selected to be used as reference genes. Validation was carried out using Low Density Arrays (Applied Biosystems) in a total of 40 prefrontal cortex samples (20 case and 20 control samples). This tool allowed the simultaneous interrogation of all the chosen target genes with two replicates for each gene using TaqMan® technology. Briefly, a 384-well microfluidic card is loaded with the selected gene expression assays. Each card is composed of eight sample-loading ports, each connected to 48 reaction wells. One microgram of RNA from each sample was reversed transcribed using a high-capacity cDNA archive kit (Applied Biosystems) and random primers. 25 µl of cDNA are used for preparation of PCR mastermix. Samples are then pipetted into each port. After centrifuging, the card is placed on the 7900HT Fast Real Time PCR System (Applied Biosystems). All protocols followed manufacturer's directions. For signal detection, the ABI Prism 7700 Sequence Detector System was used. The Ct value (cycle number at threshold) was used as a measure of relative amount of mRNA molecules. All measurements were produced in duplicate, and the average of the two was taken for analysis. Duplicates for which the standard deviation was greater than 0.38 where eliminated from the analysis. Data obtained were analysed using geNorm 3.3 software (Vandesompele et al., 2002). geNorm detects the most stable reference genes from the set of tested housekeepings and calculates a gene expression normalisation factor for each sample. The Ct values are transformed to quantities using the ΔCt method and then normalised to the average value of the control group for calculation of Fold Change values. Significant changes were assessed based on an unpaired two-tailed Student t-test on normalized ΔCt values after exporting data into Microsoft Excel®. To account for possible confounding variables, like treatment and matching samples, different analyses were carried out applying different sample exclusion criteria.

Statistical analyses of the Q-PCR results were carried out comparing the group of cases versus their matched controls. This analysis showed 54 genes differentially expressed between cases and controls. The results of the statistical analysis are shown on Annex 3.

Example 3

Validation by Western Blotting of PTN as a Biological Marker for Depression

The levels of PTN protein in human cerebral prefrontal cortex samples (Brodmann area 9) from individuals diagnosed with depression who died by suicide (n=23) and who had (n=11) or who had not (n=12) received antidepressant treatment and control subjects with no history of psychiatric illness who died accidentally (n=23), were validated by Western blotting with an antibody that specifically recognises said protein. The samples from depressive patients were paired with control samples on the basis of sex, age and post mortem delay. Target protein was quantified in pairs of subject with depression and the respective matched control. The relative content of each protein was calculated (percent change) in relation to in-gel triplicate standards (100%, pool of controls samples). This quantification procedure was assessed 2-3 times in different gels, and the resulting mean value of the target protein was used as a final estimate.

Human brain samples (100 mg) were homogenized in cold 50 mM Tris-HCl buffer, pH 7.5, containing various protease inhibitors (Sigma protease inhibitor cocktail 50 µl/g, antipain and chymostatin 10 µl/ml), and phosphatase inhibitors (1 mM cantharidin, 1 mM sodium fluoride, and 1 mM sodium orthovanadate). Then, a mix of detergents (10% igepal, 5% sodium deoxycholate, 1% sodium dodecyl sulfate (SDS), and CHAPS 250 mM) was added and samples were centrifuged at 14,000×g for 10 min. The pellet protein content was determined with the BCA protein assay kit (Pierce, Madrid, Spain) using bovine serum albumin as a standard. Aliquots of this mixture were combined with solubilization loading buffer (25% glycerol, 5% 2-mercaptoethanol, 2% SDS, 0.01% bromophenol blue, and 62.5 mM Tris-HCl, pH 6.8), to reach a final concentration of 2 mg/ml. The mixture was denatures at 95° C. for min, and stored at −80° C. until use.

In routine experiments, 40 mg proteins of each human or control human pool brain sample was subjected to SDS-PAGE on 15% polyacrilamide minigels and proteins were then transferred to nitrocellulose membranes. Membranes were blocked for 1 h with Tris-buffered saline (TBS; 10 mM Tris-HCl, pH 7.4, 140 mM NaCl) containing 3% skimmed milk, and then incubated with one of the primary antibodies at 4° C. overnight (PBS-3% skimmed milk-0.1% Tween buffer). The following primary antibodies were used: PTN (Goat polyclonal antibody anti-Pleiotrophin, product AF-252-PB, lot no. PW07, 1:500 dilution, R&D Systems); Mouse monoclonal antibody anti-β-actin (clone AC-15, lot No. 014K4840, Sigma Chemical Co.) was used for immunodetection at a dilution of 1:5,000 of β-actin protein as a control loading The nitrocellulose membranes were incubated with a fluorescent anti-Goat IgG secondary antibody (IRDye™ 800CW Rabbit, Rockland, Gilbertsville, Pa., USA) and a anti-Mouse IgG secondary antibody (IRDye™ 800CW Rabbit, Rockland, Gilbertsville, Pa., USA) at a dilution of 1:3,000 and 1:5,000 respectively. Finally, the membranes were imaged using the LICOR Odyssey Image System. Duplicate problem samples were evaluated and normalized as percentage of immune reactivity of the respective matched control (see FIG. 2).

A significant increase in the levels of PTN protein was observed in prefrontal cortex samples from depressive subjects when compared with the levels of the same protein in control subjects with no clinical history of psychiatric illness (123±8, n=22, p<0.02). Furthermore, it was found that the expression of PTN protein was much higher in the prefrontal cortex of depressives who had died by suicide and who had not received pharmacological treatment when compared with samples from the same brain region of control individuals with no history of psychiatric illness and who had died accidentally (135±14, n=10, p<0.03). Interestingly, it was found that the PTN levels in depressive subjects who had been treated with antidepressant drugs but who had also died by suicide were lower than those in untreated individuals and were similar to the control levels (112±10, n=12, not significant; FIG. 2).

Example 4

Method of Preparing Transgenic Animal

The polynucleotide to be introduced contains a promoter sequence capable of controlling the expression of the depression-related protein and, if desired, may further contain an enhancer sequence. The depression-related protein may be expressed specifically in the brain. The promoter for preparing the model animal in the present example was specifically chosen. This promoter is the Thy-1 (THYmocyte differentiation antigen 1), also known as CD90, T25 or Thy1.2. The Thy-1 gene is a neuronal gene specifically expressed in neurons. Therefore, a desired gene (in this case PTN) can be selectively expressed in the brain, particularly in neurons, by using the promoter region of a Thy-1 gene. The transgenic mice were found to exhibit anxiety and/or depression symptoms as a result of overexpression of PTN in the brain.

Figure 3B:
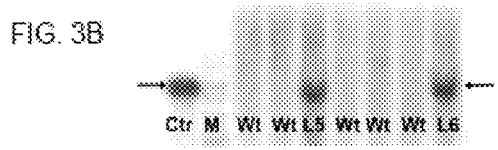

A 1.6 kb EcoR1-XhoI fragment containing the entire coding sequence of the mouse PTN gen (SEQ ID NO: 1) was introduced downstream of the Thy-1 promoter (SEQ ID NO: 5) at XhoI site in the pTSC-a2 plasmid, which contained the regulatory regions responsible for tissue specific expression of Thy-1 gene. Transgenic mice were generated by standard pronucleus microinjection of the 5.8 kb fragment from the Thy1-PTN construct on a hybrid B6/SJL-F1J genetic background (FIG. 3a). Ninety six animals were born, 18 of them carrying the transgene insertion (12♂y 6♀), as analyzed by Southern-blot by using the complete PTN cDNA as a probe. Two transgenic lines were chosen and all of the wild-type controls were littermates of the transgenic mice (L5 and L6) (FIG. 3b).

Figure 3C:
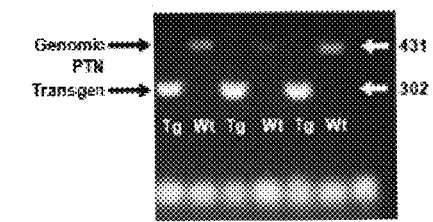

Successful introduction of the gene may be determined by extracting DNA from a part of the body (for example the tail tip) and confirming the presence of the introduced polynucleotide. Animals testing positive for the introduced gene are regarded as founders. The introduced polynucleotide is transmitted to 50% of the offspring, and it is possible to efficiently obtain wild type and mutated animals (FIG. 3c).

The transgenic animal prepared as described above and its offspring exhibiting anxiety and/or depression symptoms are useful in detecting a therapeutic effect on anxiety and/or depression and screening for a therapeutic agent or agents for anxiety and/or depression.

Example 5

PTN Expression Level Determination in the Brain of Transgenic Mice: mRNA and Protein mRNA Quantification:
a) Q-RT-PCR:
Total RNA was extracted with RiboPure™ kit (Ambio, Life Technologies Corporation) and its integrity (RNA integrity number, RIN) measured by the Caliper's RNA LabChip® kit using the Agilent 2100 Bioanalyzer. 600 ng of this purified RNA were used to generate cDNA using High Capacity cDNA Reverse Transcription kit (Applied Biosystem, USA). qRT-PCR was performed with ABI 7500 thermocycler (Applied Biosystem, USA) following manufacturer's instructions, using TaqMan® Inventoried Gene Expression probes (PTN: Mm 00436062_m1; GAPDH: VIC/MGB Probe, AB 4353339E-0909023, Applied Biosystem Life Technologies). GAPDH was used as house-keeping gene and its expression value was used to normalize PTN expression values. For expression quantification Pfaffl's $2^{-\Delta\Delta CT}$ method was used, assuming a 100% PCR efficiency.

Figure 3D:
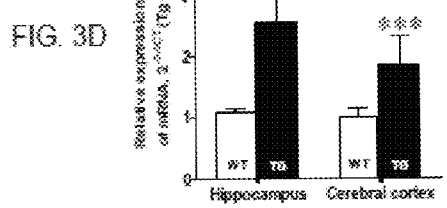

The results showed a significant increase of PTN expression levels in the hippocampus and cerebral cortex of transgenic mice of L5 compared to their wild-type littermates (FIG. 3d).

b) In Situ Hybridization:
Three different oligonucleotides were designed and synthesized, complementary to different domains of the PTN mRNA:

Oligo 1:
(SEQ ID NO: 6)
AGTGTCCACAGCTGCCAAGATGAAAATCAATGCAGGAAGGCAGCTGC;

Oligo 2:
(SEQ ID NO: 7)
ACTCGGCGCCAGTGCGAGTGCCCTCCCGGGTGCCCAATCCACAGTCC;

Oligo 3:
(SEQ ID NO: 8)
AGGCTTGGGCTTGGTGAGCTTGCCACAGGGCTTGGAGATGGTGACAG.

They were labeled with $^{33}$P-dATP and used separately to hybridize tissue sections. The 3 independent probes gave the same hybridization pattern (data not shown). We next used them to analyze the expression pattern of the PTN mRNA in the PTN transgenic mice and compared it with that of wild-type brains. An example of four different brain levels in 1 wt and 1 transgenic mice brains is shown in FIG. 3f, obtained from the autoradiograms. In general the expression can be seen in many neurons in different brain areas (see hippocampus and cerebral cortex), although some expression in white matter areas cannot be excluded.

Autoradiograms for each hybridized probe were semi-quantified with an MCID™ system and relative optical densities (ROD) were obtained. Measurements for PTN mRNA from 3 Wt and 3 TG mice are presented in FIG. 4 where TG/WT ratio confirms PTN overexpression, mostly in hippocampal fields such as CA3 area (4-6-fold), CA1 and dendate gyrus (around 2.5-fold).

Protein Quantification:
a) Western Blot:
Proteins were obtained from the organic phase of the previously described TRI Reagent mRNA extraction. After ethanol addition, samples were centrifuged at 4.600 rpm for 5 min at 4° C. The supernatant was transferred to a new tube, incubated with isopronanol for 10 min at RT, and centrifuged at 12,000 g for 10 min at 4° C. After washing the pellet three times with guanidine hydrochloride in 95% ethanol, it was disaggregated with a manual homogenizer for 30 sec and incubated for 10 min at RT. Every sample was centrifuged for 5 min at 8,000 g at 4° C., the pellet disaggregated in 100% ethanol, incubated 20 min at RT and centrifuged again for 5 min at 8,000 g at 4° C. Dry pellet was solubilized in 4M Urea in 1% SDS at 40° C. for 15-20 min and centrifuged for 10 min at 10,400 g at 4° C. The total protein concentration of each sample was determined by Bio-Rad DC™ Protein Assay. Protein lisates were mixed with Laemmli sample buffer (5×) for a final protein concentration of 1 µg/ml, heated for 5 min at 100° C. and centrifuged for 5 min at 3,000 rpm at 4° C.

Gel electrophoresis was carried out in 12.5% sodium dodecyl sulfate (SDS)-polyacrilamide gels and resolved proteins were transferred to PVDF membranes, which were blocked with 5% skimmed milk to avoid nonspecific binding. Membranes were incubated in the following primary antibodies: goat anti-PTN (1:300) from R&D systems, Inc. (AF-252-PB) and mouse anti-GAPDH (1:2,000) from Santa Cruz Biotechnology, Inc. Heidelberg, Germany (SC-32233). After extensive washings in TBS-T (TBS/0.05% Tween 20), membranes were incubated with the following horseradish peroxidase conjugated secondary antibodies: rabbit anti-goat IgG (1:50, 000) and goat anti-mouse IgG (1:50,000), both from Sigma-Aldrich Co., Missouri, USA. Secondary antibodies were detected with ECL Advance kit (GE Healthcare Europe GmbH, Munich, Germany). Blot quantifications were performed by densitometric scanning using Scion Image Software. The densitometry values were normalized with respect to the values obtained with anti-GAPDH antibody. Data are expressed as mean±standard error.

Figure 3E:
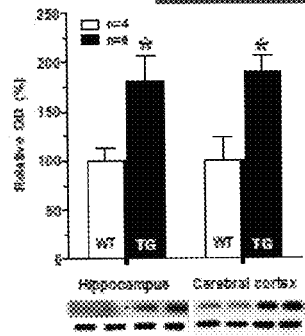
Figure 3F:
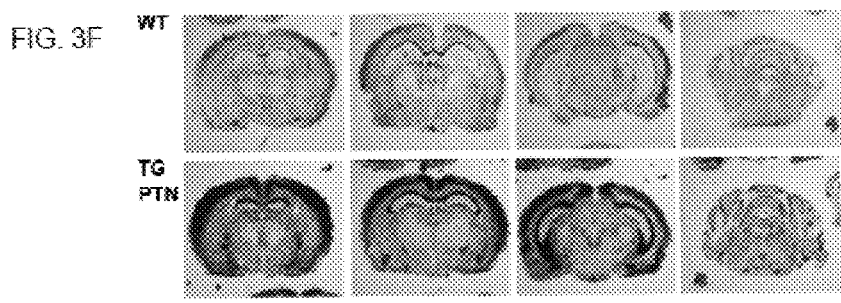
Figure 5A:
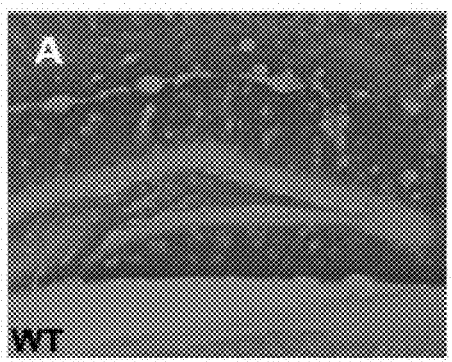
FIGS. 5A-5D illustrate immunohistochemistry experiments for PTN in hippocampus (FIGS. 5A and 5B) and cerebral cortex region (FIGS. 5C and 5D) of the brain in control (FIGS. 5A and 5C) and in transgenic mice (FIGS. 5B and 5D).
Figure 5B:
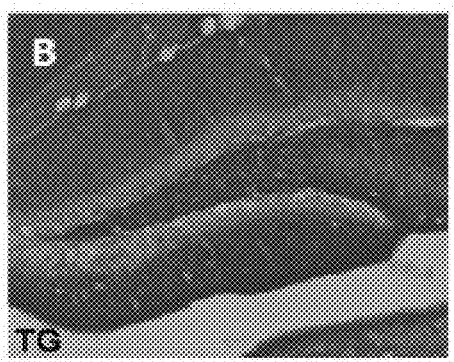
Figure 5C:
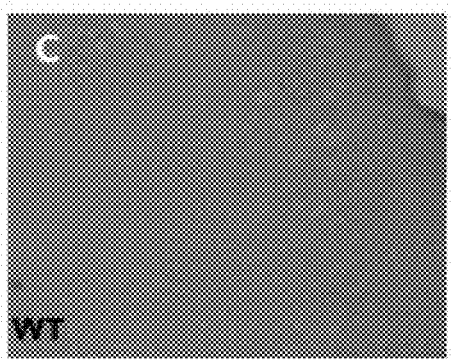
Figure 5D:
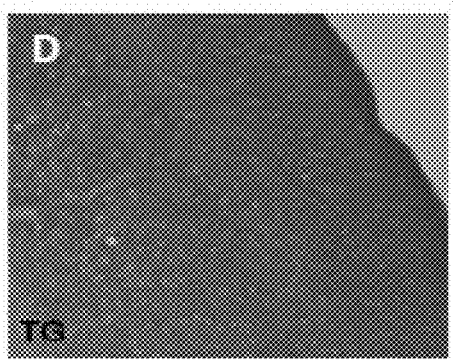

An increase in PTN expression levels in the hippocampus (181±25, n=6, p<0.05) and cerebral cortex (190±16, n=6, p<0.05) of transgenic mice were shown (FIG. 3e).

b) Immunohistochemistry:

Male mice were anesthetized with 0.2 ml pentobarbital (50 mg/kg) and transcardially perfused (1: 75 ml NaCl 0.9%; 2: 75 ml paraformaldehyde 4%). After brain extraction, 4 hour post-fixation was carried out with paraformaldehyde 4% and the brains were incubated in sacarose 30% for 36 hours. Once dry and frozen, 40 μm coronal sections were cut along the hippocampus and the cerebral cortex. Immunohistochemistry was performed as following standard protocols and the following antibodies were used: goat anti-PTN primary antibody (1:200) from R&D Systems (Ref. AF-252-PB) and donkey anti-goat secondary biotinylated antibody (1:200) from Jackson Immunoresearch (Ref. 705-065-147). PTN labeled regions give rise to a DAB precipitate when analyzed under Carl Zeiss Axioskop 2 Plus optic microscope.

Transgenic animals show a higher intensity signal of PTN expression, compared to their wild-type littermates, both in the hippocampus and the cerebral cortex (FIG. 5).

Example 6

Behavioural Testing

It is possible to detect whether or not a transgenic mouse shows anxious and/or depressive symptoms by conventional methods of measuring anxiety and/or depression-related disorders, such as the following methods described in items 1) to 4):

1) General Observation: Irwin Test Adaptation

A general observation of animal behavior was carried out, such as measurements of weight, rectal temperature, excitation, fear and jumping response to touch, vocalization to touch, aggressiveness, tremor, motor tics, respiratory rate and ptosis.

These observations were performed 5 min after placing the animals in a transparent box (20×20×30 cm) with 50 lux light illumination.

No significant differences were detected in animal's weight and rectal temperature between wild-type and transgenic mice. FIG. 6 summarizes the results obtained for the rest of the characteristics studied.

These results suggest that PTN-OE mice are more prone to be reactive to external stimuli, and they show a higher level of excitation than wild-type mice.

2) Motor Activity-Open Field Test:

The objective of this experiment was to evaluate the possible influence of the locomotor responses in the behavioral phenotype of transgenic mice overexpressing PTN. For this purpose, locomotor activity was evaluated in wild-type and PTN-OE mice under non-stressful conditions using locomotor activity boxes (FIG. 7a-c) and under stressful conditions using a high-illuminated open field (FIG. 7d-i).

Locomotor Activity Boxes:

Spontaneous horizontal and vertical locomotor activities were measured during three consecutive days under non-stressful conditions by using individual small Plexiglas activity boxes (9×20×11 cm, Imetronic, France). Each box contained a line of photocells 2 cm above the floor to measure horizontal locomotor activity, and another line located 6 cm above the floor to measure vertical activity (rearing). Mice were placed in the boxes and total activity, horizontal activity and number of rearings were recorded during 30 min in a low luminosity environment (20±25 lux). Data obtained in the locomotor activity boxes were analyzed by using a two-way analysis of variance (ANOVA) with genotype (wild-type or transgenic) as between-subjects factor and day as within-subject factor. Differences were considered significant at P<0.05. All results are expressed as mean±S.E.M. The statistical analysis was performed using SPSS software version 15.0 (SPSS Inc., Chicago, Ill., USA).

Total activity, horizontal activity and number of rearings were evaluated in wild-type and transgenic mice overexpressing PTN during three consecutive days in the locomotor activity boxes. Two-way ANOVA revealed a significant effect of day [$F_{(2,74)}$=71.68, P<0.001] on total activity, whereas non-significant effects of genotype [$F_{(1,37)}$=0.09, n.s] nor interaction between day and genotype [$F_{(2,74)}$=2.32, n.s.] were obtained (FIG. 7a). Similarly, two-way ANOVA revealed a significant effect of day [$F_{(2,74)}$=66.41, P<0.001] on horizontal locomotor activity, without effect of genotype [$F_{(1,37)}$=0.03, n.s], nor interaction between both factors [$F_{(2,74)}$=0.40, n.s.] (FIG. 7b). In agreement, two-way ANOVA revealed a significant effect of day [$F_{(2,74)}$=50.96, P<0.001] on vertical activity, without significant effect of genotype [$F_{(1,37)}$=0.55, n.s], nor interaction between both factors [$F_{(2,74)}$=0.78, n.s.] (FIG. 7c). These results indicate that both wild-type and transgenic mice similarly decreased locomotor activity across days, as a result of the expected habituation to the new environment. Interestingly, wild-type and transgenic mice showed similar responses on all the locomotor parameters evaluated under these non-stressful conditions suggesting that the basal locomotor activity is similar in both genotypes.

Open Field:

Locomotor activity was also evaluated under stressful conditions by using an open field. The open field was a white rectangular area (70 cm wide, 90 cm long and 60 cm high) brightly illuminated from the top (500 lux). A total of 63 squares (10×10 cm) were drawn with black lines on the white floor of the field. Six events were recorded during an observation period of 5 min: time spent in central area, crossing squares in central area, entries in central area, crossing squares in peripheral area, number of rearings and number of groomings. Data obtained in the open field were analyzed by using a one-way ANOVA with genotype (wild-type or transgenic) as between-subjects factor. Differences were considered significant at P<0.05. All results are expressed as mean±S.E.M. The statistical analysis was performed using SPSS software version 15.0 (SPSS Inc., Chicago, Ill., USA).

The following behavioural responses were evaluated in the open field: time spent in central area, crossing squares in central area, entries in central area, crossing squares in peripheral area, number of rearings and number of groomings. One-way ANOVA revealed a significant effect of genotype on the time spent in the central area [$F_{(1,37)}$=8.23, P<0.01], crossing squares in the central area [[$F_{(1,37)}$=6.31, P<0.05] and number of gromings [$F_{(1,37)}$=6.24, P<0.05]. Indeed, transgenic mice spent lower time in the central area, lower number of crossing squares in the central area and higher number of groomings than wild-type mice (FIGS. 7d, e and h). An enhanced grooming behaviour and a decreased exploration of the central area under these stressful conditions would reflect an enhanced anxiety-like behaviour in these transgenic mice. In agreement with the results obtained in the locomotor activity boxes, one-way ANOVA did not show significant differences between genotypes on crossing squares in the peripheral area [$F_{(1,37)}$=1.95, n.s] and total number of rearings [$F_{(1,37)}$=0.07, n.s] (FIGS. 4g and i). These two parameters mainly reflect basal locomotion and exploration under these experimental conditions, suggesting that locomotor responses are not modified in the transgenic mice. Furthermore, one-way ANOVA did not reveal significant differences between genotypes on the number of entries in the central area [$F_{(1,37)}$=0.01, n.s] (FIG. 4f). Taken together, the results in this behavioural paradigm suggest that basal locomotor responses are not modified in transgenic mice under stressful conditions, whereas these mice exhibited an anxiety-like behavior.

3) Assessment of Anxiety-Like Behaviours

Elevated Plus Maze

The elevated plus-maze consists of a black Plexiglas apparatus with four arms (16 cm long×5 cm wide) set in cross from a neutral central square (5×5 cm). Two opposite arms are delimited by vertical walls (closed arms), while the two other opposite arms have unprotected edges (open arms). The maze is elevated 40 cm above the ground and placed in indirect light (100 Lux) at 22° C. At the beginning of the 5 min observation session, each mouse is placed in the central neutral zone, facing one of the open arms. The total numbers of visits to the closed and open arms, and the time spent in the closed and open arms, are then observed on a monitor through a videocamera system (ViewPoint, France). The maze was cleaned between sessions using 70% ethanol.

In the elevated plus maze, transgenic mice spent less time and they walked less distance in the open arm compared to their wild-type littermates, (the two-tailed one-sample t-test, p<0.002 and p<0.05 respectively) (FIGS. 8b and 8c). Similarly, transgenic mice showed a decrease but not statistically significant, in the number of entries when compared with wild-type (the two-tailed one-sample t-test, p=0.06) (FIG. 8a). These data are indicative of an anxiety-like behaviour.

Light-Dark Box

The box consists of a small (15×20×25 cm) dimly lit (5 lux) compartment, with black walls and a black floor, connected by a 4 cm long tunnel leading to a larger compartment (30×20×25 cm) intensely lit (500 lux) with white walls and white floor. Lines are drawn on the floor of both compartments to allow measurement of locomotor activity by counting the number of squares (5×5 cm) crossed. Floor lines separate the lit compartment into three equal zones, from the tunnel to the opposite wall, designated as proximal, median and distal zone. Each animal is placed in the dark compartment facing the tunnel at the beginning of the observation session. Latency to go for the first time to the lit compartment, time spent, number of squares crossed and number of visits into each zone of the lit compartment are recorded for 5 min through a videocamera system (ViewPoint, France).

PTN over-expressing transgenic animals avoided facing the lit compartment of the box (the two-tailed one-sample t-test, p<0.05) (FIG. 8e) and showed a decrease in the number of squared crossed (the two-tailed one-sample t-test, p=0.06) (FIG. 8f). No changes were found in the latency to go for the first time to the lit compartment (FIG. 8d). Considering as variables both, zone and genotype, significant differences were found between zone visits (two-way Anova, F(2,108)=17.93) and the interaction genotype-zone (two-way Anova, F(4,108)=2.533) (FIG. 8g).

4) Assessment of Depressive-Like Behaviours

Tail Suspension Test (TST)

Mice are individually suspended by adhesive tape, 1 cm from the tip of the tail 50 cm above a bench top for a 6 min period. The time that the animal is totally inactive during this period is recorded.

Transgenic animals spent more time immobile than their wild-type littermates (the two-tailed one-sample t-test, p<0.05) (FIG. 8h, suggesting a depressive-like behavior.

Sucrose Intake Test

Mice are habituated for 2 days to drink a sucrose solution (1% sucrose in water in graduated feeding bottles with an anti-dripping system). 24 hours after drinking deprivation, the amount of sucrose intake is recorded for 1 hour.

Transgenic mice tend to intake less amount of sucrose compared to their wild-type littermates, although differences are not statistically significant (the two-tailed one-sample t-test, p=0.1) (FIG. 8i). A lower intake could indicate anhedonia, which is a feature related to depressive-like behaviors.

Example 7

Long Term Potentiation (LTP)

We wished to analyze the involvement of PTN in the induction and maintenance of the LTP in hippocampal slices from transgenic and wild-type animals.

All the animals used for this study were killed by decapitation. Immediately after decapitation, animal brains were removed and dropped into a bubbled (95% O2 and 5% CO2) and ice-cold Krebs-Ringer bicarbonate (KRB) solution containing, in mM; 109 NaCl, 2.5 KCl, 1 $KH_2PO_4$, 1.3 $MgSO_4$, 2.5 $CaCl_2$, 26.2 $NaHCO_3$ and 11 glucose. As it has been previously described (del Olmo et al., 2003), transverse slices (400 μm) of each hippocampus were cut with a manual tissue chopper and placed in a humidified interface chamber at room temperature (20-25° C.). After 2-h incubation period, slices were transferred to the submersion recording chamber in which it was continuously perfused with a standard KRB solution at 1.8-2 ml/min rate. Field excitatory postsynaptic potentials (fEPSPs) were recorded for 80 min in CA1 stratum radiatum with tungsten electrodes (1 MΩ) and evoked by stimulating Schaffer collateral-commisural fibers with biphasic electrical pulses (30-70 μA; 100 μs; 0.033 or 0.066 Hz) delivered through bipolar tungsten insulated microelectrodes (0.5 MΩ). The recording electrode was connected to an AI-402 amplifier (Axon Instruments, USA) plugged to a CyberAmp 320 signal conditioner (Axon Instruments, USA). Electrical pulses were supplied by a pulse generator Master 8 (AMPI, Israel). Evoked responses were digitized at 25-50 Hz using a Digidata 1320A (Axon Instruments, USA) and stored on a Pentium IV IBM compatible computer using pCLAMP 9.0 software (Axon Instruments, USA).

The Schaffer collateral groups of axons contacting over the population of cells were stimulated every 15 s. After obtaining stable synaptic responses for at least 20 min (baseline period), CA1 area was tetanized with three 100 Hz pulses for 1 s and 100 μs of duration every 20 sec (HFS). The synaptic strength was assessed by measuring the initial slope of the fEPSP that was analyzed by means of pCLAMP 9.0 software. Data were normalized with respect to the mean values of the responses obtained by each animal at the 20 min baseline period. A single slice from each separate animal was considered as n=1. All electrophysiological experiments were carried out at 31-32° C.

The averaged values of the initial slope of the fEPSP were analyzed by a repeated measure ANOVA. Unpaired t-tests were performed for assessing specific group differences in the average of the fEPSP measured during 5 consecutive minutes at different times of the recording assay. In all the cases, statistical differences were considered significant if the probability of error was less than 5%. All calculations were performed using SPSS statistical package 15.0 version.

Figure 9:
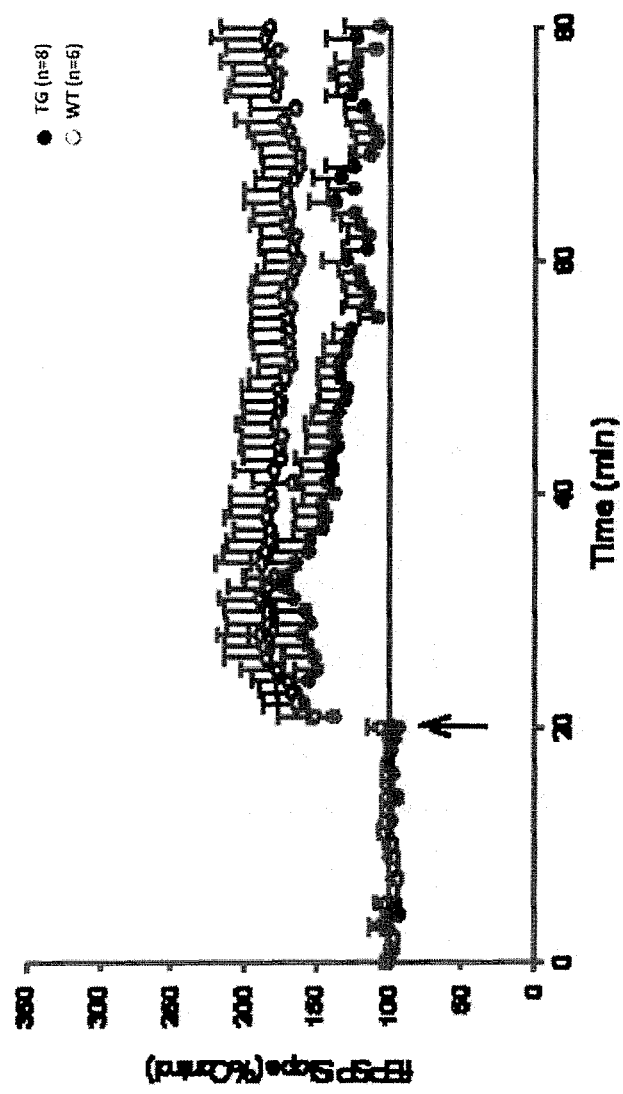
FIG. 9.—LTP induced in hippocampal slices of transgenic PTN mice. Attenuated LTP in mice overexpressing PTN. The symbols represent fEPSP slope values in hippocampal slices from CA1. After a basal 20 min period, 3 trains of HFS (indicated by arrow) were applied in PTN transgenic mice (●, n=8) and control slices (○, n=6).
Figure 15:
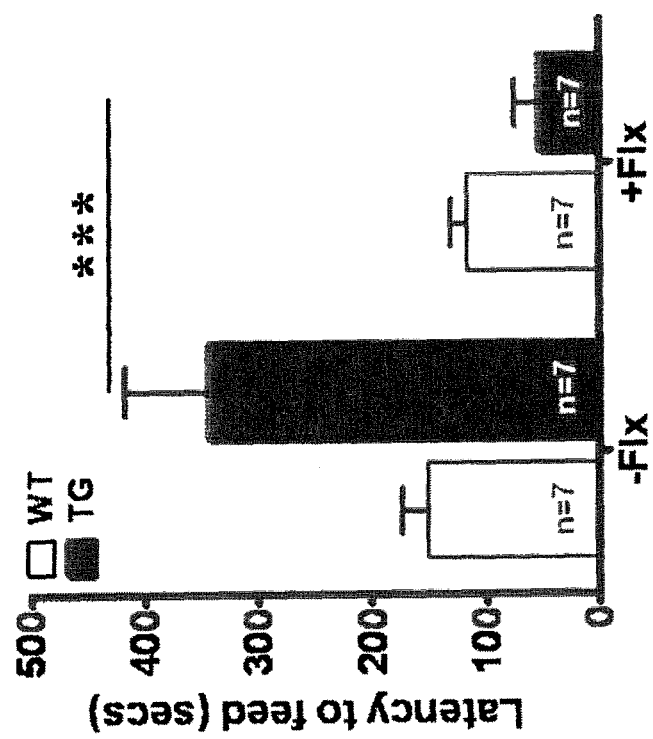
FIG. 15.—Anxiety-like responses and sensitivity to chronic Fluoxetine treatment assessment by Novelty Suppressed Feeding Test. Latency to feed (in seconds) is shown on the y-axis for wild-type (WT; open bars) and transgenic (TG; black bars) mice, for untreated (−Flx) and treated with fluoxetine (+Flx); (n=14, wild-type and n=14, transgenic); ***$p<0.0002$.
Figure 16:
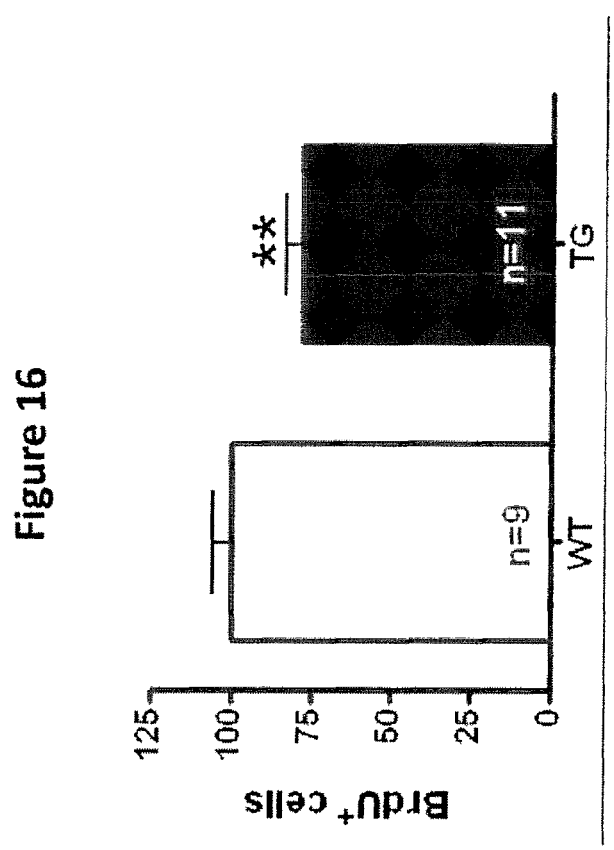
FIG. 16.—Neurogenesis. Number of bromodeoxyuridine (BrdU) positive cells in wild-type (WT) and transgenic (TG) mice.

PTN over-expressing mice presented important deficits in LTP establishment. After HFS application, fEPSP slope increase was identical in both groups (no statistical differences in the potentiation in the 5 minutes alter HFS application). Nevertheless, transgenic PTN mice did not maintain the potentiation until the end of the recording. These results indicate that this mice line presented the impairment of LTP maintenance respect to control (F[1,58]=16,67; p<0.001 from HFS application until the final of the recording) (FIG. 9).

These results may suggest deficits in processes involved in the maintenance of the phenomenon, such us protein synthesis. This could end up in long term memory problems.

Example 8

Method of Screening Agents as Potential Anxiety and/or Depression Therapeutics

A potential therapeutic agent for the treatment of anxiety and/or depression can be tested by administering the test substance to a transgenic animal of the invention. Following the administration of the substance, the behavioural tests (for example behavioural tests as disclosed in Example 6 above) are repeated, in order to evaluate whether the compound modifies the results observed prior to administration of the compound. Preferably, the one or more behavioural tests are additionally performed on one or more untreated transgenic animals of the invention to act as controls.

A potential therapeutic agent may be classified as a candidate for further investigation on the basis of a positive screening result. A positive screening result may be one in which the test agent is found to restore or normalise a behavioural outcome of an animal of the invention to or towards the behavioural outcome of a normal animal (e.g. an animal not having altered levels of PTN but otherwise identical to the animal of the invention). In some cases, the behavioural outcome may be quantified and the degree of restoration or normalisation of the behavioural outcome measured. In this way a pre-determined threshold level may be set to allow classification of an agent being screened as positive or negative for restoration or normalisation of behaviour. Agents classified as positive in this way may then be subjected to further animal testing and/or human clinical testing for safety and/or efficacy in the treatment of a psychiatric illness, e.g. anxiety and/or depression.

The substances which can be used for the screening method are not limited, but may include for example: commercially available compounds (GSK-1838705A (Sabbatini et al., 2009); Crizotinib (Christensen et al., 2007); Imatinib (Heinrich et al., 2003)), various known compounds registered in compound databases (Huang et al., 2003), compounds obtained by combinatorial chemical files, compounds obtained by combinatorial chemistry techniques, or chemically or biologically modified compounds derived from other compounds, culture supernatants of microorganisms, natural components derived from plants or marine organisms, animal tissue, interference RNA (Calvet et al., 2006; Yao et al., 2011), peptides (Hamma-Kourbali et al., 2008; Diamantopoulou et al., 2010; Mikelis et al., 2011), splice forms (Lorente et al., 2005) and antibodies (Chen et al., 2007). Preferably, the agent is a compound capable of passing through the blood-brain barrier (BBB) such that it is "centrally active".

Preferably, one or more positive control compounds, which are known to have therapeutic activity in the treatment of psychiatric illness, particularly depression, are used in the screening method as a reference against which to compare the effects of any test agent. Preferred positive control compounds include Tricyclic Antidepressant such as Imipramine and Amitriptiline; Selective Serotonin Reuptake inhibitors (SSRI) such as Fluoxetine, Paroxetine, Sertraline, Citalopram, Dapoxetine, Escitalopram, Fluvoxamine and Vilazodone; Serotonin noradrenaline reuptake inhibitors (SNRI) such as Duloxetine and Velafaxine.

Example 9

Novelty Suppressed Feeding Test Assesses Anxiety and/or Depression

Novelty suppressed feeding test assesses anxiety and/or depression by measuring the latency of an animal to approach and eat food in a novel environment following chronic treatment with antidepressants. Mice (WT=14 and TG=14) were separated in two experimental groups: Without fluoxetine treatment and with fluoxetine treatment. The Fluoxetine was delivered ad libitum in the drinking water at a concentration of 160 mg/l (approximately doses of 20-25 mg/kg/day) during 4 weeks. Mice were weighed and food was removed from their cage. Twenty four hr after removal of food, mice were transferred to the testing room, placed in a clean holding cage and allowed to habituate for at least 30 min. The testing apparatus consisted of a clear Plexiglas open-field (50×50×25 cm) under an aversive condition (100 lux luminosity). The floor was covered with 2 cm of corncob bedding. A small piece of mouse chow was placed in the center of the arena. At the start of the experiment, each mouse was placed in the corner of the testing area, and the time to the first feeding event was recorded. After all mice from a single cage were tested, mice were returned to their home cage. A longer latency to feed reflects an anxiety-like behaviour.

Evaluation of homogeneity of variance (Levene's test) showed that this assumption is violated, thus a rank transformation was applied on data. Measurement of Latency to feed were rank-transformed (Conover and Iman, 1981) and subjected to a Two-way ANOVA having two levels of genotype (wild-type or WT and transgenic or TG) and two levels of treatment (without fluoxetine or −Flx and with fluoxetine or +Flx). The main effect of genotype was not significant ($F_{(1,24)}$=0.001, n.s.). However, the main effect of treatment was significant ($F_{(1,24)}$=21.080, P=0.00012). In addition to this, there is a significant interaction between the two factors ($F_{(1,24)}$=7.624, P=0.011).

In base to results that show a positive interaction between treatment and genotype, rank-transformed data were submitted to One-way ANOVA to study the effect of treatment on genotype. No significant differences ($F_{(1,24)}$=1.675, n.s.) were found in WT when comparing treated versus untreated samples, while a significant difference was found in TG mice ($F_{(1,24)}$=27.029, P<0.00003). The differences between genotypes in the treated ($F_{(1,24)}$=3.901, P=0.06) or the untreated group (($F_{(1,24)}$=3.724, P=0.07) were not significant, but both comparison showed a trend to increase the latency to feed when compare with WT.

The results showed that PTN overexpression in mouse brain induce anxiety-like responses that are reversed after a chronic treatment with Fluoxetine. Furthermore, Tg mice were more sensitive to the effect of Fluoxetine when compared with Wt.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

TABLE 1

Final list of 383 selected genes

| Affymetrix ID | Gene Title | Gene Symbol | FC DEP |
|---|---|---|---|
| 208047_s_at | NGFI-A binding protein 1 (EGR1 binding protein 1) | NAB1 | 0.37 |
| 217663_at | zinc finger protein 234 | ZNF234 | 0.44 |
| 220122_at | multiple C2-domains with two transmembrane regions 1 | MCTP1 | 0.46 |
| 218326_s_at | leucine-rich repeat-containing G protein-coupled receptor 4 | LGR4 | 0.49 |
| 202203_s_at | autocrine motility factor receptor | AMFR | 0.50 |
| 202478_at | tribbles homolog 2 (*Drosophila*) | TRIB2 | 0.52 |
| 202666_s_at | actin-like 6A | ACTL6A | 0.54 |
| 201816_s_at | glioblastoma amplified sequence | GBAS | 0.54 |
| 206652_at | zinc finger protein 237 | ZNF237 | 0.54 |
| 201424_s_at | cullin 4A | CUL4A | 0.57 |
| 213067_at | myosin, heavy polypeptide 10, non-muscle | MYH10 | 0.57 |
| 201601_x_at | interferon induced transmembrane protein 1 (9-27) | IFITM1 | 0.60 |
| 209298_s_at | intersectin 1 (SH3 domain protein) | ITSN1 | 0.60 |
| 221920_s_at | mitochondrial solute carrier protein | MSCP | 0.60 |
| 210383_at | sodium channel, voltage-gated, type I, alpha subunit | SCN1A | 0.60 |
| 215772_x_at | succinate-CoA ligase, GDP-forming, beta subunit | SUCLG2 | 0.60 |
| 209116_x_at | hemoglobin, beta /// hemoglobin, beta | HBB | 0.61 |
| 209684_at | Ras and Rab interactor 2 | RIN2 | 0.61 |
| 207996_s_at | chromosome 18 open reading frame 1 | C18orf1 | 0.62 |
| 217232_x_at | hemoglobin, beta | HBB | 0.62 |
| 221760_at | Mannosidase, alpha, class 1A, member 1 | MAN1A1 | 0.62 |
| 206935_at | protocadherin 8 | PCDH8 | 0.62 |
| 216769_x_at | Chromosome 9 open reading frame 150 | C9orf150 | 0.63 |
| 213212_x_at | golgin A6 family-like 4 | GOLGA6L4 | 0.63 |
| 211696_x_at | hemoglobin, beta /// hemoglobin, beta | HBB | 0.63 |
| 222240_s_at | myo-inositol 1-phosphate synthase A1 | ISYNA1 | 0.63 |
| 215791_s_at | Intersectin 1 (SH3 domain protein) | ITSN1 | 0.63 |
| 209034_at | proline-rich nuclear receptor coactivator 1 | PNRC1 | 0.63 |
| 202964_s_at | regulatory factor X, 5 (influences HLA class II expression) | RFX5 | 0.63 |
| 209648_x_at | suppressor of cytokine signaling 5 | SOCS5 | 0.63 |
| 87100_at | Abhydrolase domain containing 2 | ABHD2 | 0.64 |
| 210066_s_at | aquaporin 4 | AQP4 | 0.64 |
| 213018_at | GATA zinc finger domain containing 1 | GATAD1 | 0.64 |
| 217414_x_at | hemoglobin, alpha 2 | HBA2 | 0.64 |
| 209316_s_at | HBS1-like (*S. cerevisiae*) | HBS1L | 0.64 |
| 211990_at | major histocompatibility complex, class II, DP alpha 1 | HLA-DPA1 | 0.64 |
| 218578_at | hyperparathyroidism 2 (with jaw tumor) | HRPT2 | 0.64 |
| 219564_at | potassium inwardly-rectifying channel, subfamily J, member 16 | KCNJ16 | 0.64 |
| 212942_s_at | KIAA1199 | KIAA1199 | 0.64 |
| 214658_at | transmembrane emp24 protein transport domain containing 7 | TMED7 | 0.64 |
| 221645_s_at | zinc finger protein 83 (HPF1) | ZNF83 | 0.64 |
| 204273_at | endothelin receptor type B | EDNRB | 0.65 |
| 218053_at | formin binding protein 3 | FNBP3 | 0.65 |
| 203222_s_at | transducin-like enhancer of split 1 (E(sp1) homolog, *Drosophila*) | TLE1 | 0.65 |
| 204520_x_at | bromodomain containing 1 | BRD1 | 0.66 |
| 201842_s_at | EGF-containing fibulin-like extracellular matrix protein 1 | EFEMP1 | 0.66 |
| 209341_s_at | inhibitor of kappa light polypeptide gene enhancer in B-cells, kinase beta | IKBKB | 0.66 |
| 201243_s_at | ATPase, Na+/K+ transporting, beta 1 polypeptide | ATP1B1 | 0.67 |
| 201617_x_at | caldesmon 1 | CALD1 | 0.67 |
| 202653_s_at | membrane-associated ring finger (C3HC4) 7 | MARCH7 | 0.67 |
| 208993_s_at | peptidyl-prolyl isomerase G (cyclophilin G) | PPIG | 0.67 |
| 211074_at | Folate receptor 1 (adult) | Hs.73769 | 0.68 |
| 214071_at | Metallophosphoesterase 1 | MPPE1 | 0.68 |
| 206552_s_at | tachykinin, precursor 1 (substance K, substance P, neurokinin 1, neurokinin 2, neuromedin L, neurokinin alpha, neuropeptide K, neuropeptide gamma) | TAC1 | 0.68 |
| 209386_at | transmembrane 4 L six family member 1 | TM4SF1 | 0.68 |
| 222316_at | Vesicle docking protein p115 | VDP | 0.68 |
| 219376_at | zinc finger protein 322B | ZNF322B | 0.68 |
| 210067_at | aquaporin 4 | AQP4 | 0.69 |
| 202425_x_at | protein phosphatase 3 (formerly 2B), catalytic subunit, alpha isoform (calcineurin A alpha) | PPP3CA | 0.69 |
| 209466_x_at | pleiotrophin (heparin binding growth factor 8, neurite growth-promoting factor 1) | PTN | 0.69 |
| 205651_x_at | Rap guanine nucleotide exchange factor (GEF) 4 | RAPGEF4 | 0.69 |
| 212451_at | SECIS binding protein 2-like | SECISBP2L | 0.69 |
| 201123_s_at | eukaryotic translation initiation factor 5A | EIF5A | 0.70 |
| 219445_at | glioma tumor suppressor candidate region gene 1 | GLTSCR1 | 0.70 |
| 218604_at | LEM domain containing 3 | LEMD3 | 0.70 |
| 218049_s_at | mitochondrial ribosomal protein L13 | MRPL13 | 0.70 |
| 213725_x_at | xylosyltransferase I | XYLT1 | 0.71 |

TABLE 1-continued

Final list of 383 selected genes

| Affymetrix ID | Gene Title | Gene Symbol | FC DEP |
|---|---|---|---|
| 221008_s_at | alanine-glyoxylate aminotransferase 2-like 1 /// alanine-glyoxylate aminotransferase 2-like 1 | AGXT2L1 | 0.72 |
| 212224_at | aldehyde dehydrogenase 1 family, member A1 | ALDH1A1 | 0.72 |
| 214553_s_at | cyclic AMP phosphoprotein, 19 kD | ARPP-19 | 0.72 |
| 206253_at | discs, large homolog 2, chapsyn-110 (*Drosophila*) | DLG2 | 0.72 |
| 201667_at | gap junction protein, alpha 1, 43 kDa (connexin 43) | GJA1 | 0.72 |
| 211596_s_at | leucine-rich repeats and immunoglobulin-like domains 1 /// leucine-rich repeats and immunoglobulin-like domains 1 | LRIG1 | 0.72 |
| 219126_at | PHD finger protein 10 | PHF10 | 0.72 |
| 212526_at | spastic paraplegia 20, spartin (Troyer syndrome) | SPG20 | 0.72 |
| 202796_at | synaptopodin | SYNPO | 0.72 |
| 212976_at | T-cell activation leucine repeat-rich protein | TA-LRRP | 0.72 |
| 203527_s_at | adenomatosis polyposis coli | APC | 0.73 |
| 215460_x_at | bromodomain containing 1 | BRD1 | 0.73 |
| 214198_s_at | DiGeorge syndrome critical region gene 2 | DGCR2 | 0.73 |
| 214022_s_at | interferon induced transmembrane protein 1 (9-27) | IFITM1 | 0.73 |
| 203354_at | pleckstrin and Sec7 domain containing 3 | PSD3 | 0.73 |
| 200971_s_at | stress-associated endoplasmic reticulum protein 1 | SERP1 | 0.73 |
| 203583_at | unc-50 homolog (*C. elegans*) | UNC50 | 0.73 |
| 217975_at | WW domain binding protein 5 | WBP5 | 0.73 |
| 207606_s_at | Rho GTPase activating protein 12 | ARHGAP12 | 0.74 |
| 203502_at | 2,3-bisphosphoglycerate mutase /// 2,3-bisphosphoglycerate mutase | BPGM | 0.74 |
| 214214_s_at | complement component 1, q subcomponent binding protein | C1QBP | 0.74 |
| 218930_s_at | hypothetical protein FLJ11273 | FLJ11273 | 0.74 |
| 214414_x_at | hemoglobin, alpha 2 /// hemoglobin, alpha 2 | HBA2 | 0.74 |
| 208965_s_at | interferon, gamma-inducible protein 16 | IFI16 | 0.74 |
| 32069_at | Nedd4 binding protein 1 | N4BP1 | 0.74 |
| 203478_at | NADH dehydrogenase (ubiquinone) 1, subcomplex unknown, 1, 6 kDa | NDUFC1 | 0.74 |
| 208638_at | protein disulfide isomerase-associated 6 | PDIA6 | 0.74 |
| 209025_s_at | synaptotagmin binding, cytoplasmic RNA interacting protein | SYNCRIP | 0.74 |
| 211699_x_at | hemoglobin, alpha 1 /// hemoglobin, alpha 1 /// hemoglobin, alpha 2 /// hemoglobin, alpha 2 | HBA1 | 0.75 |
| 207480_s_at | Meis1, myeloid ecotropic viral integration site 1 homolog 2 (mouse) | MEIS2 | 0.75 |
| 204491_at | Phosphodiesterase 4D, cAMP-specific (phosphodiesterase E3 dunce homolog, *Drosophila*) | PDE4D | 0.75 |
| 219196_at | secretogranin III | SCG3 | 0.75 |
| 202272_s_at | F-box protein 28 | FBXO28 | 0.76 |
| 204018_x_at | hemoglobin, alpha 1 /// hemoglobin, alpha 1 /// hemoglobin, alpha 2 /// hemoglobin, alpha 2 | HBA1 | 0.76 |
| 218352_at | regulator of chromosome condensation (RCC1) and BTB (POZ) domain containing protein 1 | RCBTB1 | 0.76 |
| 215452_x_at | SMT3 suppressor of mif two 3 homolog 4 (yeast) | SUMO4 | 0.76 |
| 205139_s_at | uronyl-2-sulfotransferase | UST | 0.76 |
| 202850_at | ATP-binding cassette, sub-family D (ALD), member 3 | ABCD3 | 0.77 |
| 203540_at | glial fibrillary acidic protein | GFAP | 0.77 |
| 218558_s_at | mitochondrial ribosomal protein L39 | MRPL39 | 0.77 |
| 208731_at | RAB2, member RAS oncogene family | RAB2 | 0.77 |
| 221493_at | TSPY-like 1 | TSPYL1 | 0.77 |
| 212074_at | unc-84 homolog A (*C. elegans*) | UNC84A | 0.77 |
| 212200_at | ankyrin repeat and LEM domain containing 2 | ANKLE2 | 0.78 |
| 202221_s_at | E1A binding protein p300 | EP300 | 0.78 |
| 209291_at | inhibitor of DNA binding 4, dominant negative helix-loop-helix protein | ID4 | 0.78 |
| 34031_i_at | KRIT1, ankyrin repeat containing | KRIT1 | 0.78 |
| 207121_s_at | mitogen-activated protein kinase 6 | MAPK6 | 0.78 |
| 203910_at | PTPL1-associated RhoGAP 1 | PARG1 | 0.78 |
| 205361_s_at | prefoldin 4 | PFDN4 | 0.78 |
| 214435_x_at | v-ral simian leukemia viral oncogene homolog A (ras related) | RALA | 0.78 |
| 202277_at | serine palmitoyltransferase, long chain base subunit 1 | SPTLC1 | 0.78 |
| 200887_s_at | signal transducer and activator of transcription 1, 91 kDa | STAT1 | 0.78 |
| 202573_at | casein kinase 1, gamma 2 | CSNK1G2 | 0.79 |
| 201921_at | guanine nucleotide binding protein (G protein), gamma 10 | GNG10 | 0.79 |
| 218239_s_at | GTP binding protein 4 | GTPBP4 | 0.79 |
| 209458_x_at | hemoglobin, alpha 1 /// hemoglobin, alpha 1 /// hemoglobin, alpha 2 /// hemoglobin, alpha 2 | HBA1 | 0.79 |
| 205051_s_at | v-kit Hardy-Zuckerman 4 feline sarcoma viral oncogene homolog | KIT | 0.79 |
| 208102_s_at | pleckstrin and Sec7 domain containing | PSD | 0.79 |
| 211733_x_at | sterol carrier protein 2 /// sterol carrier protein 2 | SCP2 | 0.79 |
| 208389_s_at | solute carrier family 1 (glial high affinity glutamate transporter), member 2 | SLC1A2 | 0.79 |
| 202690_s_at | small nuclear ribonucleoprotein D1 polypeptide 16 kDa | SNRPD1 | 0.79 |
| 201448_at | TIA1 cytotoxic granule-associated RNA binding protein | TIA1 | 0.79 |
| 218617_at | tRNA isopentenyltransferase 1 | TRIT1 | 0.79 |
| 218096_at | 1-acylglycerol-3-phosphate O-acyltransferase 5 (lysophosphatidic acid acyltransferase, epsilon) | AGPAT5 | 0.80 |
| 221596_s_at | chromosome 7 open reading frame 64 | C7orf64 | 0.80 |

TABLE 1-continued

Final list of 383 selected genes

| Affymetrix ID | Gene Title | Gene Symbol | FC DEP |
|---|---|---|---|
| 221804_s_at | family with sequence similarity 45, member B /// family with sequence similarity 45, member A | FAM45B | 0.80 |
| 214429_at | myotubularin related protein 6 | MTMR6 | 0.80 |
| 217764_s_at | RAB31, member RAS oncogene family | RAB31 | 0.80 |
| 212042_x_at | ribosomal protein L7 | RPL7 | 0.80 |
| 202800_at | solute carrier family 1 (glial high affinity glutamate transporter), member 3 | SLC1A3 | 0.80 |
| 212725_s_at | hypothetical protein TI-227H | TI-227H | 0.80 |
| 208374_s_at | capping protein (actin filament) muscle Z-line, alpha 1 | CAPZA1 | 0.81 |
| 202469_s_at | cleavage and polyadenylation specific factor 6, 68 kDa | CPSF6 | 0.81 |
| 209630_s_at | F-box and WD-40 domain protein 2 | FBXW2 | 0.81 |
| 212334_at | glucosamine (N-acetyl)-6-sulfatase (Sanfilippo disease IIID) | GNS | 0.81 |
| 218641_at | chromosome 11 open reading frame 95 | C11orf95 | 0.81 |
| 212120_at | Ras homolog gene family, member Q | RHOQ | 0.81 |
| 216274_s_at | SEC11-like 1 (*S. cerevisiae*) | SEC11L1 | 0.81 |
| 218878_s_at | sirtuin (silent mating type information regulation 2 homolog) 1 (*S. cerevisiae*) | SIRT1 | 0.81 |
| 212774_at | zinc finger protein 238 | ZNF238 | 0.81 |
| 201334_s_at | Rho guanine nucleotide exchange factor (GEF) 12 | ARHGEF12 | 0.82 |
| 201117_s_at | carboxypeptidase E | CPE | 0.82 |
| 218443_s_at | DAZ associated protein 1 | DAZAP1 | 0.82 |
| 207768_at | early growth response 4 | EGR4 | 0.82 |
| 217828_at | modulator of estrogen induced transcription | FLJ13213 | 0.82 |
| 221255_s_at | transmembrane protein 93 | TMEM93 | 0.82 |
| 201468_s_at | NAD(P)H dehydrogenase, quinone 1 | NQO1 | 0.82 |
| 221795_at | neurotrophic tyrosine kinase, receptor, type 2 | NTRK2 | 0.82 |
| 208205_at | protocadherin alpha 9 | PCDHA9 | 0.82 |
| 203966_s_at | protein phosphatase 1A (formerly 2C), magnesium-dependent, alpha isoform /// protein phosphatase 1A (formerly 2C), magnesium-dependent, alpha isoform | PPM1A | 0.82 |
| 47069_at | proline rich protein 5 | PRR5 | 0.82 |
| 212468_at | sperm associated antigen 9 | SPAG9 | 0.82 |
| 218466_at | TBC1 domain family, member 17 | TBC1D17 | 0.82 |
| 218090_s_at | WD repeat domain 11 | WDR11 | 0.82 |
| 218490_s_at | zinc finger protein 302 | ZNF302 | 0.82 |
| 209028_s_at | abI-interactor 1 | ABI1 | 0.83 |
| 210068_s_at | aquaporin 4 | AQP4 | 0.83 |
| 221482_s_at | cyclic AMP phosphoprotein, 19 kD | ARPP-19 | 0.83 |
| 53720_at | chromosome 19 open reading frame 66 | C19orf66 | 0.83 |
| 211745_x_at | hemoglobin, alpha 1 /// hemoglobin, alpha 1 /// hemoglobin, alpha 2 /// hemoglobin, alpha 2 | HBA1 | 0.83 |
| 200989_at | hypoxia-inducible factor 1, alpha subunit (basic helix-loop-helix transcription factor) | HIF1A | 0.83 |
| 221847_at | Transcribed locus, strongly similar to XP_001721967.1 PREDICTED: similar to mCG115122 [*Homo sapiens*] | Hs.521817 | 0.83 |
| 221045_s_at | period homolog 3 (*Drosophila*) | PER3 | 0.83 |
| 202318_s_at | SUMO1/sentrin specific protease 6 | SENP6 | 0.83 |
| 213881_x_at | SMT3 suppressor of mif two 3 homolog 2 (yeast) | SUMO2 | 0.83 |
| 220990_s_at | likely ortholog of rat vacuole membrane protein 1 /// likely ortholog of rat vacuole membrane protein 1 | VMP1 | 0.83 |
| 203608_at | aldehyde dehydrogenase 5 family, member A1 (succinate-semialdehyde dehydrogenase) | ALDH5A1 | 0.84 |
| 211502_s_at | PFTAIRE protein kinase 1 | PFTK1 | 0.84 |
| 219485_s_at | proteasome (prosome, macropain) 26S subunit, non-ATPase, 10 | PSMD10 | 0.84 |
| 212458_at | sprouty-related, EVH1 domain containing 2 | SPRED2 | 0.84 |
| 217853_at | tensin-like SH2 domain containing 1 | TENS1 | 0.84 |
| 204847_at | zinc finger and BTB domain containing 11 | ZBTB11 | 0.84 |
| 213220_at | BBSome interacting protein 1 | BBIP1 | 0.85 |
| 213294_at | eukaryotic translation initiation factor 2-alpha kinase 2 | EIF2AK2 | 0.85 |
| 220188_at | junctophilin 3 | JPH3 | 0.85 |
| 222158_s_at | CGI-146 protein | PNAS-4 | 0.85 |
| 200845_s_at | peroxiredoxin 6 | PRDX6 | 0.85 |
| 200608_s_at | RAD21 homolog (*S. pombe*) | RAD21 | 0.85 |
| 212749_s_at | ring finger and CHY zinc finger domain containing 1 | RCHY1 | 0.85 |
| 203908_at | solute carrier family 4, sodium bicarbonate cotransporter, member 4 | SLC4A4 | 0.85 |
| 201273_s_at | signal recognition particle 9 kDa | SRP9 | 0.85 |
| 212388_at | ubiquitin specific protease 24 | USP24 | 0.85 |
| 203420_at | family with sequence similarity 8, member A1 | FAM8A1 | 0.86 |
| 210111_s_at | kelch domain containing 10 | KLHDC10 | 0.86 |
| 219156_at | synaptojanin 2 binding protein | SYNJ2BP | 0.86 |
| 219935_at | a disintegrin-like and metalloprotease (reprolysin type) with thrombospondin type 1 motif, 5 (aggrecanase-2) | ADAMTS5 | 0.87 |
| 202834_at | angiotensinogen (serine (or cysteine) proteinase inhibitor, clade A (alpha-1 antiproteinase, antitrypsin), member 8) | AGT | 0.87 |
| 203295_s_at | ATPase, Na+/K+ transporting, alpha 2 (+) polypeptide | ATP1A2 | 0.87 |
| 214334_x_at | DAZ associated protein 2 /// similar to DAZ-associated protein 2 (Deleted in azoospermia-associated protein 2) | DAZAP2 | 0.87 |

TABLE 1-continued

Final list of 383 selected genes

| Affymetrix ID | Gene Title | Gene Symbol | FC DEP |
|---|---|---|---|
| 217202_s_at | glutamate-ammonia ligase (glutamine synthase) | GLUL | 0.87 |
| 200921_s_at | B-cell translocation gene 1, anti-proliferative | BTG1 | 0.88 |
| 217768_at | chromosome 14 open reading frame 166 | C14orf166 | 0.88 |
| 211424_x_at | methyltransferase like 7A | METTL7A | 0.88 |
| 220924_s_at | solute carrier family 38, member 2 | SLC38A2 | 0.88 |
| 205152_at | solute carrier family 6 (neurotransmitter transporter, GABA), member 1 | SLC6A1 | 0.88 |
| 210512_s_at | vascular endothelial growth factor | VEGF | 0.88 |
| 214934_at | ATPase, Class II, type 9B | ATP9B | 0.89 |
| 208853_s_at | calnexin | CANX | 0.89 |
| 209470_s_at | glycoprotein M6A | GPM6A | 0.89 |
| 207700_s_at | nuclear receptor coactivator 3 | NCOA3 | 0.89 |
| 209355_s_at | phosphatidic acid phosphatase type 2B | PPAP2B | 0.89 |
| 212230_at | phosphatidic acid phosphatase type 2B | PPAP2B | 0.89 |
| 218284_at | SMAD, mothers against DPP homolog 3 (*Drosophila*) | SMAD3 | 0.89 |
| 212625_at | syntaxin 10 | STX10 | 0.89 |
| 201857_at | zinc finger RNA binding protein | ZFR | 0.89 |
| 219300_s_at | contactin associated protein-like 2 | CNTNAP2 | 0.90 |
| 206401_s_at | microtubule-associated protein tau | MAPT | 0.90 |
| 218259_at | MKL/myocardin-like 2 | MKL2 | 0.90 |
| 203961_at | nebulette | NEBL | 0.90 |
| 203177_x_at | transcription factor A, mitochondrial | TFAM | 0.90 |
| 209656_s_at | transmembrane protein 47 | TMEM47 | 0.90 |
| 218185_s_at | armadillo repeat containing 1 | ARMC1 | 0.91 |
| 206849_at | gamma-aminobutyric acid (GABA) A receptor, gamma 2 | GABRG2 | 0.91 |
| 217739_s_at | pre-B-cell colony enhancing factor 1 | PBEF1 | 0.91 |
| 201594_s_at | protein phosphatase 4, regulatory subunit 1 | PPP4R1 | 0.91 |
| 202126_at | PRP4 pre-mRNA processing factor 4 homolog B (yeast) | PRPF4B | 0.91 |
| 220949_s_at | chromosome 7 open reading frame 49 | C7orf49 | 0.92 |
| 210015_s_at | microtubule-associated protein 2 | MAP2 | 0.92 |
| 200969_at | stress-associated endoplasmic reticulum protein 1 | SERP1 | 0.92 |
| 212190_at | serine (or cysteine) proteinase inhibitor, clade E (nexin, plasminogen activator inhibitor type 1), member 2 | SERPINE2 | 0.92 |
| 213351_s_at | transmembrane and coiled-coil domains 1 | TMCC1 | 0.92 |
| 200972_at | tetraspanin 3 | TSPAN3 | 0.93 |
| 201021_s_at | destrin (actin depolymerizing factor) | DSTN | 0.94 |
| 209956_s_at | calcium/calmodulin-dependent protein kinase (CaM kinase) II beta | CAMK2B | 0.95 |
| 207010_at | gamma-aminobutyric acid (GABA) A receptor, beta 1 | GABRB1 | 0.96 |
| 214953_s_at | amyloid beta (A4) precursor protein (protease nexin-II, Alzheimer disease) | APP | 0.97 |
| 201445_at | calponin 3, acidic | CNN3 | 0.97 |
| 215145_s_at | contactin associated protein-like 2 | CNTNAP2 | 0.98 |
| 210906_x_at | aquaporin 4 | AQP4 | 0.99 |
| 202438_x_at | iduronate 2-sulfatase (Hunter syndrome) | IDS | 0.99 |
| 201427_s_at | selenoprotein P, plasma, 1 | SEPP1 | 0.99 |
| 210949_s_at | eukaryotic translation initiation factor 3, subunit 8, 110 kDa | EIF3S8 | 1.00 |
| 221236_s_at | stathmin-like 4 /// stathmin-like 4 | STMN4 | 1.00 |
| 217717_s_at | tyrosine 3-monooxygenase/tryptophan 5-monooxygenase activation protein, beta polypeptide | YWHAB | 1.00 |
| 213998_s_at | DEAD (Asp-Glu-Ala-Asp) box polypeptide 17 | DDX17 | 1.01 |
| 201537_s_at | dual specificity phosphatase 3 (vaccinia virus phosphatase VH1-related) | DUSP3 | 1.01 |
| 200648_s_at | glutamate-ammonia ligase (glutamine synthase) | GLUL | 1.01 |
| 205150_s_at | TLR4 interactor with leucine-rich repeats | TRIL | 1.01 |
| 200848_at | S-adenosylhomocysteine hydrolase-like 1 | AHCYL1 | 1.02 |
| 211547_s_at | platelet-activating factor acetylhydrolase, isoform Ib, alpha subunit 45 kDa | PAFAH1B1 | 1.03 |
| 204230_s_at | solute carrier family 17 (sodium-dependent inorganic phosphate cotransporter), member 7 | SLC17A7 | 1.03 |
| 201360_at | cystatin C (amyloid angiopathy and cerebral hemorrhage) | CST3 | 1.04 |
| 215363_x_at | folate hydrolase (prostate-specific membrane antigen) 1 | FOLH1 | 1.04 |
| 203603_s_at | zinc finger homeobox 1b | ZFHX1B | 1.04 |
| 45572_s_at | golgi associated, gamma adaptin ear containing, ARF binding protein 1 | GGA1 | 1.05 |
| 217741_s_at | zinc finger, A20 domain containing 2 | ZA20D2 | 1.05 |
| 208840_s_at | Ras-GTPase activating protein SH3 domain-binding protein 2 | G3BP2 | 1.06 |
| 200658_s_at | prohibitin | PHB | 1.07 |
| 208850_s_at | Thy-1 cell surface antigen /// Thy-1 co-transcribed | THY1 | 1.07 |
| 209372_x_at | tubulin, beta 2 /// tubulin, beta polypeptide paralog | TUBB2 | 1.07 |
| 207276_at | cerebellar degeneration-related protein 1, 34 kDa | CDR1 | 1.08 |
| 218532_s_at | family with sequence similarity 134, member B | FAM134B | 1.08 |
| 208687_x_at | heat shock 70 kDa protein 8 | HSPA8 | 1.08 |
| 201270_x_at | NudC domain containing 3 | NUDCD3 | 1.08 |
| 215773_x_at | poly (ADP-ribose) polymerase family, member 2 | PARP2 | 1.08 |
| 204218_at | chromosome 11 open reading frame 51 | C11orf51 | 1.10 |
| 205549_at | Purkinje cell protein 4 | PCP4 | 1.10 |
| 202004_x_at | succinate dehydrogenase complex, subunit C, integral membrane protein, 15 kDa | SDHC | 1.10 |

TABLE 1-continued

Final list of 383 selected genes

| Affymetrix ID | Gene Title | Gene Symbol | FC DEP |
|---|---|---|---|
| 211714_x_at | tubulin, beta polypeptide /// tubulin, beta polypeptide | TUBB | 1.10 |
| 207761_s_at | methyltransferase like 7A | METTL7A | 1.11 |
| 217871_s_at | macrophage migration inhibitory factor (glycosylation-inhibiting factor) | MIF | 1.11 |
| 210315_at | synapsin II | SYN2 | 1.11 |
| 203545_at | asparagine-linked glycosylation 8 homolog (yeast, alpha-1,3-glucosyltransferase) | ALG8 | 1.12 |
| 209569_x_at | DNA segment on chromosome 4 (unique) 234 expressed sequence | D4S234E | 1.12 |
| 43511_s_at | arrestin, beta 1 | ARRB1 | 1.13 |
| 207722_s_at | BTB (POZ) domain containing 2 | BTBD2 | 1.13 |
| 200824_at | glutathione S-transferase pi | GSTP1 | 1.13 |
| 201627_s_at | insulin induced gene 1 | INSIG1 | 1.13 |
| 202138_x_at | JTV1 gene | JTV1 | 1.13 |
| 218012_at | TSPY-like 2 | TSPYL2 | 1.13 |
| 213726_x_at | tubulin, beta, 2 | TUBB2 | 1.13 |
| 209517_s_at | ash2 (absent, small, or homeotic)-like (*Drosophila*) | ASH2L | 1.14 |
| 217950_at | nitric oxide synthase interacting protein | NOSIP | 1.14 |
| 210131_x_at | succinate dehydrogenase complex, subunit C, integral membrane protein, 15 kDa | SDHC | 1.14 |
| 212238_at | additional sex combs like 1 (*Drosophila*) | ASXL1 | 1.15 |
| 213052_at | Protein kinase, cAMP-dependent, regulatory, type II, alpha | PRKAR2A | 1.15 |
| 200802_s_at | seryl-tRNA synthetase | SARS | 1.15 |
| 203400_s_at | transferrin | TF | 1.15 |
| 208358_s_at | UDP glycosyltransferase 8 (UDP-galactose ceramide galactosyltransferase) | UGT8 | 1.15 |
| 214699_x_at | WIPI49-like protein 2 | WIPI-2 | 1.15 |
| 200720_s_at | ARP1 actin-related protein 1 homolog A, centractin alpha (yeast) | ACTR1A | 1.16 |
| 39835_at | SET binding factor 1 | SBF1 | 1.16 |
| 202118_s_at | copine III | CPNE3 | 1.17 |
| 216850_at | small nuclear ribonucleoprotein polypeptide N | SNRPN | 1.17 |
| 217799_x_at | ubiquitin-conjugating enzyme E2H (UBC8 homolog, yeast) | UBE2H | 1.17 |
| 205625_s_at | calbindin 1, 28 kDa | CALB1 | 1.18 |
| 200919_at | polyhomeotic-like 2 (*Drosophila*) | PHC2 | 1.18 |
| 212216_at | prolyl endopeptidase-like | PREPL | 1.18 |
| 209875_s_at | secreted phosphoprotein 1 (osteopontin, bone sialoprotein I, early T-lymphocyte activation 1) | SPP1 | 1.18 |
| 204260_at | chromogranin B (secretogranin 1) | CHGB | 1.19 |
| 218539_at | F-box protein 34 | FBXO34 | 1.19 |
| 202472_at | mannose phosphate isomerase | MPI | 1.19 |
| 220653_at | zinc finger, imprinted 2 | ZIM2 | 1.19 |
| 207593_at | ATP-binding cassette, sub-family G (WHITE), member 4 | ABCG4 | 1.20 |
| 218953_s_at | prenylcysteine oxidase 1 like | PCYOX1L | 1.20 |
| 210130_s_at | transmembrane 7 superfamily member 2 | TM7SF2 | 1.20 |
| 222046_at | arsenate resistance protein ARS2 | ARS2 | 1.21 |
| 220725_x_at | Dynein, axonemal, heavy polypeptide 3 | DNAH3 | 1.21 |
| 204466_s_at | synuclein, alpha (non A4 component of amyloid precursor) /// synuclein, alpha (non A4 component of amyloid precursor) | SNCA | 1.21 |
| 207594_s_at | synaptojanin 1 | SYNJ1 | 1.21 |
| 207991_x_at | acrosomal vesicle protein 1 | ACRV1 | 1.22 |
| 218958_at | chromosome 19 open reading frame 60 | C19orf60 | 1.22 |
| 200647_s_at | eukaryotic translation initiation factor 3, subunit 8, 110 kDa | EIF3S8 | 1.22 |
| 213629_x_at | metallothionein 1F (functional) | MT1F | 1.22 |
| 200003_s_at | ribosomal protein L28 /// ribosomal protein L28 | RPL28 | 1.22 |
| 201870_at | translocase of outer mitochondrial membrane 34 | TOMM34 | 1.22 |
| 202589_at | thymidylate synthetase | TYMS | 1.22 |
| 221676_s_at | coronin, actin binding protein, 1C | CORO1C | 1.23 |
| 209581_at | HRAS-like suppressor 3 | HRASLS3 | 1.23 |
| 209467_s_at | MAP kinase interacting serine/threonine kinase 1 | MKNK1 | 1.23 |
| 200820_at | proteasome (prosome, macropain) 26S subunit, non-ATPase, 8 | PSMD8 | 1.23 |
| 201127_s_at | ATP citrate lyase | ACLY | 1.24 |
| 202154_x_at | tubulin, beta 3 | TUBB3 | 1.24 |
| 206966_s_at | Kruppel-like factor 12 | KLF12 | 1.25 |
| 217609_at | B7 gene | B7 | 1.26 |
| 201953_at | calcium and integrin binding 1 (calmyrin) | CIB1 | 1.26 |
| 217930_s_at | toll interacting protein | TOLLIP | 1.26 |
| 211538_s_at | heat shock 70 kDa protein 2 | HSPA2 | 1.28 |
| 219236_at | progestin and adipoQ receptor family member VI | PAQR6 | 1.28 |
| 205899_at | cyclin A1 | CCNA1 | 1.29 |
| 212878_s_at | kinesin 2 60/70 kDa | KNS2 | 1.29 |
| 220236_at | pyruvate dehydrogenase phosphatase regulatory subunit | PDPR | 1.29 |
| 204035_at | secretogranin II (chromogranin C) | SCG2 | 1.29 |
| 210858_x_at | ataxia telangiectasia mutated (includes complementation groups A, C and D) | ATM | 1.30 |
| 207401_at | prospero-related homeobox 1 | PROX1 | 1.30 |
| 203022_at | ribonuclease H2, large subunit | RNASEH2A | 1.30 |
| 206748_s_at | sperm associated antigen 9 | SPAG9 | 1.30 |
| 221196_x_at | chromosome X open reading frame 53 | CXorf53 | 1.31 |

TABLE 1-continued

Final list of 383 selected genes

| Affymetrix ID | Gene Title | Gene Symbol | FC DEP |
|---|---|---|---|
| 218488_at | eukaryotic translation initiation factor 2B, subunit 3 gamma, 58 kDa | EIF2B3 | 1.31 |
| 209392_at | ectonucleotide pyrophosphatase/phosphodiesterase 2 (autotaxin) | ENPP2 | 1.31 |
| 34868_at | Est1p-like protein B | EST1B | 1.31 |
| 207801_s_at | ring finger protein 10 | RNF10 | 1.31 |
| 212155_at | ring finger protein 187 | RNF187 | 1.31 |
| 206283_s_at | T-cell acute lymphocytic leukemia 1 | TAL1 | 1.31 |
| 203842_s_at | microtubule-associated protein, RP/EB family, member 3 | MAPRE3 | 1.32 |
| 204179_at | myoglobin | MB | 1.33 |
| 215771_x_at | ret proto-oncogene (multiple endocrine neoplasia and medullary thyroid carcinoma 1, Hirschsprung disease) | RET | 1.33 |
| 201785_at | ribonuclease, RNase A family, 1 (pancreatic) | RNASE1 | 1.34 |
| 214915_at | zinc finger protein 362 | ZNF362 | 1.34 |
| 212772_s_at | ATP-binding cassette, sub-family A (ABC1), member 2 | ABCA2 | 1.35 |
| 213300_at | ATG2 autophagy related 2 homolog A (S. cerevisiae) | ATG2A | 1.35 |
| 212394_at | KIAA0090 | KIAA0090 | 1.35 |
| 210136_at | Myelin basic protein | MBP | 1.35 |
| 209283_at | crystallin, alpha B | CRYAB | 1.36 |
| 207972_at | glycine receptor, alpha 1 (startle disease/hyperekplexia, stiff man syndrome) | GLRA1 | 1.36 |
| 217008_s_at | glutamate receptor, metabotropic 7 | GRM7 | 1.37 |
| 204550_x_at | glutathione S-transferase M1 | GSTM1 | 1.37 |
| 203436_at | ribonuclease P/MRP 30 kDa subunit | RPP30 | 1.37 |
| 201037_at | phosphofructokinase, platelet | PFKP | 1.38 |
| 219105_x_at | origin recognition complex, subunit 6 homolog-like (yeast) | ORC6L | 1.39 |
| 222153_at | myelin expression factor 2 | MYEF2 | 1.43 |
| 209771_x_at | CD24 antigen (small cell lung carcinoma cluster 4 antigen) | CD24 | 1.45 |
| 222073_at | collagen, type IV, alpha 3 (Goodpasture antigen) | COL4A3 | 1.45 |
| 215643_at | Sema domain, immunoglobulin domain (Ig), short basic domain, secreted, (semaphorin) 3D | SEMA3D | 1.45 |
| 214063_s_at | transferrin | TF | 1.45 |
| 218183_at | chromosome 16 open reading frame 5 | C16orf5 | 1.46 |
| 210679_x_at | — | — | 1.47 |
| 204073_s_at | chromosome 11 open reading frame 9 | C11orf9 | 1.48 |
| 204733_at | kallikrein 6 (neurosin, zyme) | KLK6 | 1.50 |
| 206106_at | mitogen-activated protein kinase 12 | MAPK12 | 1.51 |
| 204777_s_at | mal, T-cell differentiation protein | MAL | 1.52 |
| 208851_s_at | Thy-1 cell surface antigen /// Thy-1 co-transcribed | THY1 | 1.54 |
| 204719_at | ATP-binding cassette, sub-family A (ABC1), member 8 | ABCA8 | 1.55 |
| 266_s_at | CD24 antigen (small cell lung carcinoma cluster 4 antigen) | CD24 | 1.55 |
| 216617_s_at | myelin associated glycoprotein | MAG | 1.55 |
| 216379_x_at | CD24 antigen (small cell lung carcinoma cluster 4 antigen) | CD24 | 1.57 |
| 207713_s_at | chromosome 20 open reading frame 18 | C20orf18 | 1.58 |
| 202068_s_at | low density lipoprotein receptor (familial hypercholesterolemia) | LDLR | 1.60 |
| 215986_at | Homo sapiens cDNA FLJ12058 fis, clone HEMBB1002092. | AK022120 | 1.61 |
| 205061_s_at | exosome component 9 | EXOSC9 | 1.62 |
| 207445_s_at | chemokine (C-C motif) receptor 9 | CCR9 | 1.63 |
| 212672_at | Ataxia telangiectasia mutated (includes complementation groups A, C and D) | ATM | 1.66 |
| 215531_s_at | gamma-aminobutyric acid (GABA) A receptor, alpha 5 | GABRA5 | 1.79 |
| 221031_s_at | apolipoprotein L domain containing 1 | APOLD1 | 2.01 |
| 220873_at | RALBP1 associated Eps domain containing 2 | REPS2 | 2.04 |

TABLE 2

Selected genes for qRT-PCR

| Gene Name | Gene Symbol |
|---|---|
| adrenergic, alpha-1A-, receptor | ADRA1A |
| adrenergic, alpha-1B-, receptor | ADRA1B |
| adrenergic, alpha-1D-, receptor | ADRA1D |
| adrenergic, alpha-2A-, receptor | ADRA2A |
| amyloid beta (A4) precursor protein (protease nexin-II, Alzheimer disease) | APP |
| cyclic AMP phosphoprotein, 19 kD (Interim) | ARPP-19 |
| axotrophin | AXOT |
| brain cell membrane protein 1 (Interim) | BCMP1 |
| brain-derived neurotrophic factor | BDNF |
| chromosome 22 open reading frame 4 | C22orf4 |
| calcium binding protein 1 (calbrain) | CABP1 |
| calcium/calmodulin-dependent protein kinase (CaM kinase) II beta | CAMK2B |
| calnexin | CANX |
| chemokine (C-C motif) receptor 9 | CCR9 |
| cAMP-regulated guanine nucleotide exchange factor II (Interim) | CGEF2 |

TABLE 2-continued

Selected genes for qRT-PCR

| Gene Name | Gene Symbol |
|---|---|
| chromogranin B (secretogranin 1) | CHGB |
| calcium and integrin binding 1 (calmyrin) | CIB1 |
| CREB binding protein (Rubinstein-Taybi syndrome) | CREBBP |
| G protein-binding protein CRFG (Interim) | CRFG |
| corticotropin releasing hormone | CRH |
| corticotropin releasing hormone receptor 1 | CRHR1 |
| corticotropin releasing hormone receptor 2 | CRHR2 |
| DNA segment on chromosome 4 (unique) 234 expressed sequence | D4S234E |
| dual-specificity tyrosine-(Y)-phosphorylation regulated kinase 2 | DYRK2 |
| ectonucleotide pyrophosphatase/phosphodiesterase 2 (autotaxin) | ENPP2 |
| erbb2 interacting protein | ERBB2IP |
| gamma-aminobutyric acid (GABA) A receptor, alpha 1 | GABRA1 |
| gamma-aminobutyric acid (GABA) A receptor, beta 1 | GABRB1 |
| gamma-aminobutyric acid (GABA) A receptor, gamma 2 | GABRG2 |
| glial fibrillary acidic protein | GFAP |
| glycine receptor, alpha 1 (startle disease/hyperekplexia, stiff man syndrome) | GLRA1 |
| guanine nucleotide binding protein 10 | GNG10 |
| glutamate receptor, metabotropic 7 | GRM7 |
| heat shock 70 kDa protein 2 | HSPA2 |
| 5-hydroxytryptamine (serotonin) receptor 1A | HTR1A |
| 5-hydroxytryptamine (serotonin) receptor 1B | HTR1B |
| 5-hydroxytryptamine (serotonin) receptor 1E | HTR1E |
| 5-hydroxytryptamine (serotonin) receptor 2A | HTR2A |
| 5-hydroxytryptamine (serotonin) receptor 2C | HTR2C |
| integrin beta 3 binding protein (beta3-endonexin) | ITGB3BP |
| inositol 1,4,5-trisphosphate 3-kinase B | ITPKB |
| intersectin 1 (SH3 domain protein) | ITSN1 |
| potassium voltage-gated channel, Shal-related subfamily, member 2 | KCND2 |
| potassium inwardly-rectifying channel, subfamily J, member 16 | KCNJ16 |
| putative L-type neutral amino acid transporter (Interim) | KIAA0436 |
| synaptopodin (Interim) | KIAA1029 |
| low density lipoprotein receptor (familial hypercholesterolemia) | LDLR |
| myelin associated glycoprotein | MAG |
| microtubule-associated protein 2 | MAP2 |
| microtubule-associated protein, RP/EB family, member 3 | MAPRE3 |
| microtubule-associated protein tau | MAPT |
| MAP kinase-interacting serine/threonine kinase 1 | MKNK1 |
| myelin-associated oligodendrocyte basic protein | MOBP |
| NCK-associated protein 1 | NCKAP1 |
| neurotrophic tyrosine kinase, receptor, type 1 | NTRK1 |
| neurotrophic tyrosine kinase, receptor, type 3 | NTRK3 |
| opioid receptor, mu 1 | OPRM1 |
| polyhomeotic-like 2 (*Drosophila*) | PHC2 |
| phosphatidic acid phosphatase type 2B | PPAP2B |
| protein phosphatase 1A (formerly 2C), magnesium-dependent, alpha isoform | PPM1A |
| protein phosphatase 2, regulatory subunit B (B56), beta isoform | PPP2R5B |
| protein phosphatase 3 (formerly 2B), catalytic subunit, alpha isoform (calcineurin A alpha) | PPP3CA |
| protein phosphatase 4, regulatory subunit 1 | PPP4R1 |
| protein kinase, cAMP-dependent, regulatory, type I, alpha (tissue specific extinguisher 1) | PRKAR1A |
| pleckstrin and Sec7 domain protein | PSD |
| pleiotrophin (heparin binding growth factor 8, neurite growth-promoting factor 1) | PTN |
| protein tyrosine phosphatase, receptor type, M | PTPRM |
| RAB22A, member RAS oncogene family | RAB22A |
| regulator of G-protein signalling 4 | RGS4 |
| secretogranin II (chromogranin C) | SCG2 |
| sodium channel, voltage-gated, type I, alpha | SCN1A |
| solute carrier family 1 (glial high affinity glutamate transporter), member 2 | SLC1A2 |
| solute carrier family 1 (glial high affinity glutamate transporter), member 3 | SLC1A3 |
| solute carrier family 38, member 2 | SLC38A2 |
| SM-11044 binding protein (Interim) | SMBP |
| somatostatin | SST |
| syntaxin 10 | STX10 |
| synapsin II | SYN2 |
| synaptojanin 1 | SYNJ1 |
| synaptojanin 2 binding protein | SYNJ2BP |
| tachykinin, precursor 1 (substance K, substance P, neurokinin 1, neurokinin 2, neuromedin L, neurokinin alpha, neuropeptide K, neuropeptide gamma) | TAC1 |
| TANK-binding kinase 1 | TBK1 |
| transferrin | TF |

TABLE 3

Genes differentially expressed between cases and controls

| Nombre | DEP vs Control | |
| --- | --- | --- |
| | p-value | FC |
| Amyloid beta (A4) precursor protein | 0.0002 | 0.82 |
| Cyclic AMP phosphoprotein, 19 kD | 0.2461 | 0.76 |
| Brain cell membrane protein 1 | 0.0189 | 0.82 |
| Chromosome 22 ORF 4 | 0.0103 | 0.88 |
| Calcium binding protein 1 (calbrain) | 0.0003 | 0.82 |
| Calcium/calmodulin-dependent protein kinase (CaM kinase) II beta | 0.1101 | 0.92 |
| Calnexin | 0.0001 | 0.85 |
| cAMP-regulated guanine nucleotide exchange factor II | 0.0055 | 0.80 |
| Calcium and integrin biniding 1 (Calmyrin) | 0.0000 | 0.76 |
| G protein-binding protein | 0.0002 | 0.86 |
| DNA segment on chromosome 4 (unique) 234 expressed sequence (neuron-specific protein) | 0.0411 | 1.12 |
| Erbb2 interacting protein | 0.1558 | 0.87 |
| Guanine nucleotide binding protein 10 | 0.0127 | 0.65 |
| Integrin beta 3 binding protein | 0.3006 | 0.86 |
| Inositol 1,4,5-trisphosphate 3-kinase B | 0.0247 | 0.81 |
| Intersectin 1 | 0.0125 | 0.91 |
| Potassium voltage-gated channel, Shal-related subfamily, member 2 | 0.1109 | 0.92 |
| Potassium inwardly-rectifying channel, subfamily J, member 16 | 0.0248 | 0.74 |
| Synaptopodin | 0.0104 | 0.85 |
| Low density lipoprotein receptor | 0.0593 | 1.22 |
| Microtubule-associated protein 2 | 0.0003 | 0.79 |
| Microtubule-associated protein tau | 0.0021 | 0.86 |
| MAP kinase-interacting serine/threonine kinase 1 | 0.0459 | 0.88 |
| NCK-associated protein 1 | 0.0000 | 0.75 |
| Polyhomeotic-like 2 (*Drosophila*) | 0.0055 | 0.87 |
| Phosphatidic acid phosphatase type 2B | 0.0232 | 0.82 |
| Protein phosphatase 1A, magnesium-dependent, alpha isoform | 0.1425 | 0.93 |
| Protein phosphatase 2, regulatory subunit B (B56), beta isoform | 0.0059 | 0.87 |
| Protein phosphatase 4, regulatory subunit 1 | 0.0147 | 0.86 |
| Protein kinase, cAMP-dependent, regulatory, type I, alpha (tissue specific extinguisher 1) | 0.0026 | 0.91 |
| Pleckstrin and Sec7 domain protein | 0.0783 | 0.88 |
| Pleiotrophin | 0.0093 | 0.77 |
| Protein tyrosine phosphatase, receptor type, M | 0.0009 | 0.84 |
| RAB22A, member RAS oncogene family | 0.7950 | 0.98 |
| Solute carrier family 1 (glial high affinity glutamate transporter), member 3 | 0.0091 | 0.76 |
| Sintaxin 10 | 0.0028 | 0.84 |
| Synapsin II | 0.1656 | 0.92 |
| Tachykinin, precursor 1 | 0.0297 | 0.83 |
| Tachykinin, precursor 1 | 0.0617 | 0.82 |
| Adrenergic alpha1A receptor | 0.0206 | 0.84 |
| Adrenergic alpha1B receptor | 0.0002 | 0.73 |
| Adrenergic alpha2A receptor | 0.5100 | 0.93 |
| Brain-derived neurotrophic factor | 0.2077 | 0.83 |
| Corticotropin releasing hormone | 0.3753 | 0.87 |
| Corticotropin releasing hormone receptor 1 | 0.1483 | 0.83 |
| Corticotropin releasing hormone receptor 2 | 0.7045 | 1.04 |
| Serotonin receptor 1A | 0.0005 | 0.79 |
| Serotonin receptor 1B | 0.1175 | 0.92 |
| Serotonin receptor 1E | 0.8936 | 1.01 |
| Serotonin receptor 2A | 0.2935 | 0.92 |
| Serotonin receptor 2C | 0.6676 | 1.10 |
| Tyrosine kinase receptor type 1 | 0.5002 | 0.89 |
| Tyrosine kinase receptor type 3 | 0.0864 | 0.90 |
| Opioid receptor, mu 1 | 0.9309 | 1.01 |

TABLE 4

Neuron-specific promoters: sequence information
NCBI Build number is as shown in the Table.

| NCBI Gene ID | Symbol | Description | RNA Refseq | Protein Refseq | Genomic Refseq (Including introns and exons) | Promoter Genomic Refseq (5' up-stream 10 kb) | Promoter Genomic Refseq (5' up-stream 100 kb) |
|---|---|---|---|---|---|---|---|
| mouse 13166 | DBH | dopamine beta hydroxylase | NM_138942.3 | NP_620392.2 | NC_000068.7 (27165508-27183204) (NCBI build 38.1) | (This gene is on + strand) (27155508-27165508) | (This gene is on + strand) (27065508-27165508) |
| human 1621 | DBH | dopamine beta-hydroxylase (dopamine beta-monooxygenase) | NM_000787.3 | NP_000778.3 | NC_000009.11 (136501485-136524466) NCBI build 37.3 | (This gene is on + strand) (136491485-136501485) | (This gene is on + strand) (136401485-136501485) |
| mouse 13807 | Eno2 | enolase 2, gamma neuronal | NM_013509.2 | NP_038537.1 | NC_000072.6 (124760055-124769509) NCBI build 38.1 | (This gene is on − strand) (124779509-124769509) | (This gene is on − strand) (124869509-124769509) |
| human 2026 | ENO2 | enolase 2 (gamma, neuronal) | NM_001975.2 | NP_001966.1 | NC_000012.11 (7023614-7032859) NCBI Build 37.3 | (This gene is on + strand) (7013614-7023614) | (This gene is on + strand) (6923614-7023614) |
| mouse 109594 | Lmo1 | LIM domain only 1 | NM_057173.2 | NP_476614.1 | NC_000073.6 (109138572-109170308) NCBI build 38.1 | (This gene is on − strand) (109170308-109180308) | (This gene is on − strand) (109170308-109270308) |
| human 4004 | LMO1 | LIM domain only 1 (rhombotin 1) | NM_002315.1 | NP_002306.1 | NC_000011.9 (8245857-8285406) NCBI Build 37.3 | (This gene is on − strand) (8285406-8295405) | (This gene is on − strand) (8285406-8385405) |
| mouse 18039 | Nefl | neurofilament, light polypeptide | NM_010910.1 | NP_035040.1 | NC_000080.6 (68083884-68087745) NCBI 38.1 | (This gene is on + strand) (68083884-68073884) | (This gene is on + strand) (68083884-67983884) |
| human 4747 | NEFL | neurofilament, light polypeptide | NM_006158.3 | NP_006149.2 | NC_000008.10 (24808468-24814131) NCBI 37.3 | (This gene is on − strand) (24814131-24824130) | (This gene is on − strand) (24814131-24914130) |

TABLE 4-continued

Neuron-specific promoters: sequence information NCBI Build number is as shown in the Table.

| NCBI Gene ID | Symbol | Description | RNA Refseq | Protein Refseq | Genomic Refseq (Including introns and exons) | Promoter Genomic Refseq (5' up-stream 10 kb) | Promoter Genomic Refseq (5' up-stream 100 kb) |
|---|---|---|---|---|---|---|---|
| mouse 18655 | Pgk1 | phosphoglycerate kinase 1 | NM_008828.2 | NP_032854.2 | NC_000086.7(106187124-106203699) NCBI 38.1 | (This gene is on + strand) (106187124-106177124) | (This gene is on + strand) (106187124-106087124) |
| human 5230 | PGK1 | phosphoglycerate kinase 1 | NM_000291.3 | NP_000282.1 | NC_000023.10 (77359665-77382323) NCBI 37.2 | (This gene is on + strand) (77349665-77359664) | (This gene is on + strand) (77259665-77359664) |
| mouse 20964 | Syn1 | synapsin I | NM_013680.4 | NP_038708.3 | NC_000086.7 (20860511-20920918) NCBI build 38.1 | (This gene is on − strand) (20930918-20920918) | (This gene is on − strand) (20020918-20920918) |
| mouse 20964 | Syn1 | synapsin I | NM_001110780.1 | NP_001104250.1 | NC_000086.7 (20860511-20920918) NCBI build 38.1 | (This gene is on − strand) (20930918-20920918) | (This gene is on − strand) (20020918-20920918) |
| human 6853 | SYN1 | synapsin I | NM_133499.2 | NP_598006.1 | NC_000023.10 (47431299-47479255) NCBI build 37.3 | (This gene is on − strand) (47479256-47489255) | (This gene is on − strand) (47479256-47579255) |
| human 6853 | SYN1 | synapsin I | NM_006950.3 | NP_008881.2 | NC_000023.10 (47431299-47479255) NCBI build 37.3 | (This gene is on − strand) (47479256-47489255) | (This gene is on − strand) (47479256-47579255) |
| mouse 21838 | Thy1 | thymus cell antigen 1, theta | NM_009382.3 | NP_033408.1 | NC_000075.6 (44043384-44048579) NCBI Build 38.1 | (This gene is on + strand) (44033384-44043384) | (This gene is on + strand) (43943384-44043384) |
| human 7070 | THY1 | Thy-1 cell surface antigen | NM_006288.3 | NP_006279.2 | NC_000011.9 (119288654-119294245) NCBI Build 37.3 | (This gene is on − strand) (119294246-119304245) | (This gene is on − strand) (119294246-119394245) |

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, including patent documents, disclosed herein are incorporated by reference in their entirety for all purposes, particularly for the disclosure referenced herein.

REFERENCE LIST

Belmaker R H, Agam G (2008) Major depressive disorder. N Engl J Med 358:55-68.

Calvet L, Geoerger B, Regairaz M, Opolon P, Machet L, Morizet J, Joseph J M, Elie N, Vassal G (2006) Pleiotrophin, a candidate gene for poor tumor vasculature and in vivo neuroblastoma sensitivity to irinotecan. Oncogene 25:3150-3159.

Chen H, Gordon M S, Campbell R A, Li M, Wang C S, Lee H J, Sanchez E, Manyak S J, Gui D, Shalitin D, Said J, Chang Y, Deuel T F, Baritaki S, Bonavida B, Berenson J R (2007) Pleiotrophin is highly expressed by myeloma cells and promotes myeloma tumor growth. Blood 110:287-295.

Christensen J G, Zou H Y, Arango M E, Li Q, Lee J H, McDonnell S R, Yamazaki S, Alton G R, Mroczkowski B, Los G (2007) Cytoreductive antitumor activity of PF-2341066, a novel inhibitor of anaplastic lymphoma kinase and c-Met, in experimental models of anaplastic large-cell lymphoma. Mol Cancer Ther 6:3314-3322.

DellaGioia N, Hannestad J (2010) A critical review of human endotoxin administration as an experimental paradigm of depression. Neurosci Biobehav Rev 34:130-143.

Deuel T F, Zhang N, Yeh H J, Silos-Santiago I, Wang Z Y (2002) Pleiotrophin: a cytokine with diverse functions and a novel signaling pathway. Arch Biochem Biophys 397:162-171.

Diamantopoulou Z, Bermek O, Polykratis A, Hamma-Kourbali Y, Delbe J, Courty J, Katsoris P (2010) A Pleiotrophin C-terminus peptide induces anti-cancer effects through RPTPbeta/zeta. Mol Cancer 9:224.

Dunn A J, Swiergiel A H, de B R (2005) Cytokines as mediators of depression: what can we learn from animal studies? Neurosci Biobehav Rev 29:891-909.

Furuta M, Shiraishi T, Okamoto H, Mineta T, Tabuchi K, Shiwa M (2004) Identification of pleiotrophin in conditioned medium secreted from neural stem cells by SELDI-TOF and SELDI-tandem mass spectrometry. Brain Res Dev Brain Res 152:189-197.

Hamma-Kourbali Y, Bernard-Pierrot I, Heroult M, Dalle S, Caruelle D, Milhiet P E, Fernig D G, Delbe J, Courty J (2008) Inhibition of the mitogenic, angiogenic and tumorigenic activities of pleiotrophin by a synthetic peptide corresponding to its C-thrombospondin repeat-I domain. J Cell Physiol 214:250-259.

Heinrich M C, Corless C L, Demetri G D, Blanke C D, von M M, Joensuu H, McGreevey L S, Chen C J, Van den Abbeele A D, Druker B J, Kiese B, Eisenberg B, Roberts P J, Singer S, Fletcher C D, Silberman S, Dimitrijevic S, Fletcher J A (2003) Kinase mutations and imatinib response in patients with metastatic gastrointestinal stromal tumor. J Clin Oncol 21:4342-4349.

Herry C, Garcia R (2002) Prefrontal cortex long-term potentiation, but not long-term depression, is associated with the maintenance of extinction of learned fear in mice. J Neurosci 22:577-583.

Holderbach R, Clark K, Moreau J L, Bischofberger J, Normann C (2007) Enhanced long-term synaptic depression in an animal model of depression. Biol Psychiatry 62:92-100.

Huang P, Ramphal J, Wei J, Liang C, Jallal B, McMahon G, Tang C (2003) Structure-based design and discovery of novel inhibitors of protein tyrosine phosphatases. Bioorg Med Chem 11:1835-1849.

Kadomatsu K, Muramatsu T (2004) Midkine and pleiotrophin in neural development and cancer. Cancer Lett 204:127-143.

Krishnan V, Nestler E J (2008) The molecular neurobiology of depression. Nature 455:894-902.

Krishnan V, Nestler E J (2010) Linking molecules to mood: new insight into the biology of depression. Am J Psychiatry 167:1305-1320.

Lee S, Jeong J, Kwak Y, Park S K (2010) Depression research: where are we now? Mol Brain 3:8.

Lorente G, Nelson A, Mueller S, Kuo J, Urfer R, Nikolich K, Foehr E D (2005) Functional comparison of long and short splice forms of RPTPbeta: implications for glioblastoma treatment. Neuro Oncol 7:154-163.

Mikelis C, Lamprou M, Koutsioumpa M, Koutsioubas A G, Spyranti Z, Zompra A A, Spiliopoulos N, Vradis A A, Katsoris P, Spyroulias G A, Cordopatis P, Courty J, Papadimitriou E (2011) A peptide corresponding to the C-terminal region of pleiotrophin inhibits angiogenesis in vivo and in vitro. J Cell Biochem 112:1532-1543.

Milner P G, Shah D, Veile R, Donis-Keller H, Kumar B V (1992) Cloning, nucleotide sequence, and chromosome localization of the human pleiotrophin gene. Biochemistry 31:12023-12028.

Pavlov I, Voikar V, Kaksonen M, Lauri S E, Hienola A, Taira T, Rauvala H (2002) Role of heparin-binding growth-associated molecule (HB-GAM) in hippocampal LTP and spatial learning revealed by studies on overexpressing and knockout mice. Mol Cell Neurosci 20:330-342.

Sabbatini P, Korenchuk S, Rowand J L, Groy A, Liu Q, Leperi D, Atkins C, Dumble M, Yang J, Anderson K, Kruger R G, Gontarek R R, Maksimchuk K R, Suravajjala S, Lapierre R R, Shotwell J B, Wilson J W, Chamberlain S D, Rabindran S K, Kumar R (2009) GSK1838705A inhibits the insulin-like growth factor-1 receptor and anaplastic lymphoma kinase and shows antitumor activity in experimental models of human cancers. Mol Cancer Ther 8:2811-2820.

Stewart C A, Reid I C (2002) Antidepressant mechanisms: functional and molecular correlates of excitatory amino acid neurotransmission. Mol Psychiatry 7 Suppl 1:S15-S22.

Sullivan P F, Neale M C, Kendler K S (2000) Genetic epidemiology of major depression: review and meta-analysis. Am J Psychiatry 157:1552-1562.

Tesseur I, Van D J, Spittaels K, Van Den Haute C, Moechars D, Van L F (2000) Expression of human apolipoprotein E4 in neurons causes hyperphosphorylation of protein tau in the brains of transgenic mice. Am J Pathol 156:951-964.

Vandesompele J, De P K, Pattyn F, Poppe B, Van R N, De P A, Speleman F (2002) Accurate normalization of real-time quantitative R T-PCR data by geometric averaging of multiple internal control genes. Genome Biol 3:RESEARCH0034.

Wong M L, Licinio J (2004) From monoamines to genomic targets: a paradigm shift for drug discovery in depression. Nat Rev Drug Discov 3:136-151.

The invention claimed is:

1. A transgenic mouse whose genome comprises a polynucleotide encoding a Pleiotrophin (PTN) polypeptide, which polynucleotide is operably linked to a neuron-specific promoter, wherein said transgenic mouse has greater than wild-type expression of the PTN polypeptide in at least one brain region, and wherein said neuron-specific promoter is selected from the group consisting of: a Thy1 gene promoter, Neuron specific enolase (NSE) gene promoter; Rhombotin I gene promoter; PGK gene promoter; Neurofilament Low (NF-L) gene promoter; dopamine beta-hydroxylase (DBH) gene promoter; and Synapsin-1 gene promoter, and wherein said transgenic mouse exhibits at least one behavior selected from the group consisting of reduced time spent in open arms of an elevated plus maze; reduced time in central area in an open-field test; reduced time in light in a light-dark box test; increased latency to feed in a Novelty Suppressed Feeding Test; increased immobility time in tail suspension test; and reduced sucrose intake in sucrose intake task.

2. The transgenic mouse according to claim 1, wherein said polynucleotide encodes:
   (i) a PTN polypeptide having an amino acid sequence having at least 80% amino acid sequence identity to the sequence of SEQ ID NO: 2;
   (ii) a PIN polypeptide having the amino acid sequence of SEQ ID NO: 2
   (iii) a PIN polypeptide having an amino acid sequence having at least 80% amino acid sequence identity to the sequence of SEQ ID NO: 4; or
   (iv) a PIN polypeptide having the amino acid sequence of SEQ ID NO: 4 and wherein said PIN polypeptide of any one of (i)-(iv) is capable of binding to specific receptors RPTPβ/ζ, ALK or Syndecan 3 polypeptide.

3. The transgenic mouse according to claim 1, wherein the neuron-specific promoter is a Thy1 gene promoter.

4. The transgenic mouse according to claim 3, wherein the Thy1 promoter comprises a polynucleotide having at least 80% nucleic acid sequence identity to the sequence of SEQ ID NO: 5.

5. The transgenic mouse according to claim 1, wherein said at least one brain region is selected from: cortex and hippocampus.

6. The transgenic mouse according to claim 1, having at least 100% greater expression of the PTN polypeptide in said at least one brain region, as measured by Western blot, immunofluorescence and/or qPCR of an PTN mRNA.

7. The transgenic mouse according to claim 1, wherein the mouse is a hybrid B6/SJL-F1J mouse.

8. An in vivo method for identifying an agent comprising:
   administering a test agent to the transgenic mouse of claim 1 and subsequently assessing the presence and/or severity of one or more behaviours in the transgenic mouse relative to the same one or more behaviours in a control transgenic mouse, which has not been exposed to the test agent,
   wherein said behaviours are selected from the group consisting of reduced motor activity in an open-field test; reduced time spent in open arms of an elevated plus maze; reduced time spend in the lit portion of a light-dark box; increased latency to feed in a Novelty Suppressed Feeding test; increased immobility time in tail suspension test; and decreased sucrose intake, and wherein the test agent is found to reduce the presence and/or severity of said one or more behaviours.

9. The method according to claim 8, which further comprises isolating the test agent and, optionally, formulating the test agent into a pharmaceutical composition with at least one pharmaceutically acceptable salt, carrier or excipient.

* * * * *

UNITED STATES PATENT AND TRADEMARK OFFICE
CERTIFICATE OF CORRECTION

PATENT NO. : 9,398,761 B2  
APPLICATION NO. : 14/386319  
DATED : July 26, 2016  
INVENTOR(S) : Arteta et al.

Page 1 of 1

It is certified that error appears in the above-identified patent and that said Letters Patent is hereby corrected as shown below:

In the Claims

Claim 2, Column 69, Line 41, "PIN" should read --PTN--.

Claim 2, Column 69, Line 42, "2" should read --2;--.

Claim 2, Column 69, Line 43, "PIN" should read --PTN--.

Claim 2, Column 69, Line 46, "PIN" should read --PTN--.

Claim 2, Column 69, Line 47, "PIN" should read --PTN--.

Claim 8, Column 70, Line 41, "spend" should read --spent--.

Signed and Sealed this  
Ninth Day of May, 2017

Michelle K. Lee  
*Director of the United States Patent and Trademark Office*

UNITED STATES PATENT AND TRADEMARK OFFICE
CERTIFICATE OF CORRECTION

PATENT NO. : 9,398,761 B2
APPLICATION NO. : 14/386319
DATED : July 26, 2016
INVENTOR(S) : Arteta et al.

It is certified that error appears in the above-identified patent and that said Letters Patent is hereby corrected as shown below:

On the Title Page

Item (72) Inventor is corrected to read:
-- David Arteta, Derio (ES);
Marcelo Ferrer, Derio (ES);
Laureano Simon, Derio (ES);
Antonio Martinez, Derio (ES);
Maria Uribarri, Derio (ES);
José Javier Meana, Leioa (ES);
Luis Felipe Callado, Leioa (ES) --.

Signed and Sealed this
Fourteenth Day of April, 2020

Andrei Iancu
*Director of the United States Patent and Trademark Office*